United States Patent
Barton et al.

(10) Patent No.: US 10,342,542 B2
(45) Date of Patent: Jul. 9, 2019

(54) SURGICAL STAPLER BUTTRESS APPLICATOR WITH END EFFECTOR ACTUATED RELEASE MECHANISM

(71) Applicant: Ethicon Endo-Surgery, LLC, Guaynabo, PR (US)

(72) Inventors: Trevor J. Barton, Cincinnati, OH (US); Mark S. Zeiner, Mason, OH (US); Emily A. Schellin, Cincinnati, OH (US); Prudence A. Turner, Independence, KY (US); Charles J. Scheib, Loveland, OH (US); Jason L. Harris, Lebanon, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 606 days.

(21) Appl. No.: 14/926,267

(22) Filed: Oct. 29, 2015

(65) Prior Publication Data

US 2017/0056016 A1  Mar. 2, 2017

Related U.S. Application Data

(60) Provisional application No. 62/209,041, filed on Aug. 24, 2015.

(51) Int. Cl.
*A61B 17/10* (2006.01)
*A61B 17/072* (2006.01)
(Continued)

(52) U.S. Cl.
CPC .......... *A61B 17/105* (2013.01); *A61B 17/068* (2013.01); *A61B 17/07292* (2013.01);
(Continued)

(58) Field of Classification Search
CPC ............... A61B 17/105; A61B 17/068; A61B 17/07292; A61B 2017/07271;
(Continued)

(56) References Cited

U.S. PATENT DOCUMENTS

| 4,805,823 A | 2/1989 | Rothfuss |
| 5,415,334 A | 5/1995 | Williamson et al. |

(Continued)

FOREIGN PATENT DOCUMENTS

| CN | 104 379 068 A | 2/2015 |
| EP | 2 090 248 A2 | 8/2009 |

(Continued)

OTHER PUBLICATIONS

European Search Report and Written Opinion dated Jan. 30, 2017 for Application No. EP 16185376.7, 14 pgs.
(Continued)

*Primary Examiner* — Donnell A Long
(74) *Attorney, Agent, or Firm* — Frost Brown Todd LLC

(57) ABSTRACT

An apparatus includes a housing, a platform, a buttress assembly, a retainer member, and a release assembly. The housing defines a gap that is configured to receive a portion of an end effector of a surgical stapler. A portion of the platform is exposed in the gap defined by the housing. The buttress assembly is positioned on the platform and is exposed in the gap defined by the housing. The retainer member is configured to selectively retain the first buttress assembly against the platform. The release assembly is in communication with the retainer member. The release assembly is configured to store energy. The release assembly is further configured to release the stored energy to thereby cause the at least one retainer to release the first buttress
(Continued)

assembly from the platform in response to a clamping action of an end effector positioned in the gap defined by the housing.

20 Claims, 37 Drawing Sheets

(51) Int. Cl.
*A61B 17/068* (2006.01)
*A61B 17/00* (2006.01)
*A61B 90/00* (2016.01)

(52) U.S. Cl.
CPC . *A61B 17/07207* (2013.01); *A61B 2017/0053* (2013.01); *A61B 2017/00115* (2013.01); *A61B 2017/00477* (2013.01); *A61B 2017/00951* (2013.01); *A61B 2017/07257* (2013.01); *A61B 2017/07271* (2013.01); *A61B 2017/07278* (2013.01); *A61B 2090/037* (2016.02); *A61B 2090/0811* (2016.02)

(58) Field of Classification Search
CPC .......... A61B 2017/07257; A61B 2017/00951; A61B 2090/037; A61B 2017/00477; A61B 2017/00115; A61B 2090/0811; A61B 17/07207; A61B 2017/07278; A61B 2017/0053

See application file for complete search history.

(56) References Cited

U.S. PATENT DOCUMENTS

| | | |
|---|---|---|
| 5,441,191 A | 8/1995 | Linden |
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,752,965 A | 5/1998 | Francis et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,273,897 B1 | 8/2001 | Dalessandro et al. |
| 6,364,888 B1 | 4/2002 | Niemeyer et al. |
| 6,783,524 B2 | 8/2004 | Anderson et al. |
| 6,939,358 B2 | 9/2005 | Palacios et al. |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney |
| 7,691,098 B2 | 4/2010 | Wallace |
| 7,721,930 B2 | 5/2010 | McKenna et al. |
| 7,806,891 B2 | 10/2010 | Nowlin et al. |
| 8,141,762 B2 | 3/2012 | Bedi et al. |
| 8,210,411 B2 | 7/2012 | Yates et al. |
| 8,371,491 B2 | 2/2013 | Huitema et al. |
| 8,408,439 B2 | 4/2013 | Huang et al. |
| 8,453,914 B2 | 6/2013 | Laurent et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,801,735 B2 | 8/2014 | Shelton, IV et al. |
| 8,814,025 B2 | 8/2014 | Miller et al. |
| 8,820,605 B2 | 9/2014 | Shelton, IV |
| 8,844,789 B2 | 9/2014 | Shelton, IV et al. |
| 8,899,464 B2 | 12/2014 | Hueil et al. |
| 8,998,060 B2 | 4/2015 | Bruewer et al. |
| 9,101,359 B2 | 8/2015 | Smith et al. |
| 9,186,142 B2 | 11/2015 | Fanelli et al. |
| 9,198,644 B2 | 12/2015 | Balek et al. |
| 9,198,662 B2 | 12/2015 | Barton et al. |
| 9,211,120 B2 | 12/2015 | Scheib et al. |
| 9,301,759 B2 | 4/2016 | Spivey et al. |
| 9,307,965 B2 | 4/2016 | Ming et al. |
| 9,364,233 B2 | 6/2016 | Alexander, III et al. |
| 9,393,018 B2 | 7/2016 | Wang et al. |
| 9,398,911 B2 | 7/2016 | Auld |
| 9,445,808 B2 | 9/2016 | Woodard et al. |
| 9,492,170 B2 | 11/2016 | Bear et al. |
| 9,517,065 B2 | 12/2016 | Simms et al. |
| 10,052,105 B2 | 8/2018 | Tannhauser et al. |
| 10,166,023 B2 | 1/2019 | Vendely et al. |
| 2003/0120284 A1* | 6/2003 | Palacios ........... A61B 17/07207 606/139 |
| 2005/0070929 A1 | 3/2005 | Dalessandro et al. |
| 2006/0173470 A1 | 8/2006 | Oray et al. |
| 2008/0169328 A1 | 7/2008 | Shelton, IV |
| 2009/0206126 A1 | 8/2009 | Huitema et al. |
| 2009/0206131 A1* | 8/2009 | Weisenburgh, II .......... A61B 17/07207 227/175.2 |
| 2010/0234861 A1 | 9/2010 | Oray et al. |
| 2011/0290853 A1* | 12/2011 | Shelton, IV ..... A61B 17/07207 227/177.1 |
| 2011/0290856 A1* | 12/2011 | Shelton, IV ........... A61B 34/30 227/180.1 |
| 2012/0241492 A1 | 9/2012 | Shelton, IV et al. |
| 2012/0241493 A1 | 9/2012 | Baxter, III et al. |
| 2012/0241503 A1* | 9/2012 | Baxter, III ......... A61B 17/0643 227/176.1 |
| 2012/0241505 A1* | 9/2012 | Alexander, III ........... A61B 17/00491 227/179.1 |
| 2012/0292367 A1* | 11/2012 | Morgan ............. A61B 17/072 227/175.1 |
| 2013/0062391 A1 | 3/2013 | Boudreaux et al. |
| 2013/0068816 A1 | 3/2013 | Vasudevan et al. |
| 2013/0075447 A1 | 3/2013 | Weisenburgh, II et al. |
| 2013/0146643 A1* | 6/2013 | Schmid ............. A61B 17/0682 227/180.1 |
| 2013/0161374 A1* | 6/2013 | Swayze ................ A61B 17/068 227/176.1 |
| 2013/0206813 A1 | 8/2013 | Nalagatla |
| 2013/0214030 A1 | 8/2013 | Aronhalt et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0263563 A1 | 9/2014 | Stokes et al. |
| 2015/0272575 A1 | 10/2015 | Leimbach et al. |
| 2015/0351754 A1 | 12/2015 | Harris et al. |
| 2015/0351758 A1 | 12/2015 | Shelton, IV et al. |
| 2015/0351763 A1 | 12/2015 | Shelton, IV et al. |
| 2015/0374360 A1 | 12/2015 | Scheib et al. |
| 2015/0374373 A1 | 12/2015 | Rector et al. |
| 2016/0089142 A1 | 3/2016 | Harris et al. |
| 2016/0089146 A1 | 3/2016 | Harris et al. |
| 2016/0278774 A1 | 9/2016 | Shelton, IV et al. |
| 2017/0027567 A1 | 2/2017 | Scheib et al. |
| 2017/0027568 A1 | 2/2017 | Scheib et al. |
| 2017/0027569 A1 | 2/2017 | Scheib et al. |
| 2017/0049444 A1 | 2/2017 | Schellin et al. |
| 2017/0055980 A1 | 3/2017 | Vendely et al. |
| 2017/0055981 A1 | 3/2017 | Vendely et al. |
| 2017/0055982 A1 | 3/2017 | Zeiner et al. |

(56) References Cited

U.S. PATENT DOCUMENTS

2017/0055986 A1 3/2017 Harris et al.
2017/0056017 A1 3/2017 Vendely et al.
2017/0056018 A1 3/2017 Zeiner et al.

FOREIGN PATENT DOCUMENTS

| EP | 2 764 833 A2 | 8/2014 |
| EP | 3 072 457 A2 | 9/2016 |
| EP | 3072460 A2 | 9/2016 |
| WO | WO 2005/079675 A2 | 9/2005 |
| WO | WO 2013/119365 A1 | 8/2013 |

OTHER PUBLICATIONS

European Search Report and Written Opinion dated Jan. 24, 2017 for Application No. EP 16185387.4, 10 pgs.
International Search Report and Written Opinion dated Dec. 23, 2016 for Application No. PCT/US2016/048352, 16 pgs.
International Search Report and Written Opinion dated Feb. 17, 2017 for Application No. PCT/US2016/048356, 17 pgs.
International Search Report and Written Opinion dated Jan. 2, 2017 for Application No. PCT/US2016/048359, 12 pgs.
International Search Report and Written Opinion dated Dec. 21, 2016 for Application No. PCT/US2016/048362, 11 pgs.
International Search Report and Written Opinion dated Dec. 6, 2016 for Application No. PCT/US2016/048364, 12 pgs.
U.S. Appl. No. 14/871,071, filed Sep. 30, 2015.
U.S. Appl. No. 14/871,131, filed Sep. 30, 2015.
U.S. Appl. No. 14/926,027, filed Oct. 29, 2015.
U.S. Appl. No. 14/926,029, filed Oct. 29, 2015.
U.S. Appl. No. 14/926,045, filed Oct. 29, 2015.
U.S. Appl. No. 14/926,057, filed Oct. 29, 2015.
U.S. Appl. No. 14/926,072, filed Oct. 29, 2015.
U.S. Appl. No. 14/926,090, filed Oct. 29, 2015.
U.S. Appl. No. 14/926,131, filed Oct. 29, 2015.
U.S. Appl. No. 14/926,160, filed Oct. 29, 2016.
U.S. Appl. No. 14/926,194, filed Oct. 29, 2015.
U.S. Appl. No. 62/209,041, filed Aug. 24, 2015.
Extended European Search Report and Written Opinion dated Jan. 20, 2017 for Application No. EP 16185368.4, 10 pgs.
Extended European Search Report and Written Opinion dated Jan. 24, 2017 for Application No. EP 16185370.0, 11 pgs.
Extended European Search Report and Written Opinion dated Jun. 8, 2017 for Application No. EP 16185375.9, 16 pgs.
U.S. Appl. No. 14/926,296.
U.S. Appl. No. 14/926,322.
U.S. Appl. No. 14/926,358.
U.S. Appl. No. 14/926,609.
U.S. Appl. No. 14/926,764.
U.S. Appl. No. 16/191,722.
U.S. Appl. No. 16/211,436.
U.S. Appl. No. 16/211,438.
European Search Report, Extended, and Written Opinion dated Oct. 18, 2017 for Application No. EP 18182626.4, 8 pgs.
European Exam Report dated Oct. 16, 2018 for Application No. EP 16185368.4, 4 pgs.
European Examination Report dated Jan. 3, 2018 for Application No. EP 16185368.4, 4 pgs.
European Examination Report dated Jan. 15, 2018 for Application No. EP 16185370.0, 4 pgs.

\* cited by examiner

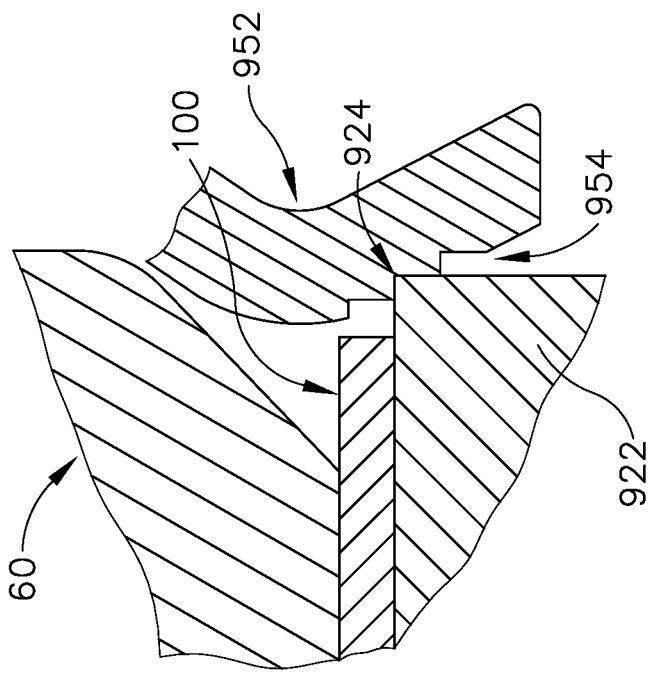
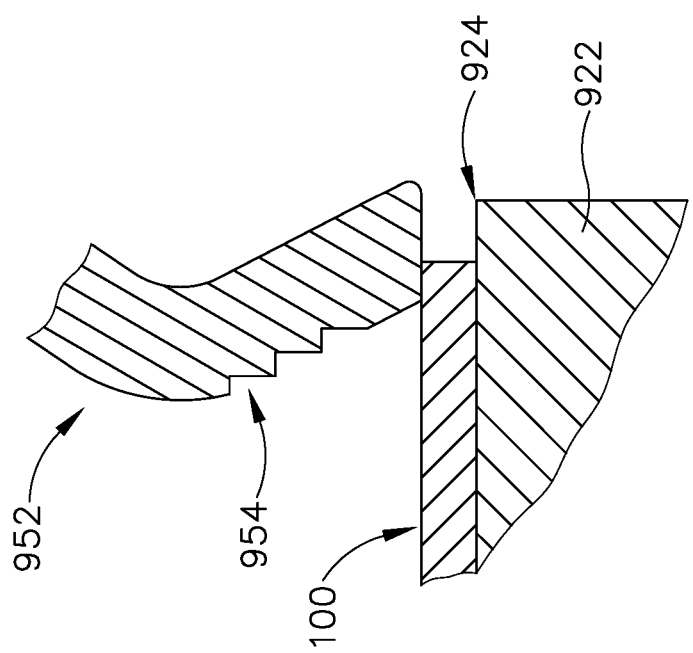
Fig. 27B
Fig. 27A

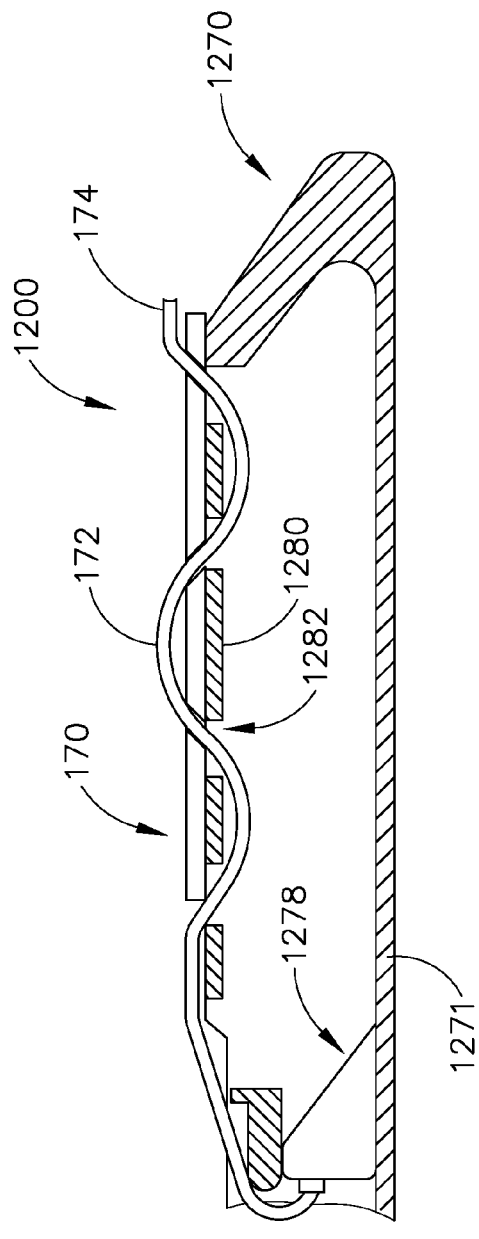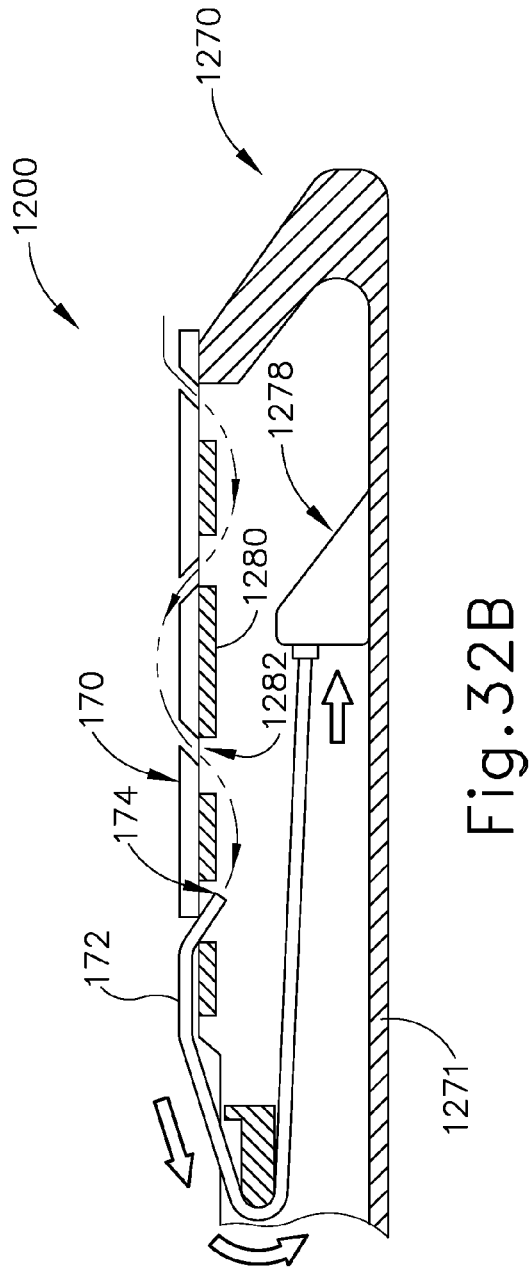

SURGICAL STAPLER BUTTRESS APPLICATOR WITH END EFFECTOR ACTUATED RELEASE MECHANISM

PRIORITY

This application claims priority to U.S. Patent App. No. 62/209,041, entitled "Method and Apparatus for Applying a Buttress to End Effector of a Surgical Stapler," filed Aug. 24, 2015, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue", issued as U.S. Pat. No. 9,936,954 on Apr. 10, 2018; and U.S. patent application Ser. No. 14/498,070, entitled "Radically Expandable Staple Line" filed Sep. 26, 2014, published as U.S. Pub. No. 2016/0089146 on Mar. 31, 2016. The disclosure of each of the above-cited U.S. patents, U.S. Patent Publications, and U.S. patent applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 27A depicts a partial, cross-sectional detail view of a ratcheting retention arm of the buttress applier cartridge of FIG. 26A in the buttress engaging configuration;

FIG. 27B depicts a partial, cross-sectional detail view of a ratcheting retention arm of the buttress applier cartridge of FIG. 26A in the buttress disengaging configuration;

FIG. 32A depicts a cross-sectional side view of the staple cartridge of FIG. 30, with a wedge sled in a proximal position;

FIG. 32B depicts a cross-sectional side view of the staple cartridge of FIG. 30, with the wedge sled in a distal position;

Figure 1:
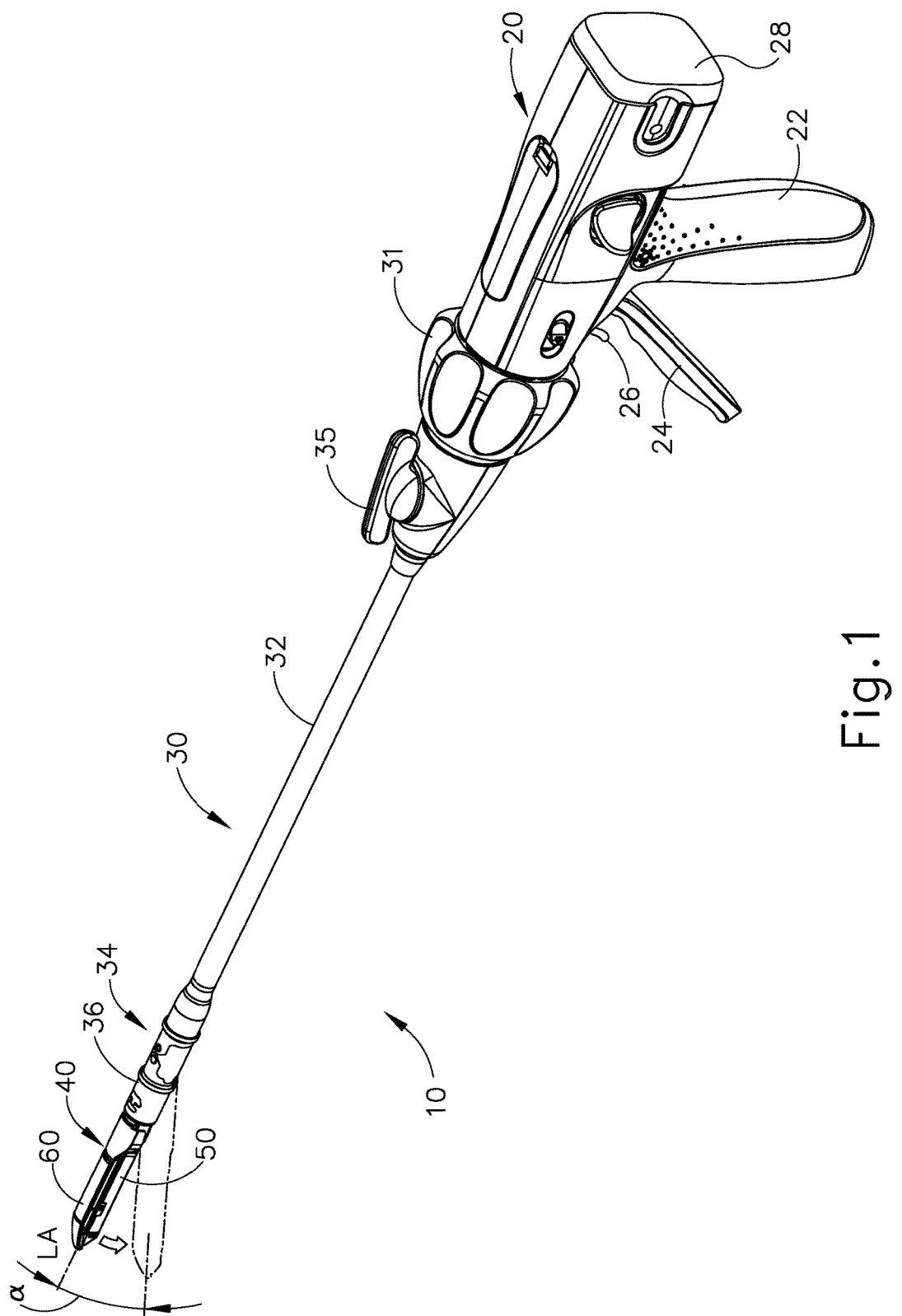
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
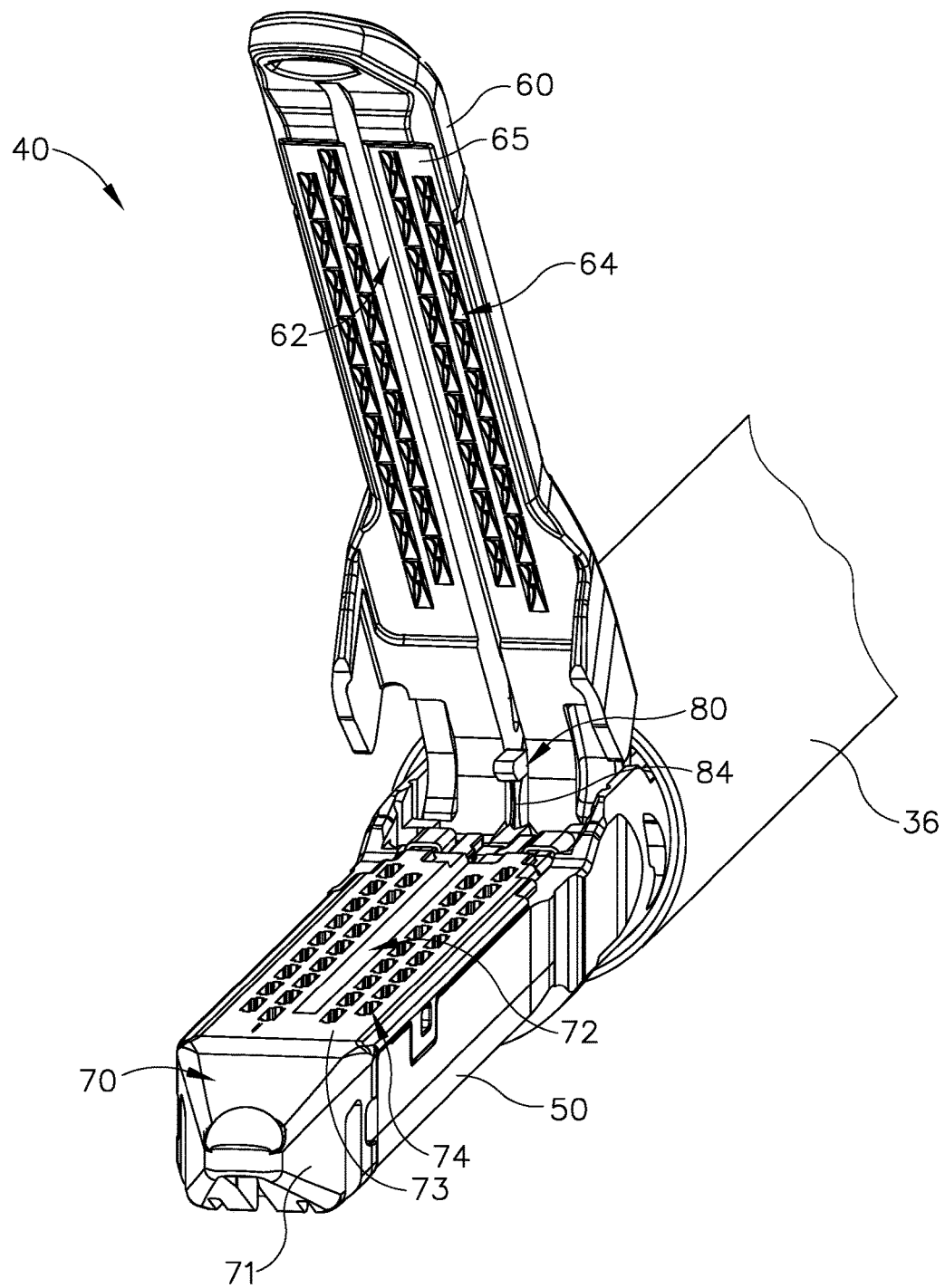
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein; and/or U.S. patent application Ser. No. 14/314,125, entitled "Articulation Drive Features for Surgical Stapler," filed Jun. 25, 2014, published as U.S. Pub. No. 2015/0374360 on Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
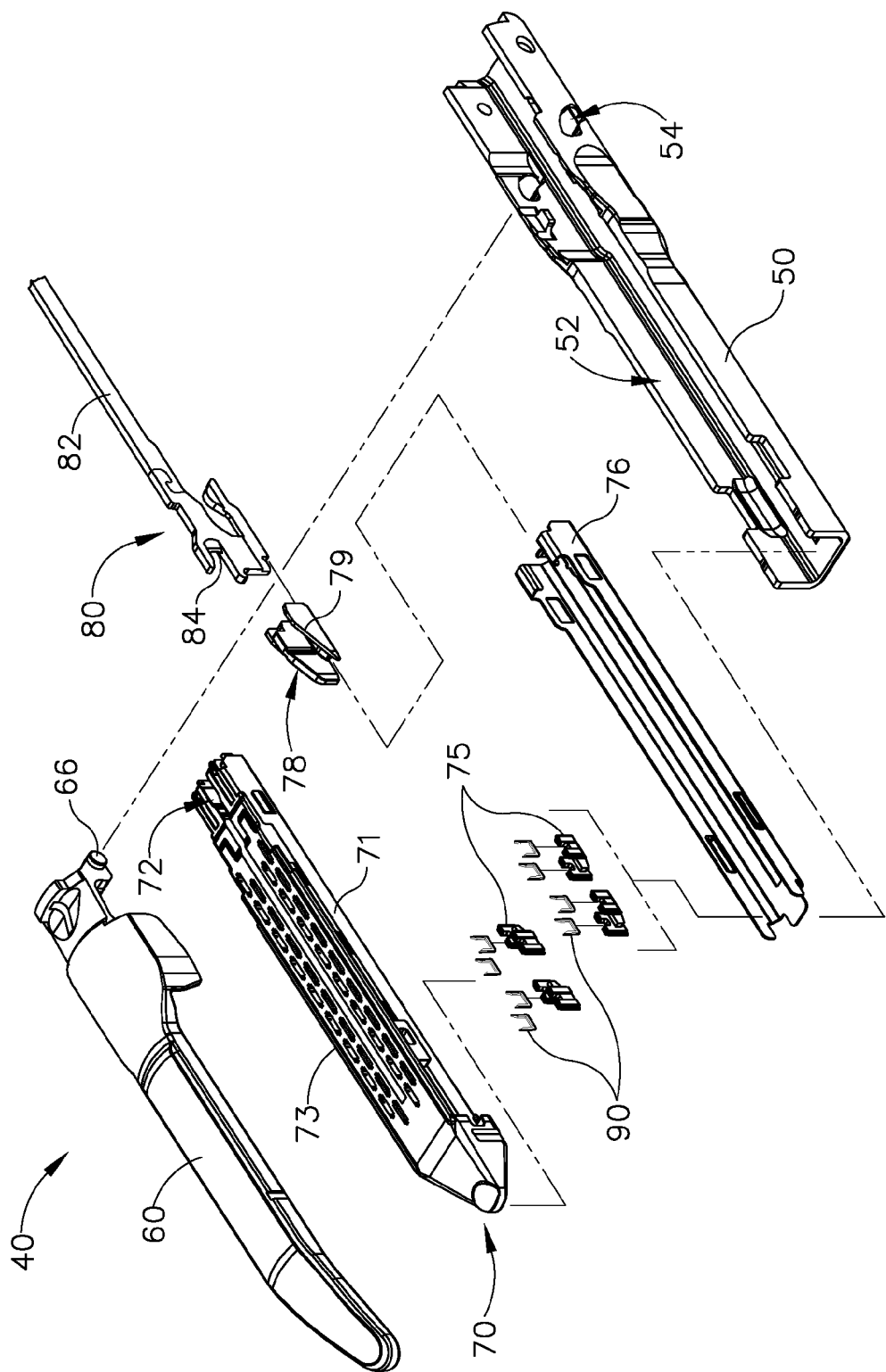
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 30, 2016, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, published as U.S. Pub. No. 2015/0374373 on Dec. 31, 2015, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Assembly for Surgical Stapler

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

Figure 4:
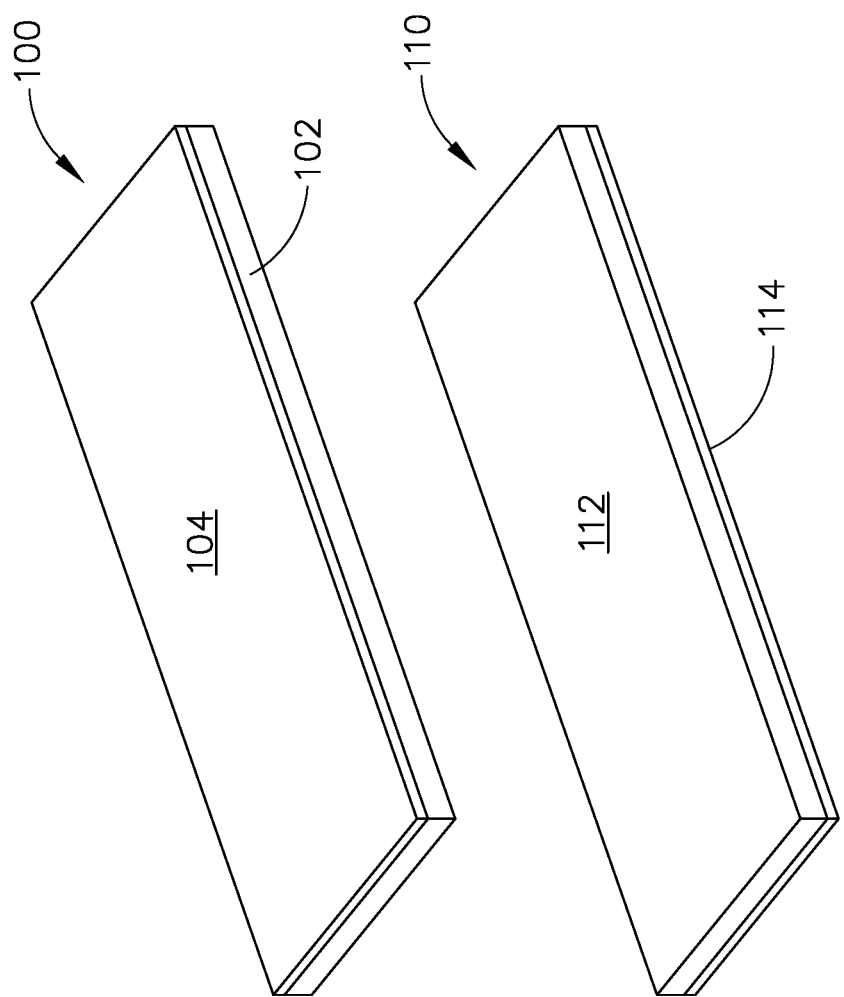
FIG. 4 depicts a perspective view of an exemplary upper buttress and an exemplary lower buttress, each of which may be applied to the end effector of FIG. 2.

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a woven mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGI-CEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, issued as U.S. Pat. No. 10,172,611 on Jan. 8, 2019, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, published as U.S. Pub. No. 2017/0055986 on Mar. 2, 2017, the disclosure of which is incorporated by reference herein; U.S. patent application Ser. No. 14/871,071, entitled "Compressible Adjunct with Crossing Spacer Fibers," filed Sep. 30, 2015, published as U.S. Pub. No. 2017/0086837 on Mar. 30, 2017, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100, 110) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

Figure 5:
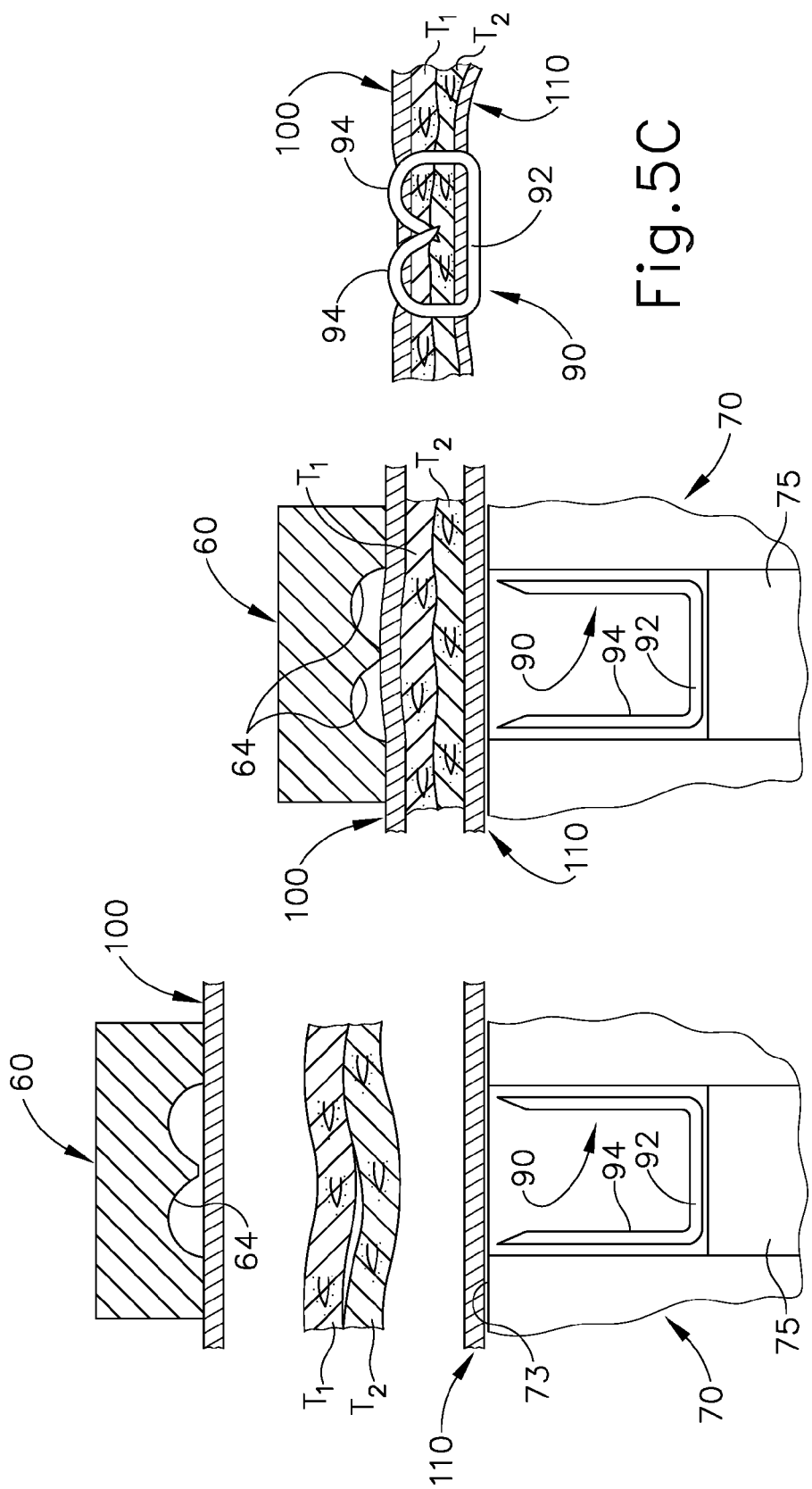
FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position.
FIG. 5B depicts a cross-sectional end view of the combined end effector and buttress assembly of FIG. 5A, with tissue positioned between the buttresses in the end effector, and with the anvil in a closed position.
FIG. 5C depicts a cross-sectional view of a staple and the buttress assembly of FIG. 5A having been secured to the tissue by the end effector of FIG. 2.

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
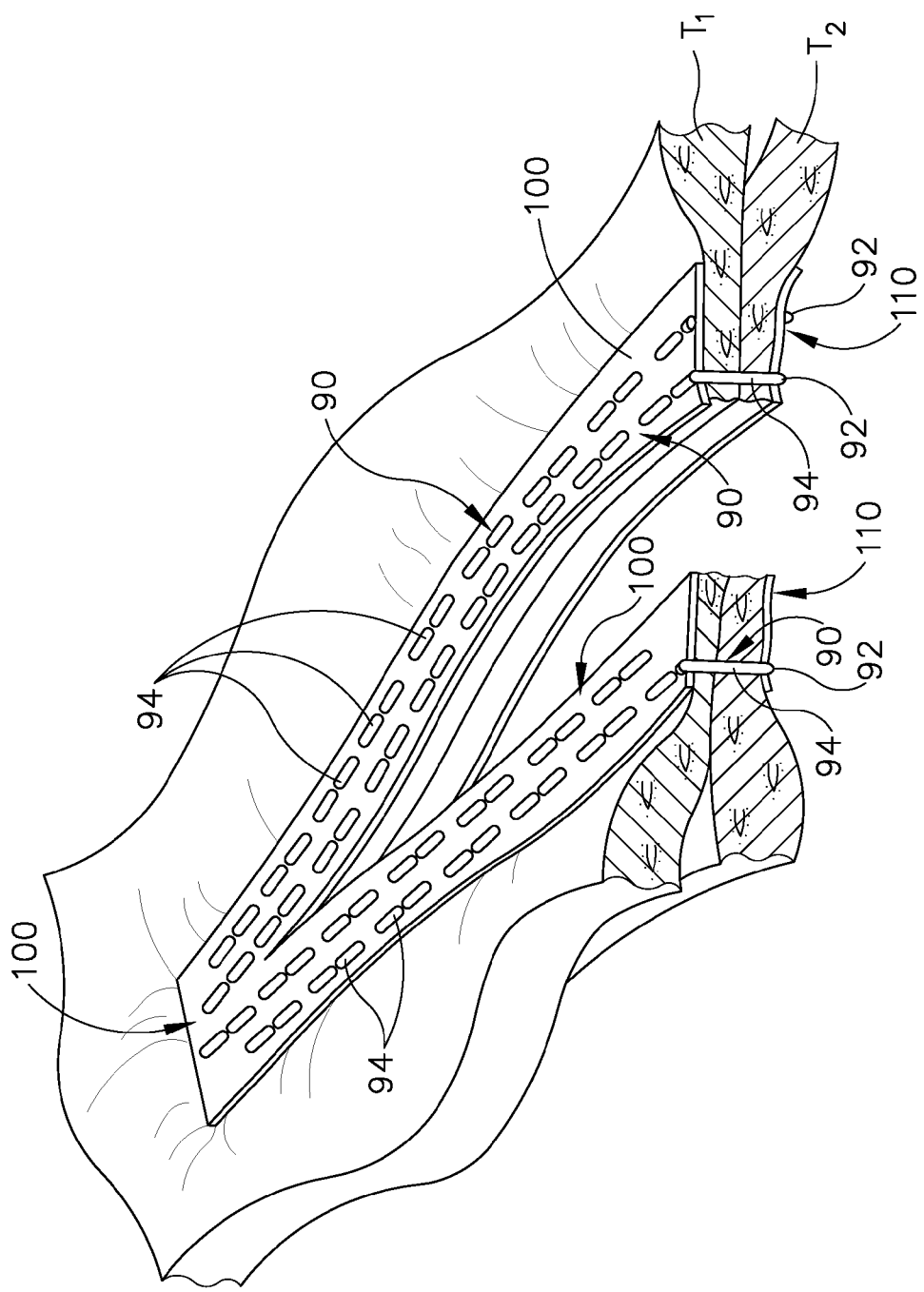
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein.

III. Exemplary Buttress Applier Cartridges

As noted above, buttress assembly (100) may be applied to the underside (65) of anvil (60), and buttress (110) may be applied to deck (73) of staple cartridge (70), before tissue ($T_1$, $T_2$) is positioned in end effector (40), and before end effector (40) is actuated. Because end effector (40) may be actuated many times during use of instrument (10) in a single surgical procedure, it may be desirable to enable an operator to repeatedly and easily load buttress assemblies (100) on underside (65) of anvil (60) during that single surgical procedure. In other words, because end effector (40) may be actuated many times during use of instrument (10) in a single surgical procedure, it may be insufficient to simply provide anvil (60) pre-loaded with a buttress assembly (100) without facilitating the re-loading of anvil (60) with additional buttress assemblies (100) after end effector (40) has been actuated.

Similarly, those of ordinary skill in the art will recognize that staple cartridge (70) will need to be replaced each time end effector (40) is actuated. When end effector (40) is actuated several times during use of instrument (10) in a single surgical procedure, several staple cartridges (70) may thus be used during that surgical procedure. It may seem that each of these staple cartridges (70) may be provided with buttress assembly (110) pre-loaded on deck (73). However, there are some reasons why it may be undesirable to provide a staple cartridge (70) with buttress assembly (110) pre-loaded on deck (73). In other words, it may be desirable to provide loading of buttress assembly (110) on deck (73) immediately prior to usage of staple cartridge in the surgical procedure, rather than loading buttress assembly (110) on deck (73) a substantial time prior to the surgical procedure. For instance, buttress assembly (110) may not be compatible with the same sterilization techniques as staple cartridge (70), such that it may present processing difficulties to package staple cartridge (70) with buttress assembly (110) pre-loaded on deck (73). In addition, the material forming buttress assembly (110) may have certain environmental sensitivities that staple cartridge (70) does not have, such that it may be beneficial to enable buttress assembly (110) and staple cartridge (70) to be stored separately before use. Moreover, buttress assembly (110) may not be warranted or otherwise desired in some surgical procedures, such that it may be desirable to enable a physician to easily choose whether staple cartridge (70) should be loaded with buttress assembly (110) before that staple cartridge (70) is used in the surgical procedure.

In view of the foregoing, it may be desirable to enable an operator to repeatedly and easily load buttress assemblies (100, 110) on end effector (40) on an ad hoc basis during a given surgical procedure. It may also be desirable to provide a device that provides support and protection to buttress assemblies (100, 110) before buttress assemblies (100, 110) are loaded on end effector (40), in addition to that same device also enabling buttress assemblies (100, 110) to be easily loaded on end effector. The examples described below relate to various cartridge assemblies that provide such support, protection, and loading of buttress assemblies (100, 110). It should be understood that the following examples are merely illustrative. Numerous variations will be apparent to those of ordinary skill in the art in view of the teachings herein.

A. Exemplary Buttress Applier Cartridge with Active Retainer Arms

Figure 7:
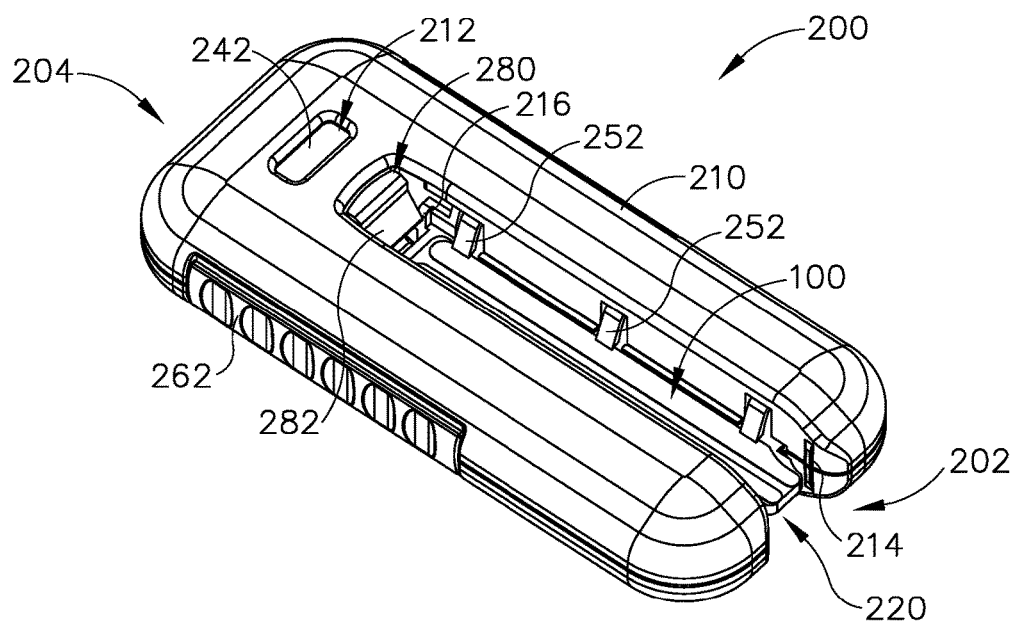
FIG. 7 depicts a perspective view of an exemplary buttress applier cartridge that may be used to carry and apply the buttress assembly of FIG. 5A.
Figure 8:
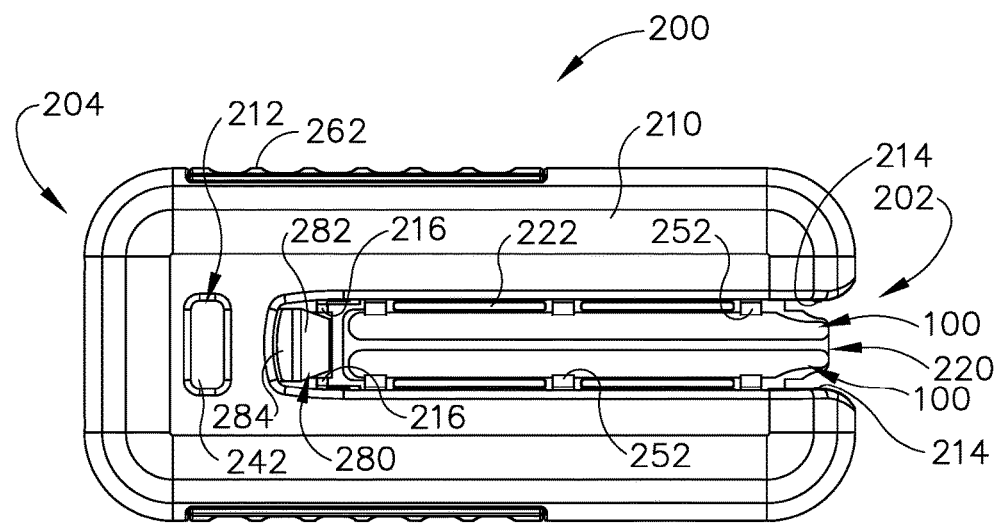
FIG. 8 depicts a top plan view of the buttress applier cartridge of FIG. 7.
Figure 9:
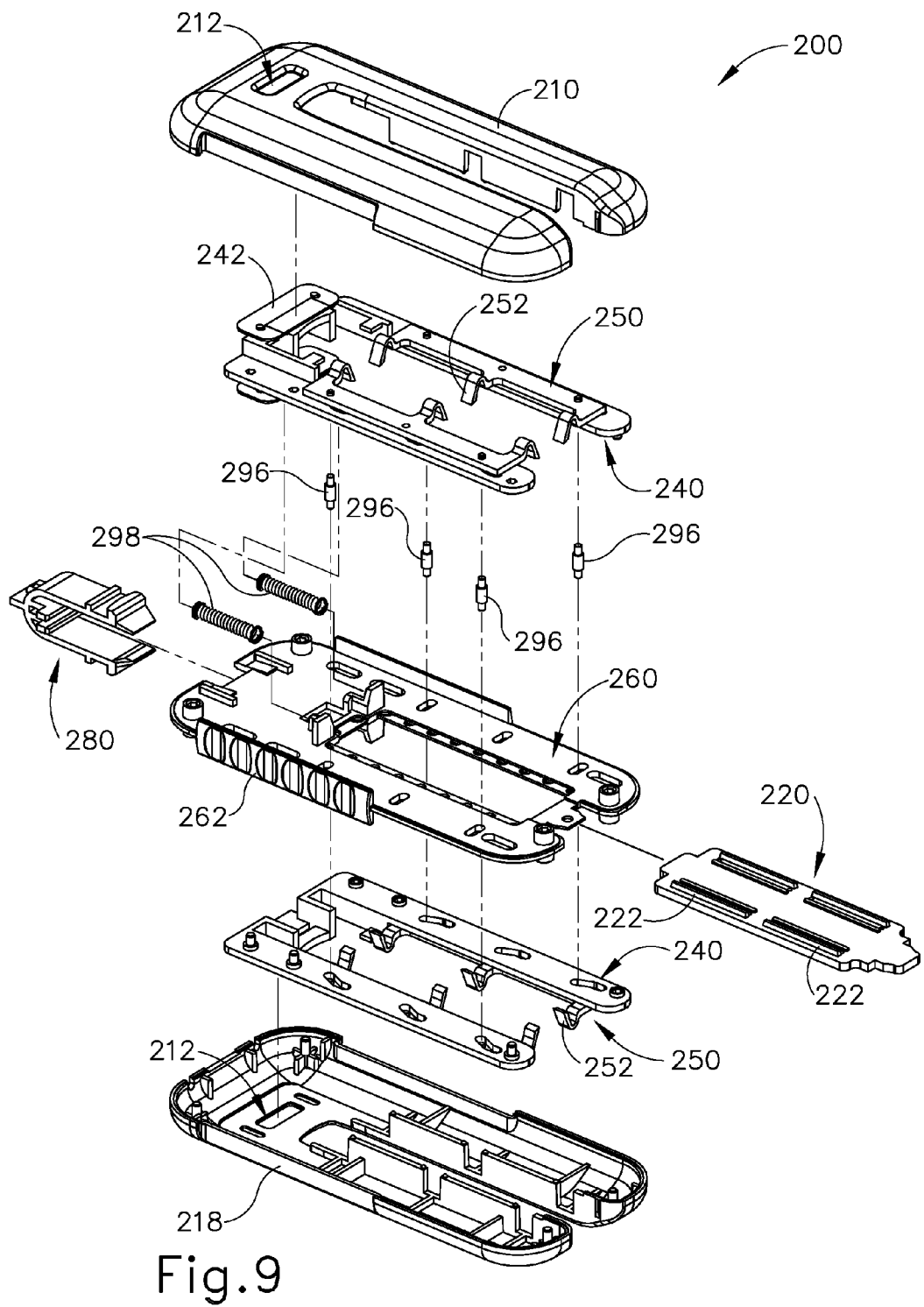
FIG. 9 depicts an exploded perspective view of the buttress applier cartridge of FIG. 7.

FIGS. 7-17B show an exemplary buttress applier cartridge (200) that may be used to support and protect buttress assemblies (100, 110). Cartridge (200) may also be used to easily load buttress assemblies (100, 110) on end effector (40). As best seen in FIGS. 7-8, cartridge (200) of this example comprises an open end (202) and a closed end (204). Open end (202) is configured to receive end effector (40) as will be described in greater detail below. Cartridge (200) further includes a first housing (210) and a second housing (218), which each generally define a "U" shape to present open end (202). As best seen in FIG. 9, various components are interposed between housings (210, 218). In particular, these components include a platform (220), a pair of actuator sleds (240), a pair of retainers (250), a chassis (260), and a sled retainer (280). Each of these components will be described in greater detail below.

Platform (220) of the present example is configured to support a pair of buttress assemblies (100) on one side of platform (220) and another pair of buttress assemblies (110) on the other side of platform (220). Platform (220) is exposed in recesses that are formed between the prongs of the "U" configuration of housings (210, 218). The location of platform (220) and buttress assemblies (100, 110) in such recesses may prevent inadvertent contact between buttress assemblies (100, 110) and other devices in the operating room. In other words, housings (210, 218) may provide some degree of physical shielding of buttress assemblies (100, 110).

In the present example, each buttress assembly (100, 110) is provided in a respective pair of portions that are separated to avoid spanning across channels (62, 72) of anvil (60) and staple cartridge (70), respectively, though it should be understood that platform (220) may just as easily support wide versions of buttress assemblies (100, 110) that unitarily span across channels (62, 72) of anvil (60) and staple cartridge (70), respectively. The outer edges of platform (220) are captured between housings (210, 218) and include retention features (222) in the form of ridges that further engage housings (210, 218) to prevent platform (220) from sliding relative to housings (210, 218). In some versions, platform (220) is formed of a material that provides a high coefficient of friction, thereby reducing any tendency that buttress assemblies (100, 110) might otherwise have to slide along corresponding surfaces of platform (220). For instance, platform (220) may comprise an elastomeric material and/or a foam material. In some instances, platform (220) is formed of a compressible foam material that is configured to maintain a compressed configuration after being compressed by end effector (40). By way of example only, platform (220) may comprise Santoprene, closed-cell polyurethane foam, any other compressible material, and/or a material that may be made compressible via geometry (e.g., a rubber material with deformable standing features). Various suitable materials and structural configurations that may be used to form platform (220) will be apparent to those of ordinary skill in the art in view of the teachings herein.

Figure 11:
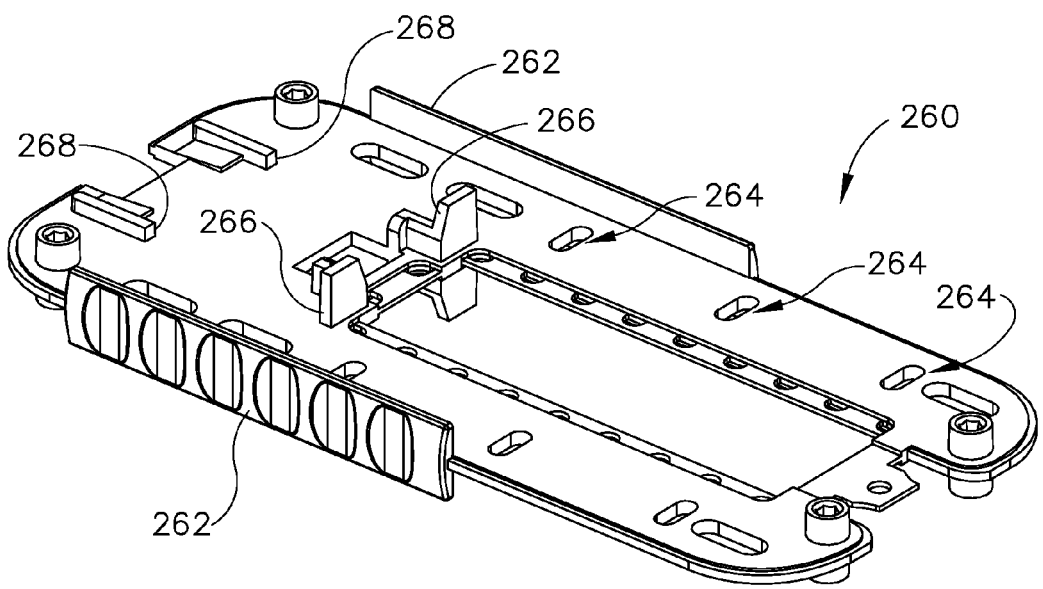
FIG. 11 depicts a perspective view of a chassis of the buttress applier cartridge of FIG. 7.
Figure 15A:
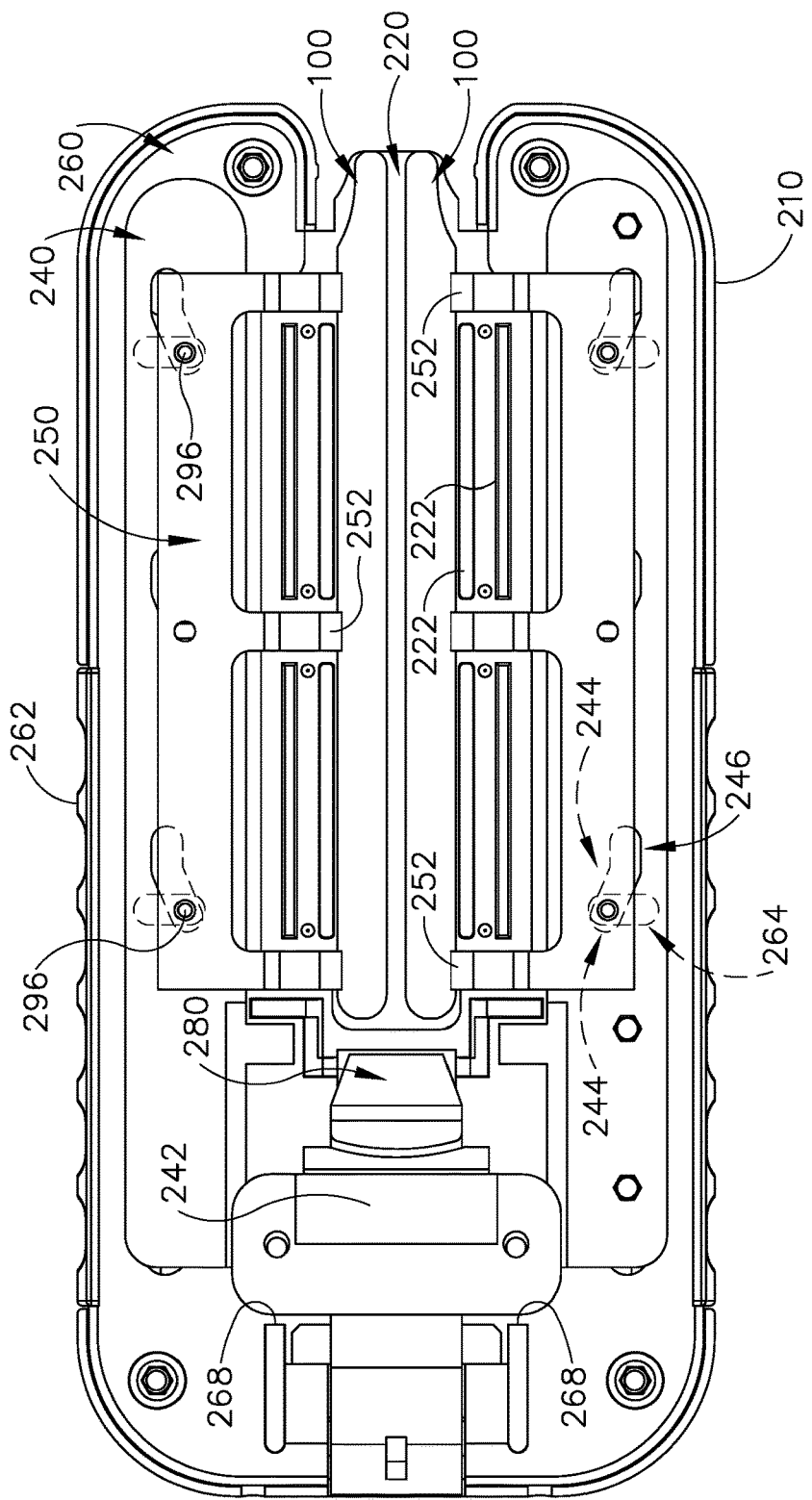
FIG. 15A depicts a top plan view of the buttress applier cartridge of FIG. 7, with a housing member removed, with a buttress assembly loaded on a platform of the buttress applier cartridge, and with retainers positioned to secure the buttress assembly to the platform.
Figure 15B:
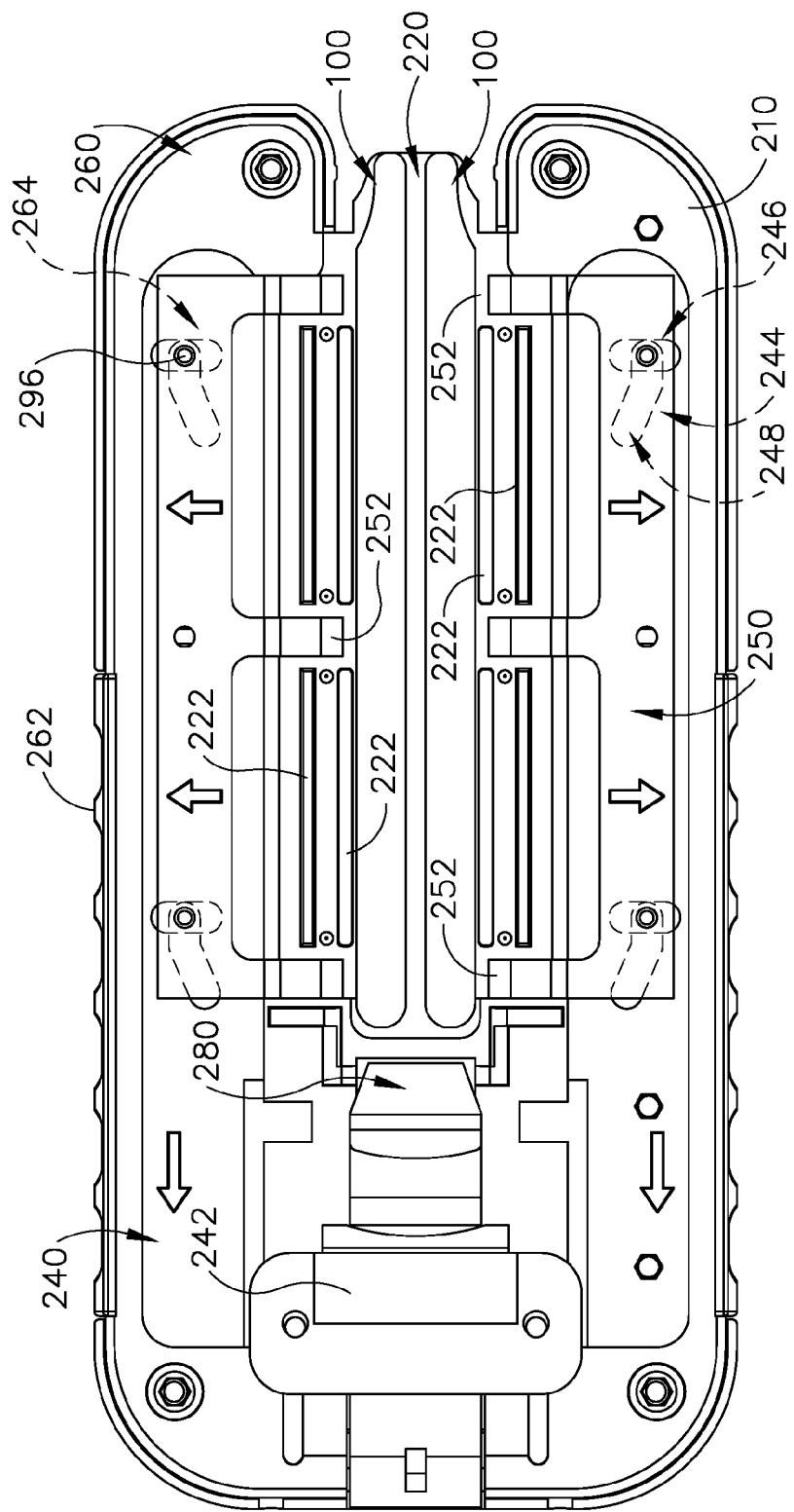
FIG. 15B depicts a top plan view of the buttress applier cartridge of FIG. 7, with a housing member removed, with a buttress assembly loaded on a platform of the buttress applier cartridge, and with retainers positioned to release the buttress assembly to the platform.

Chassis (260) is configured to cooperate with housings (210, 218) to provide a mechanical ground for moving components of cartridge (200) and provide structural support for components of cartridge (200). As shown in FIGS. 7-8, chassis (260) includes integral gripping features (262) that are exposed on opposite sides of housings (210, 218). Gripping features (262) have a surface geometry that is configured to promote an operator's grip of cartridge (200) during use of cartridge (200). Various suitable configurations that may be used for gripping features (262) will be apparent to those of ordinary skill in the art in view of the teachings herein. Similarly, various surface treatments (e.g., elastomeric material, etc.) that may be applied to gripping features (262) will be apparent to those of ordinary skill in the art in view of the teachings herein. As best seen in FIG. 11, chassis (260) further includes a set of laterally oriented slots (264), a first pair of bosses (266), and a second pair of bosses (268). Slots (264) are configured to slidably receive pins (296) as shown in FIGS. 9 and 15A-15B. In particular, pins (296) may translate laterally within slots (264) (i.e. toward and away from the central longitudinal axis extending along the center of platform (220)). In the present example, there are six slots (264) and only four pins (296), such that two of the slots (264) are not used. In other versions, there are six pins (296) such that all six slots (264) are used. In still other versions, there are only four slots (264), corresponding with the four pins (296) of the present example.

Figure 12:
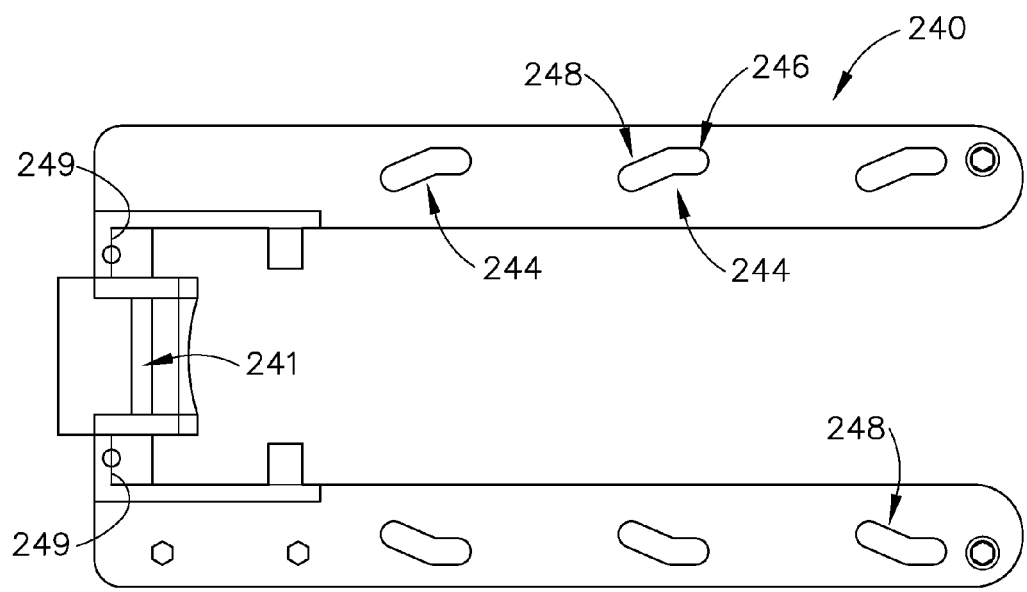
FIG. 12 depicts a top plan view of an actuator sled of the buttress applier cartridge of FIG. 7.

Actuator sleds (240) are slidably positioned on opposite faces of chassis (260). As shown in FIG. 12, each actuator sled includes a locking recess (241), a set of slots (244), and a pair of boss features (249). As shown in FIG. 9, a set of coil springs (298) are positioned between bosses (266) of chassis (260) and boss features (249) of actuator sled (240). Coil springs (298) resiliently bias actuator sleds (240) proximally relative to chassis (260). As will be described in greater detail below, locking recess (241) is configured to selectively engage a locking ridge (286) of sled retainer (280) to selectively lock the longitudinal position of actuator sleds (240) relative to chassis (260), thereby resisting the resilient bias of coil springs (298). As shown in FIGS. 9 and 15A-15B, an indicator plate (242) is secured to the proximal end of each actuator sled (240), such that indicator plates (242) will translate unitarily with actuator sleds (240). Indicator plates (242) are positioned to correspond with windows (212) that are formed in housings (210, 218), such that indicator plates (242) are visible through windows (212) when actuator sleds (240) are in a distal position and when actuator sleds (240) are in a proximal position. As will be described in greater detail below, indicator plates (242) may include different colored regions or other markings that provide visual indication through windows (212), visually indicating whether actuator sleds (240) are in the distal position or the proximal position.

As shown in FIGS. 9 and 15A-15B, slots (244) are positioned to also receive pins (296). Each slot (244) includes a longitudinally extending portion (246) and an obliquely extending portion (248). Pins (296) are configured to travel along the longitudinally extending portion (246) of each corresponding slot (244) and along the obliquely extending portion (248) of each corresponding slot (244). In the present example, there are six slots (244) and only four pins (296), such that two of the slots (244) are not used. In other versions, there are six pins (296) such that all six slots (244) are used. In still other versions, there are only four slots (244), corresponding with the four pins (296) of the present example.

Figure 13:
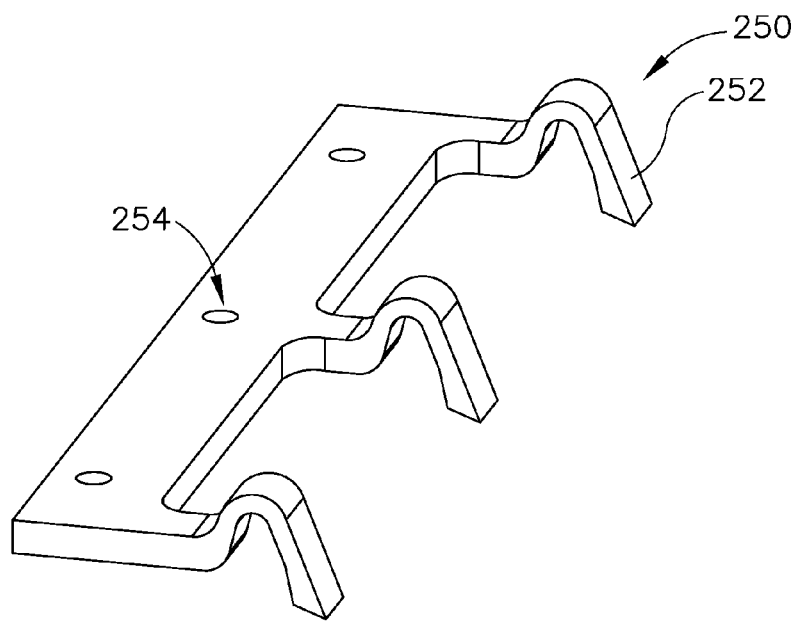
FIG. 13 depicts a perspective view of a retainer of the buttress applier cartridge of FIG. 7.

Retainers (250) are slidably disposed on respective actuator sleds (240), such that each actuator sled (240) is slidably interposed between chassis (260) and a corresponding retainer (250). As shown in FIG. 13, each retainer (250) includes a set of arms (252) and a set of openings (254). Openings (254) are positioned to receive pins (296). Pins (296) are secured within openings (254) such that pins (296) do not move within corresponding openings (254). Retainers (250) thus travel unitarily with pins (296) in this example, as will be described in greater detail below. In the present example, there are six openings (254) and only four pins (296), such that two of the openings (254) are not used. In other versions, there are six pins (296) such that all six openings (254) are used. In still other versions, there are only four openings (254), corresponding with the four pins (296) of the present example.

Arms (252) of the present example are configured to selectively secure buttress assemblies (100, 110) to platform (220). In particular, FIGS. 7-8, 14A, and 15A show retainers (250) positioned such that buttress assemblies (100, 110) are interposed between the free ends of arms (252) and platform (220). As described in greater detail below, retainers (250) are movable laterally outwardly such that arms (252) disengage buttress assemblies (100, 110), thereby enabling buttress assemblies (100, 110) to be removed from platform (220). In the present example, arms (252) are resilient and are thus configured to resiliently bear against buttress assemblies (100, 110), thereby pinching buttress assemblies (100, 110) against platform (220). Other suitable ways in which arms (252) may engage buttress assemblies (100, 110) will be apparent to those of ordinary skill in the art in view of the teachings herein.

Figure 10:
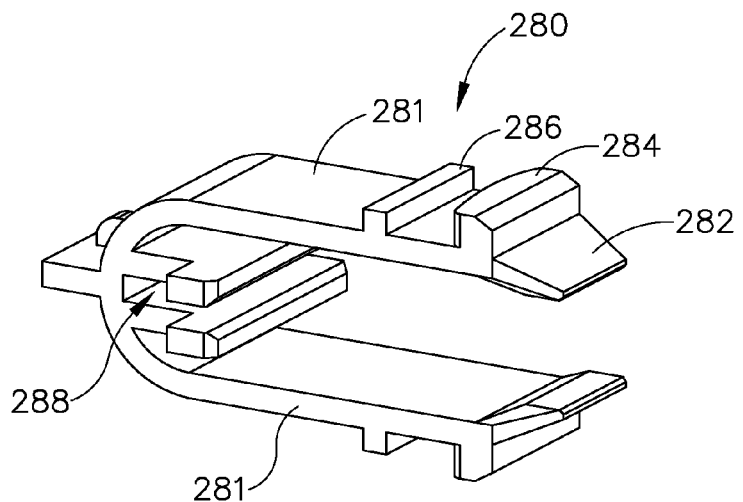
FIG. 10 depicts a perspective view of a sled retainer of the buttress applier cartridge of FIG. 7.
Figure 14A:
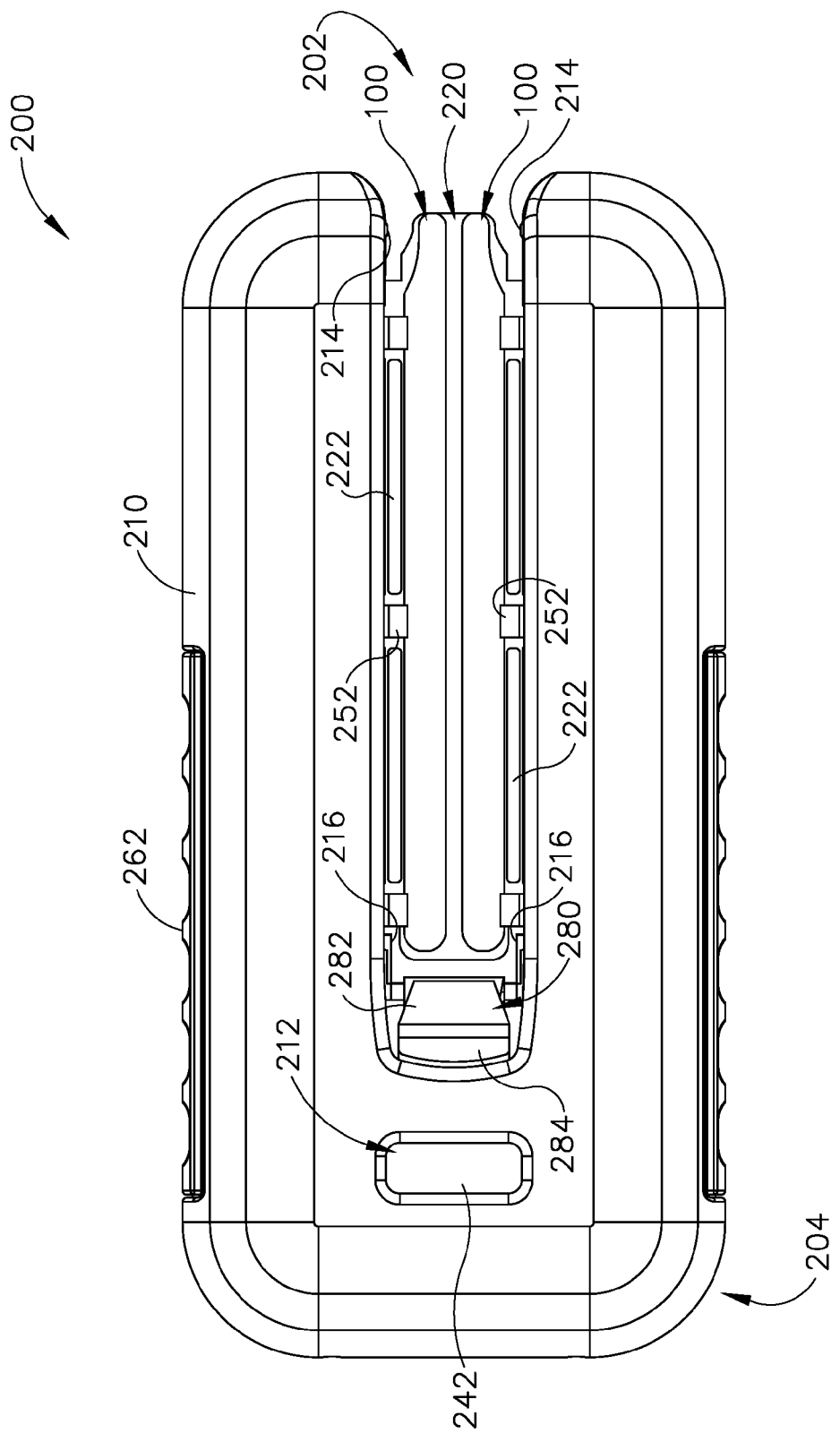
FIG. 14A depicts a top plan view of the buttress applier cartridge of FIG. 7, with a buttress assembly loaded on a platform of the buttress applier cartridge, and with retainers positioned to secure the buttress assembly to the platform.
Figure 14B:
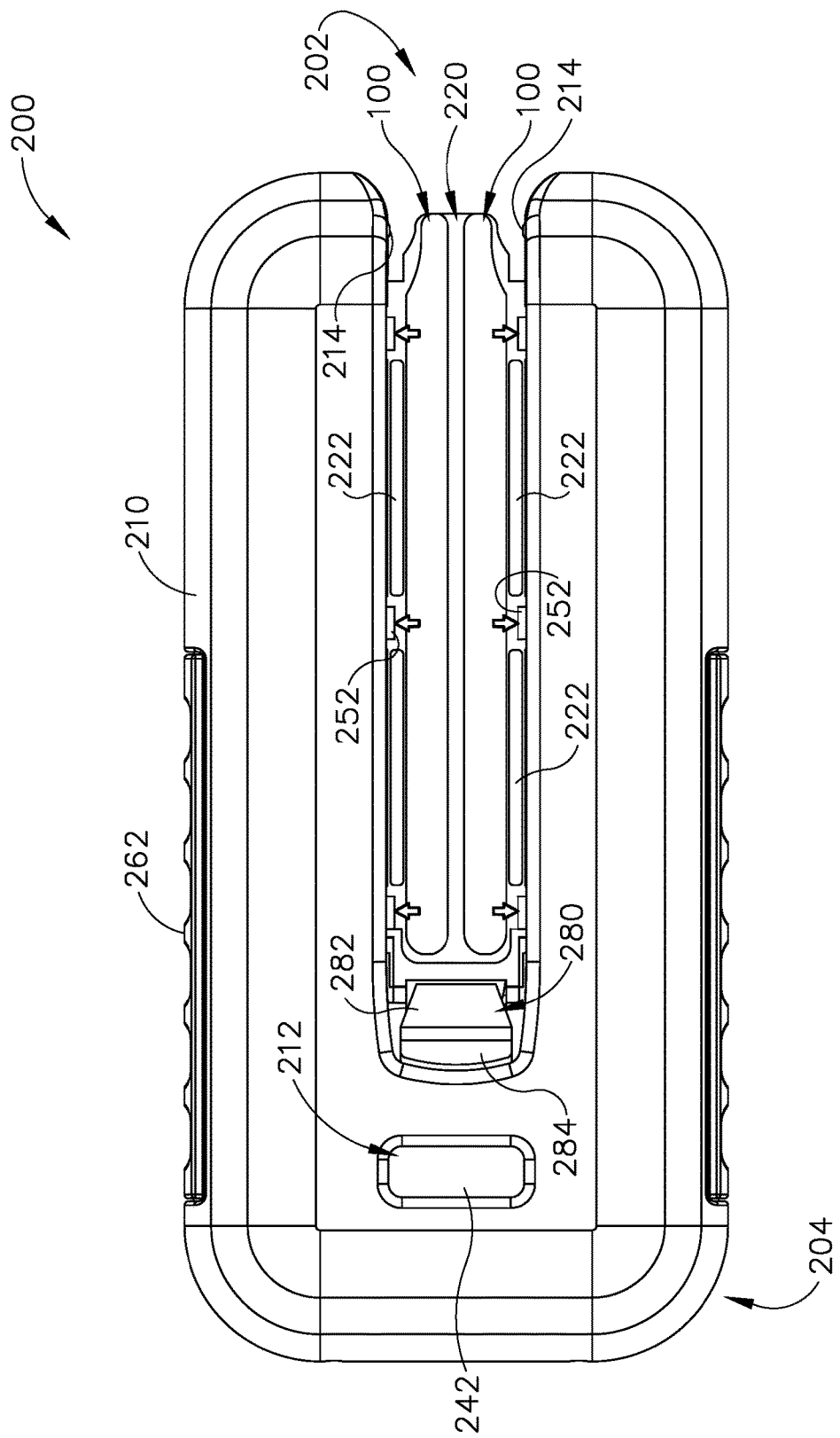
FIG. 14B depicts a top plan view of the buttress applier cartridge of FIG. 7, with a buttress assembly loaded on a platform of the buttress applier cartridge, and with retainers positioned to release the buttress assembly to the platform.

As shown in FIG. 10, sled retainer (280) includes a pair of arms (281) that together generally define a "U" shape. The free end of each arm (281) includes a tapered cam surface (282) and a housing engagement feature (284). As best seen in FIGS. 8 and 14A-14B, housing engagement features (284) are positioned to engage corresponding surfaces of housings (210, 218). Each arm (281) further includes a respective locking ridge (286) spaced proximally from the corresponding housing engagement feature (284). Sled retainer (280) further defines a channel (288) in the region where arms (281) meet each other. As shown in FIG. 9, channel (288) is configured to receive the proximal end of chassis (260).

Figure 16A:
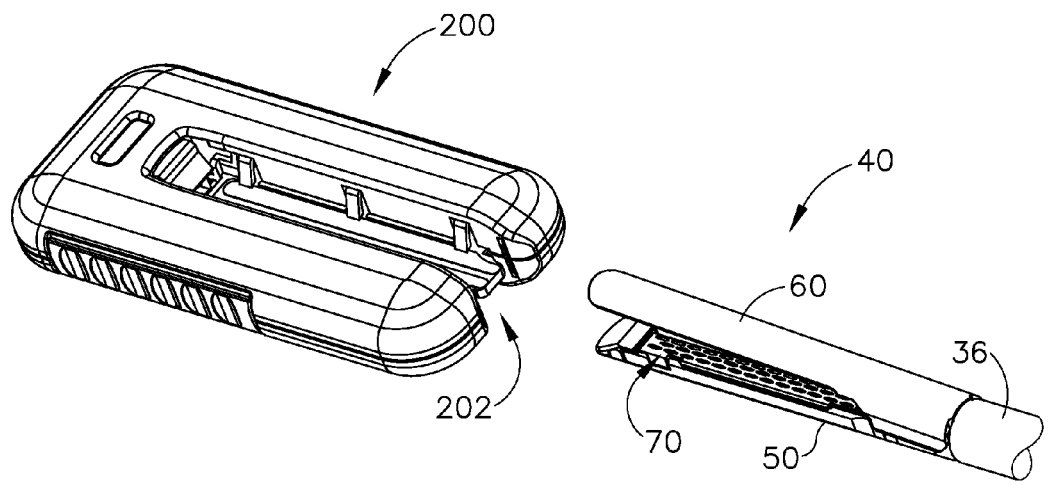
FIG. 16A depicts a perspective view of the end effector of FIG. 2 and the buttress applier cartridge of FIG. 7, with the end effector approaching the buttress applier cartridge.
Figure 16B:
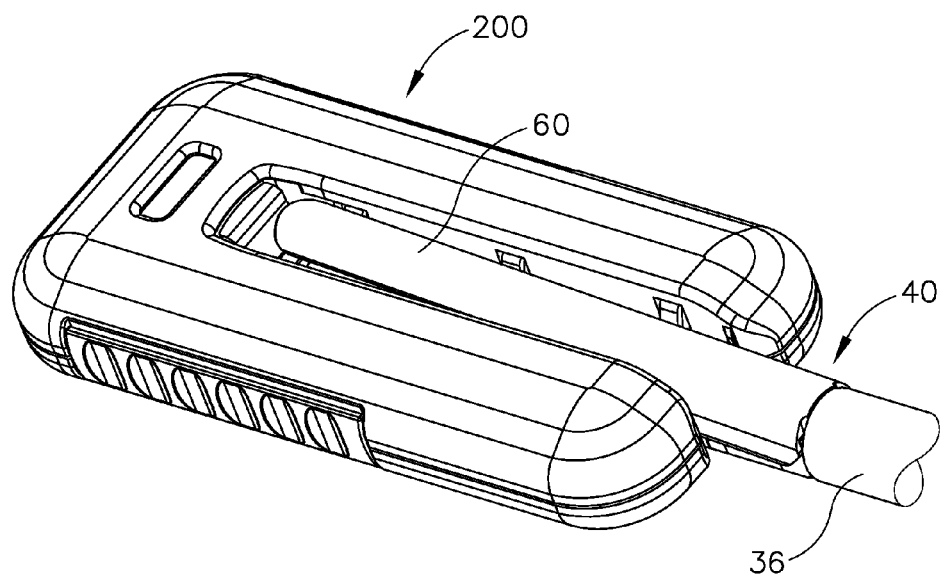
FIG. 16B depicts a perspective view of the end effector of FIG. 2 and the buttress applier cartridge of FIG. 7, with the buttress applier cartridge positioned in the end effector.
Figure 17A:
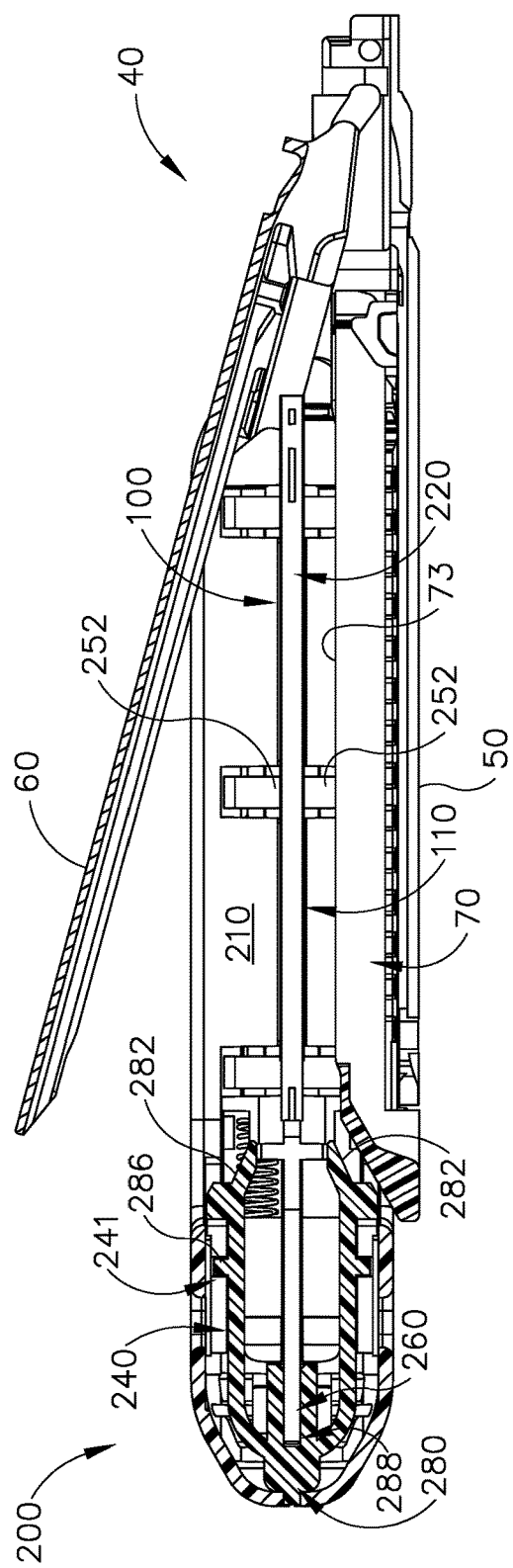
FIG. 17A depicts a cross-sectional side view of the end effector of FIG. 2 and the buttress applier cartridge of FIG. 7, with the buttress applier cartridge positioned in the end effector, and with the end effector in an open configuration.
Figure 17B:
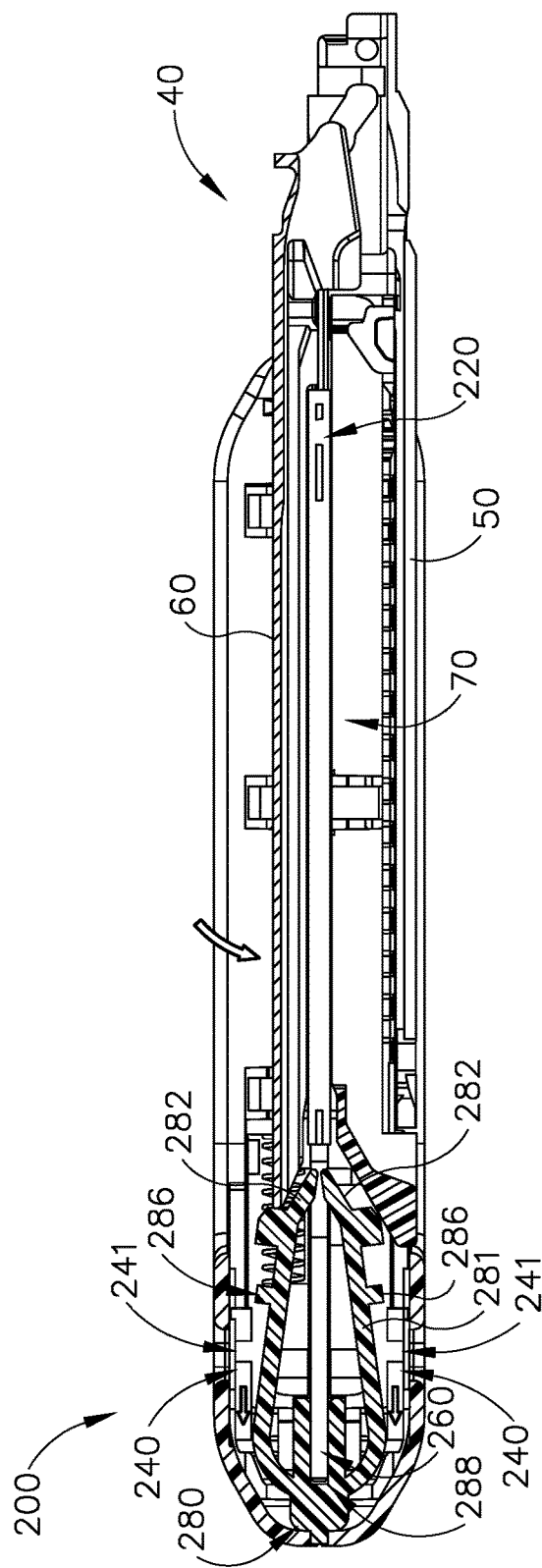
FIG. 17B depicts a cross-sectional side view of the end effector of FIG. 2 and the buttress applier cartridge of FIG. 7, with the buttress applier cartridge positioned in the end effector, and with the end effector in a closed configuration.

FIGS. 14A-17B show cartridge (200) in different stages of operation. In particular, FIGS. 14A, 15A, and 17A show cartridge (200) in a configuration where retainer arms (252) are positioned to hold buttress assemblies (100, 110) against platform (220); while FIGS. 14B, 15B, and 17B show cartridge (200) in a configuration where retainer arms (252) are positioned to release buttress assemblies (100, 110) from platform (220). While FIGS. 14A-17B only show buttress assembly (100) on platform (220), it should be understood that buttress assembly (110) would be retained on and released from platform (220) in an identical fashion.

To use cartridge (200) to load end effector (40), the operator would first position cartridge (200) and end effector (40) such that end effector is aligned with open end (202) of cartridge (200) as shown in FIG. 16A. The operator would then advance end effector (40) distally (and/or retract cartridge (200) proximally) to position platform (220) and buttress assemblies (100, 110) between anvil (60) and staple cartridge (70) as shown in FIG. 16B. This will ultimately result in the arrangement shown in FIG. 17A. While end effector (40) is not shown in FIG. 14A or 15A, it should be understood that cartridge (200) is in the same state in FIG. 17A as the state shown in FIGS. 14A and 15A. In this state, actuator sleds (240) are in a first longitudinal position (i.e., closer to open end (202)). Coil springs (298) are resiliently urging actuator sleds (240) toward a second longitudinal position (i.e., closer to closed end (204)). However, as best seen in FIG. 17A, locking ridges (286) of sled retainer (280) are disposed in locking recesses (241) of actuator sleds (240), thereby holding actuator sleds (240) in the first longitudinal position. With actuator sleds (240) in the first longitudinal position, retainers (250) are located at inward positions to retain buttress assemblies (100, 110) against platform (220). As shown in FIG. 15A, at this stage, pins (296) are positioned at the inner ends of slots (264) of chassis (260); and in the ends of obliquely extending portions (248) of slots (244).

In order to load buttress assemblies (100, 110) on end effector (40), the operator may simply close end effector (40) by pivoting anvil (60) toward staple cartridge (70), as described above, to reach the state shown in FIG. 17B. As shown, closure of end effector (40) results in the distal ends of anvil (60) and staple cartridge (70) bearing against cam surfaces (282) of sled retainer (280). This causes arms (281) of sled retainer to deform toward each other, such that locking ridges (286) disengage locking recesses (241) of actuator sleds (240). With locking ridges (286) disengaged from locking recesses (241) of actuator sleds (240), coil springs (298) drive actuator sleds (240) proximally to the second longitudinal position. Actuator sleds (240) engage bosses (268) of chassis (260) when actuator sleds (240) reach the proximal position, such that bosses (268) provide a hard stop. It should be understood that this sudden engagement between actuator sleds (240) and bosses (268) may produce a click or snap sound, providing audible feedback to the operator indicating actuation of cartridge (200).

In the present example, cartridge (200) is configured such that both arms (281) must be deformed toward each other at the same time in order for actuator sleds (240) to be unlocked and thereby permitted to translate proximally to the second longitudinal position. If only one arm (281) is deformed toward the other arm (281), the locking ridge (286) of the non-deformed arm (281) will remain disposed in the corresponding locking recess (241) of actuator sled (240), thereby continuing to hold actuator sled (240) in the first longitudinal position. By requiring both arms (281) to be deformed toward each other at the same time in order for actuator sleds (240) to be unlocked, the configuration of sled retainer (280) will reduce the risk of cartridge (200) being actuated prematurely or inadvertently.

As best seen in the transition from the view shown in FIG. 15A (actuator sleds (240) in the first longitudinal position) to the view shown in FIG. 15B (actuator sleds (240) in the second longitudinal position), slots (244) act as cams against pins (296) and thereby drive retainers (250) outwardly as actuator sleds (240) travel proximally. In particular, pins (296) traverse obliquely extending portions (248) of slots (244) and then longitudinally extending portions (246) of slots (244). Obliquely extending portions (248) of slots (244) drive pins (296) outwardly during this range of travel. Since retainers (250) travel unitarily with pins (296), retainers (250) travel outwardly as well. Laterally oriented slots (264) of chassis (260) accommodate the outward lateral movement of pins (296) but prevent pins (296) from moving longitudinally during the transition from the state shown in FIG. 15A to the state shown in FIG. 15B.

Upon reaching the state shown in FIG. 15B, retainers (250) are disengaged from buttress assemblies (100, 110). This state is also shown in FIG. 14B. It should be understood that end effector (40) is still in the closed configuration at this stage, as also shown in FIG. 17B. Thus, with end effector (40) clamping on both buttress assemblies (100, 110), adhesive layers (104, 114) are adhered to underside (65) of anvil (60) and deck (73) of staple cartridge (70). End effector (40) may then be re-opened (i.e., pivoting anvil (60) away from staple cartridge (70)) and pulled away from cartridge (200). With retainers (250) disengaged from buttress assemblies (100, 110), end effector (40) may freely pull buttress assemblies (100, 110) away from platform (220) as end effector (40) is pulled away from cartridge (200). With buttress assemblies (100, 110) loaded on end effector (40), end effector (40) may then be used as described above with reference to FIGS. 5A-6.

Referring back to FIGS. 7-8, housings (210, 218) of the present example include proximal guide features (214) and distal guide features (216). Guide features (214, 216) are configured to assist in providing proper alignment of end effector (40) with cartridge (200). In particular, guide features (214, 216) are configured to engage the lateral sides of lower jaw (50) and anvil (60) to ensure that the central longitudinal axis of end effector (40) is coplanar with the central longitudinal axis of platform (220). Such alignment will prevent buttress assemblies (100, 110) from being applied to underside (65) or deck (73) in a skewed orientation. In some versions, guide features (214, 216) engage the lateral sides of lower jaw (50) and anvil (60) as soon as end effector (40) is positioned as shown in FIG. 16B (i.e., before anvil (60) is pivoted to the closed position). In some other versions, guide features (214, 216) do not engage the lateral sides of lower jaw (50) and anvil (60) until anvil (60) is pivoted closer to the closed position. In the present example, guide features (214, 216) are unitarily formed features of housings (210, 218). In some other versions, guide features (214, 216) are movable relative to housings (210, 218) and are resiliently biased to provide self-centering guidance to the lateral sides of lower jaw (50) and anvil (60). Various suitable forms that guide features (214, 216) may take will be apparent to those of ordinary skill in the art in view of the teachings herein.

As noted above, indicator plates (242) may include different colored regions or other markings (e.g., text, pictograms, etc.) that provide visual indication through windows (212), visually indicating whether actuator sleds (240) are in the first longitudinal position (FIG. 15A) or the second longitudinal position (FIG. 15B). The operator may thus view indicator plate (242) through window (212) to determine whether cartridge (200) has successfully released buttress assemblies (100, 110). An operator may also view indicator plate (242) through window (212) to determine whether cartridge (200) has been previously used. Various suitable markings that may be provided on indicator plates (242) to provide visual feedback indicating the state of cartridge (200) will be apparent to those of ordinary skill in the art in view of the teachings herein.

B. Exemplary Buttress Applier Cartridge with Passive Retainer Arms

Figure 18:
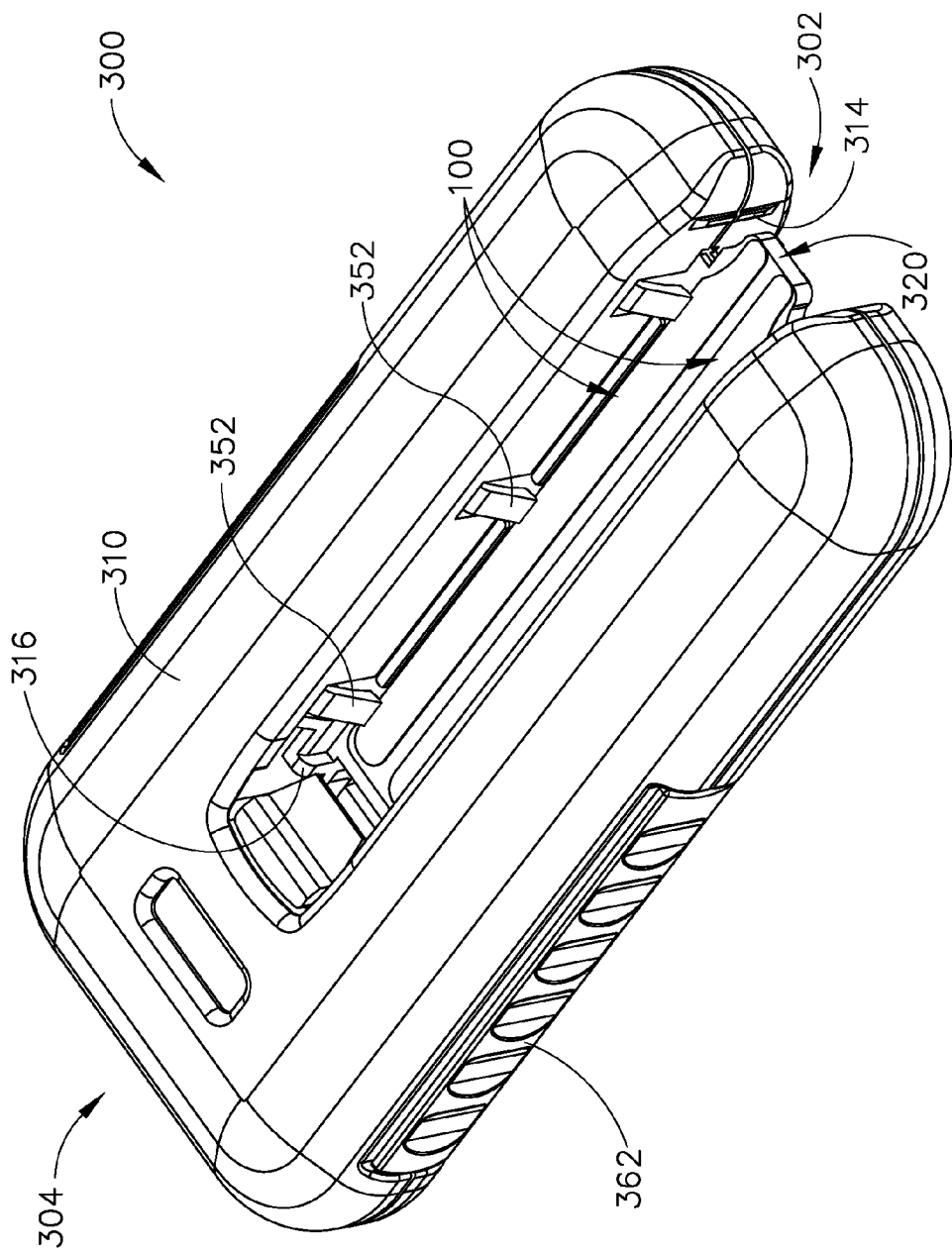
FIG. 18 depicts a perspective view of another exemplary buttress applier cartridge that may be used to carry and apply the buttress assembly of FIG. 5A.
Figure 19:
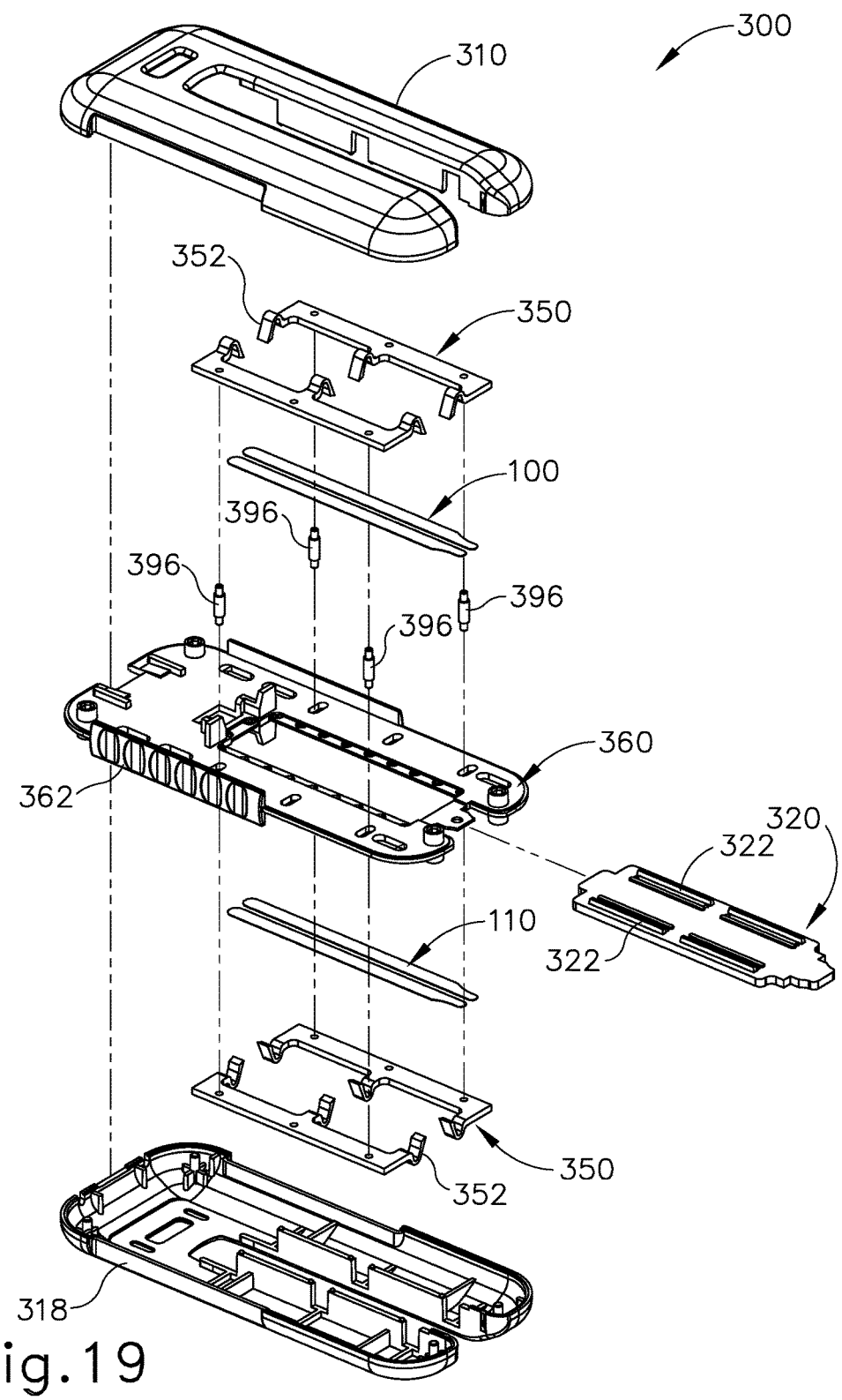
FIG. 19 depicts an exploded perspective view of the buttress applier cartridge of FIG. 18.

FIGS. 18-19 show another exemplary buttress applier cartridge (300) that may be used to support and protect buttress assemblies (100, 110). Cartridge (300) may also be used to easily load buttress assemblies (100, 110) on end effector (40). As best seen in FIG. 18, cartridge (300) of this example comprises an open end (302) and a closed end (304). Open end (302) is configured to receive end effector (40) as described above. Cartridge (300) further includes a first housing (310) and a second housing (318), which each generally define a "U" shape to present open end (302). As best seen in FIG. 19, various components are interposed between housings (310, 318). In particular, these components include a platform (320), a pair of retainers (350), and a chassis (360). Each of these components will be described in greater detail below.

Housings (310, 318) are configured substantially identically to housings (210, 218) described above. For instance, housings (310, 318) include guide features (314, 316) just like guide features (214, 216) described above. However, housings (310, 318) lack windows (212). Platform (320) of this example is identical to platform (220) described above, including the presence of retention features (322) in the form of ridges that further engage housings (310, 318) to prevent platform (320) from sliding relative to housings (310, 318). Chassis (360) is also identical to chassis (260), including the presence of integral gripping features (362) like gripping features (262) described above. Chassis (360) also includes laterally oriented slots just like slots (264) of chassis (260).

Retainers (350) are substantially similar to retainers (250). Retainers (350) are coupled together via pins (396), which are slidably disposed in the laterally oriented slots of chassis (360). Pins (396) provide coordinated lateral movement of retainers (350). In particular, the retainers (350) that are coupled together via pins (396) will move laterally in unison with each other. Retainers (350) include resilient retention arms (352). Arms (352) are similar to arms (252) in that arms (352) will effectively pinch buttress assemblies (100, 110) against platform (320) with a resilient bias.

When cartridge (300) is positioned relative to end effector (40) in an arrangement similar to that shown in FIG. 16B, and then end effector (40) is closed about platform (320) to reach an arrangement similar to that shown in FIG. 17B, anvil (60) and staple cartridge (70) will bear against corresponding surfaces of arms (352) and thereby cause arms (352) to slide laterally outwardly. Arms (352) will thus disengage buttress assemblies (100, 110) and thereby release buttress assemblies (100, 110) from platform (320). Underside (65) of anvil (60) will press against adhesive layer (104) of buttress assembly (100) and thereby adhere buttress assembly (100) to anvil (60). Similarly, deck (73) of staple cartridge (70) will press against adhesive layer (114) of buttress assembly (110) and thereby adhere buttress assembly (110) to staple cartridge (70). With buttress assemblies (100, 110) released from platform (320) and adhered to end effector (40), end effector (40) may be transitioned back to the open configuration and pulled away from cartridge (300). End effector (40) may then be used in a surgical procedure with buttress assemblies (100, 110) loaded thereon.

It should be understood that retainers (350) may remain located at laterally outward positions after releasing buttress assemblies (100, 110) from platform (320). For instance, the free ends of arms (352) may be bearing into corresponding surfaces of platform (320) providing friction that substantially maintains the positioning of retainers (350) relative to platform (320). An operator may visually observe the laterally outward positioning of retainers (350) and may thereby conclude that cartridge (300) has released buttress assemblies (100, 110). Alternatively, cartridge (300) may include various other kinds of features to provide visual feedback (and/or other feedback) indicating the state of cartridge (300).

In some alternative versions, arms (352) deform outwardly (instead of sliding outwardly) in order to release buttress assemblies (100, 110) in response to closure of end effector (40) about platform (320). In still other versions, arms (352) do not deform or translate outwardly in response to closure of end effector (40) about platform (320). Instead, the adhesion resulting from engagement between underside (65) of anvil (60) with adhesive surface (104) of buttress assembly (100), and the adhesion resulting from engagement between deck (73) of staple cartridge (73) with adhesive surface (114) of buttress assembly (110), will provide a secure engagement between buttress assemblies (100, 110) and end effector (40). This adhesive engagement may be secure enough to enable end effector (40) to pull buttress assemblies (100, 110) away from the free ends of arms (352) without damaging buttress assemblies (100, 110) or otherwise compromising the positioning of buttress assemblies (100, 110) on end effector (40), while arms (352) maintain the configuration and positioning shown in FIG. 18.

C. Exemplary Buttress Applier Cartridge with Passive Retaining Housing Features

Figure 20:
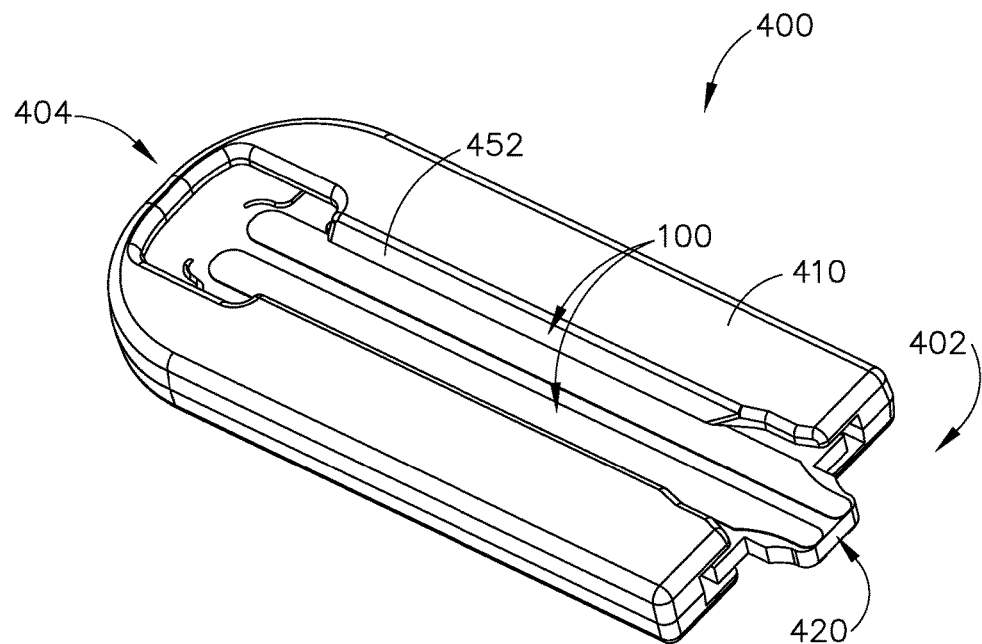
FIG. 20 depicts a perspective view of another exemplary buttress applier cartridge that may be used to carry and apply the buttress assembly of FIG. 5A.
Figure 21:
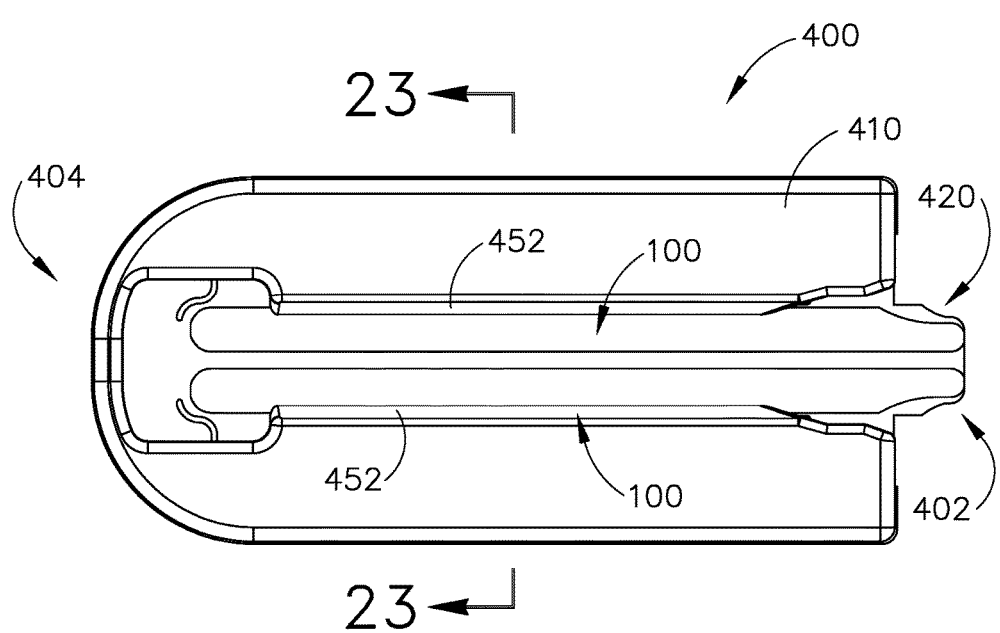
FIG. 21 depicts a top plan view of the buttress applier cartridge of FIG. 20.
Figure 22:
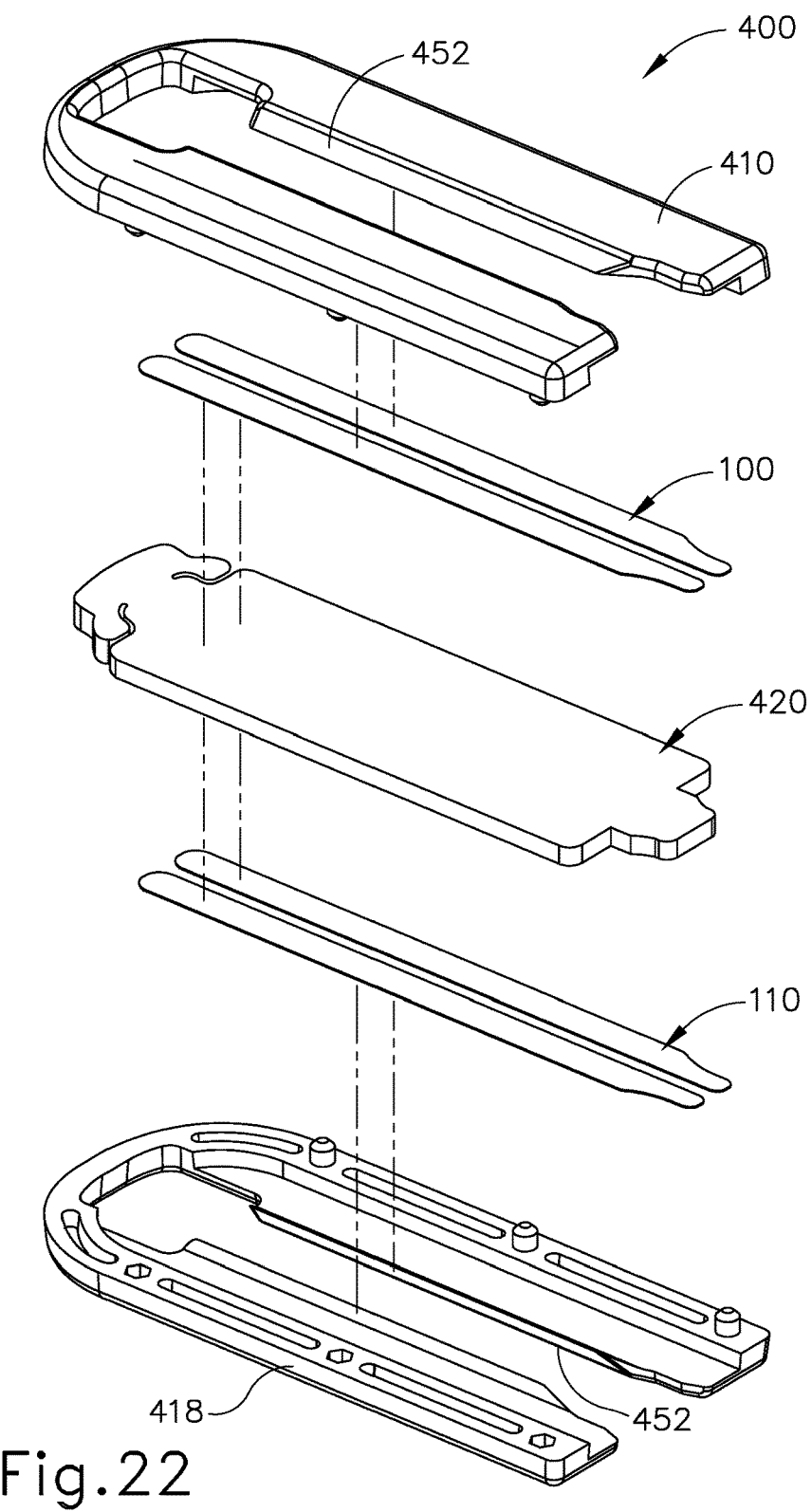
FIG. 22 depicts an exploded perspective view of the buttress applier cartridge of FIG. 20.

FIGS. 20-23 show another exemplary buttress applier cartridge (400) that may be used to support and protect buttress assemblies (100, 110). Cartridge (400) may also be used to easily load buttress assemblies (100, 110) on end effector (40). As best seen in FIG. 20-21, cartridge (400) of this example comprises an open end (402) and a closed end (404). Open end (402) is configured to receive end effector (40) as described above. Cartridge (400) further includes a first housing (410) and a second housing (418), which each generally define a "U" shape to present open end (402). As best seen in FIG. 22, a platform (420) is interposed between housings (410, 418).

Figure 23:
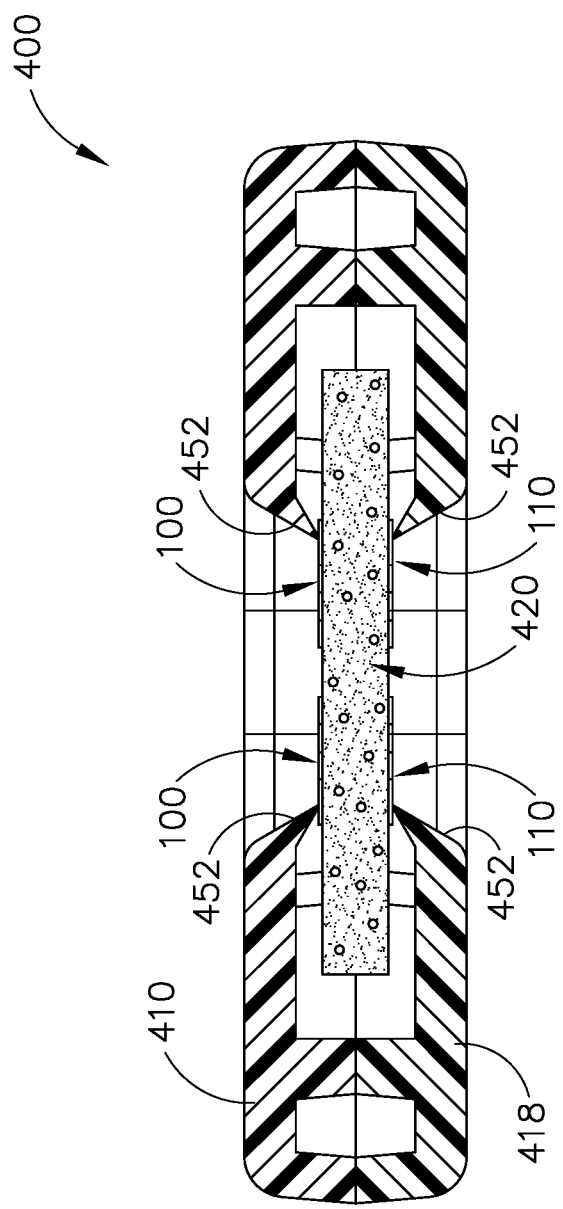
FIG. 23 depicts a cross-sectional view of the applier cartridge of FIG. 20, taken along line 23-23 of FIG. 21.

Each housing (410, 418) of the present example comprises an integral retention fin (452). Fins (452) extend longitudinally along substantial portions of the lengths of corresponding buttress assemblies (100, 110). As best seen in FIG. 23, retention fins (452) of housing (410) secure buttress assembly (100) to platform (420); while retention fins (452) of housing (418) secure buttress assembly (110) to platform (420). At least a portion of each housing (410, 418) may comprise a resilient material such that retention fins (452) resiliently bear against corresponding buttress assemblies (100, 110). In addition or in the alternative, platform (420) may comprise a resilient material that is biased to expand outwardly, such that platform (420) bears buttress assemblies (100, 110) against corresponding retention fins (452). Various suitable materials that may be used to form housings (410, 418) and platform (420) will be apparent to those of ordinary skill in the art in view of the teachings herein.

When cartridge (400) is positioned relative to end effector (40) in an arrangement similar to that shown in FIG. 16B, and then end effector (40) is closed about platform (420) to reach an arrangement similar to that shown in FIG. 17B, anvil (60) and staple cartridge (70) will bear against corresponding surfaces of retention fins (452) and thereby cause retention fins (452) to deform laterally outwardly. Retention fins (452) will thus disengage buttress assemblies (100, 110) and thereby release buttress assemblies (100, 110) from platform (420). Underside (65) of anvil (60) will press against adhesive layer (104) of buttress assembly (100) and thereby adhere buttress assembly (100) to anvil (60). Similarly, deck (73) of staple cartridge (70) will press against adhesive layer (114) of buttress assembly (110) and thereby adhere buttress assembly (110) to staple cartridge (70). With buttress assemblies (100, 110) released from platform (420) and adhered to end effector (40), end effector (40) may be transitioned back to the open configuration and pulled away from cartridge (400). End effector (40) may then be used in a surgical procedure with buttress assemblies (100, 110) loaded thereon.

In some other versions, retention fins (452) do not deform or translate outwardly in response to closure of end effector (40) about platform (320). Instead, the adhesion resulting from engagement between underside (65) of anvil (60) with adhesive surface (104) of buttress assembly (100), and the adhesion resulting from engagement between deck (73) of staple cartridge (73) with adhesive surface (114) of buttress assembly (110), will provide a secure engagement between buttress assemblies (100, 110) and end effector (40). This adhesive engagement may be secure enough to enable end effector (40) to pull buttress assemblies (100, 110) away from retention fins (452) without damaging buttress assemblies (100, 110) or otherwise compromising the positioning of buttress assemblies (100, 110) on end effector (40), while retention fins (452) maintain the configuration and positioning shown in FIGS. 20-21 and 23.

IV. Exemplary Alternative Platforms for Buttress Applier Cartridges

In the examples above, platforms (220, 320, 420) are provided as generally flat, stationary members that simply provide support to buttress assemblies (100, 110) until buttress assemblies (100, 110) are adhered to end effector (40). It may be desirable to provide additional functionality to platform (220, 320, 420). For instance, it may be desirable to enable platform (220, 320, 420) to slide relative to housings (210, 218, 310, 318, 410, 418). For instance, when the operator clamps down on buttress assemblies (100, 110) and platform (220, 320, 420) with end effector (40), the operator may wish to pull platform (220, 320, 420) toward the operator, through open end (202, 302, 402), with end effector (40) still clamped down on buttress assemblies (100, 110) and platform (220, 320, 420). This may further promote removal of buttress assemblies (100, 110) from platform (220, 320, 420) and/or enable the operator to more readily confirm visually that buttress assemblies (100, 110) have been removed from platform (220, 320, 420). Several merely illustrative variations of platform (220, 320, 420) will be described in greater detail below. Further variations will be apparent to those of ordinary skill in the art in view of the teachings herein.

Figure 24:
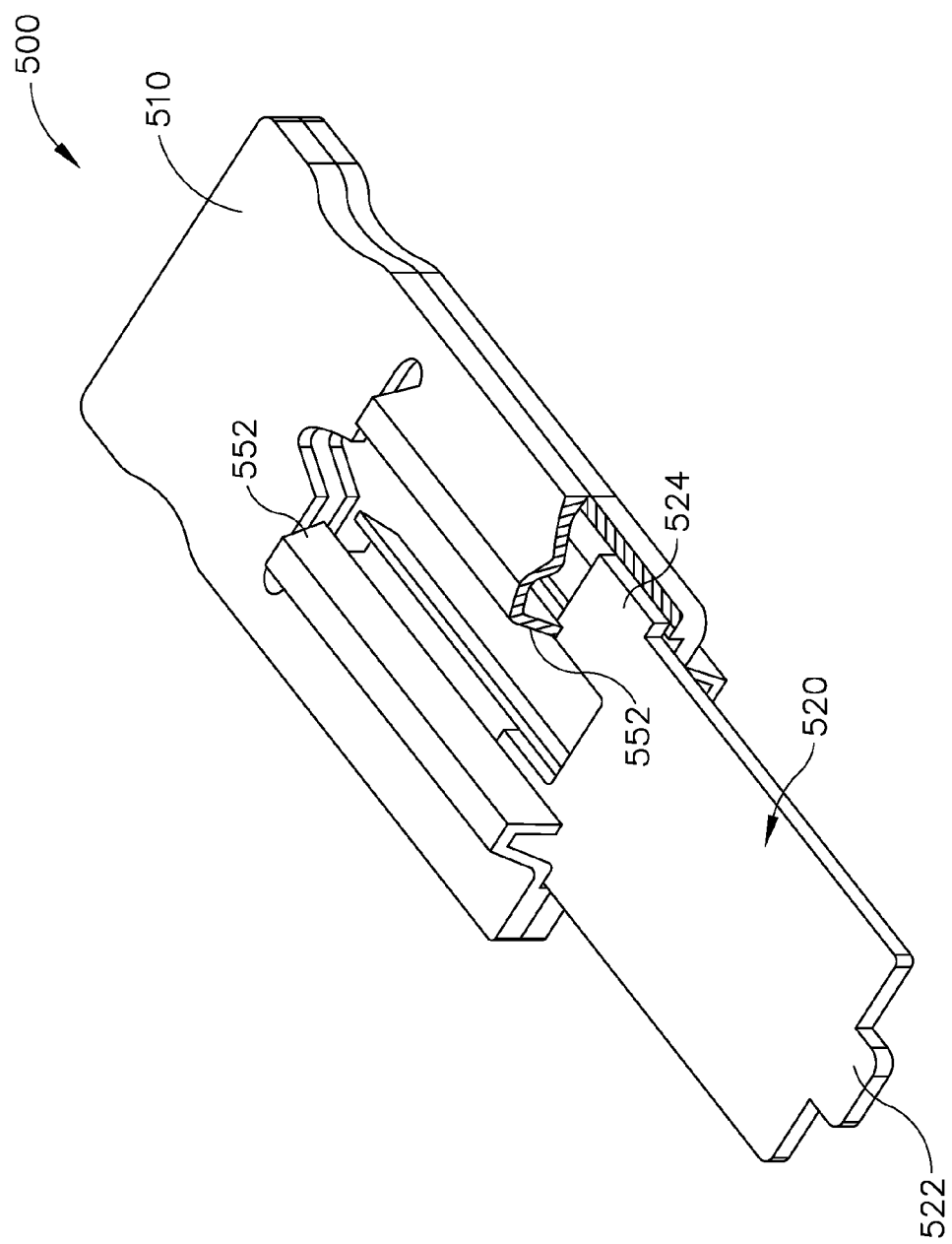
FIG. 24 depicts a perspective view of another exemplary buttress applier cartridge that may be used to carry and apply the buttress assembly of FIG. 5A, with a sliding platform in an extended position.

FIG. 24 shows an exemplary alternative buttress applier cartridge (500) that may be used to support and protect buttress assemblies (100, 110). Cartridge (500) may also be used to easily load buttress assemblies (100, 110) on end effector (40). Cartridge (500) of this example includes a housing (510) and a platform (520). Housing (510) of the present example comprises a pair of longitudinally extending retention fins (552) that are configured to releasably secure buttress assemblies (100, 110) to platform (520) just like retention fins (452) described above. It should be understood that fins (552) are provided by way of example only; and that cartridge (500) may instead include any other suitable kinds of buttress assembly (100, 110) retention features, including but not limited to those described elsewhere herein.

Platform (520) of the present example includes a longitudinally projecting tongue (522) and a pair of outwardly extending tabs (524). Tongue (522) is located at one end of platform (520) while tabs (524) are located at the other end of platform (520). While buttress assemblies (100, 110) are not shown in FIG. 24, it should be understood that platform (520) may receive and hold buttress assemblies (100, 110) just like platforms (220, 320, 420) described above.

In the present example, platform (520) is configured to slide longitudinally relative to housing (510). In particular, when an operator clamps down on buttress assemblies (100, 110) and platform (520) with end effector (40), the operator may pull platform (520) toward the operator, with end effector (40) still clamped down on buttress assemblies (100, 110) and platform (520) until platform (520) is translated to the position shown in FIG. 24. At this stage, tabs (524) engage the end of housing (510) and thereby prevent platform (520) from translating further. The operator may then release platform (520) by transitioning end effector (40) back to the open position, carrying away buttress assemblies (100, 110) on end effector (40).

In the present example, fins (552) cooperate to slightly compress platform (520), providing friction that prevents platform (520) from inadvertently translating to the advanced position shown in FIG. 24. However, the compression exerted by fins (552) on platform (520) still enables platform (520) to be pulled to the advanced position shown in FIG. 24, as described above, without tearing platform (520). It should also be understood that the friction provided by fins (552) against platform (520) may substantially hold platform (520) in the advanced position shown in FIG. 24.

Figure 25A:
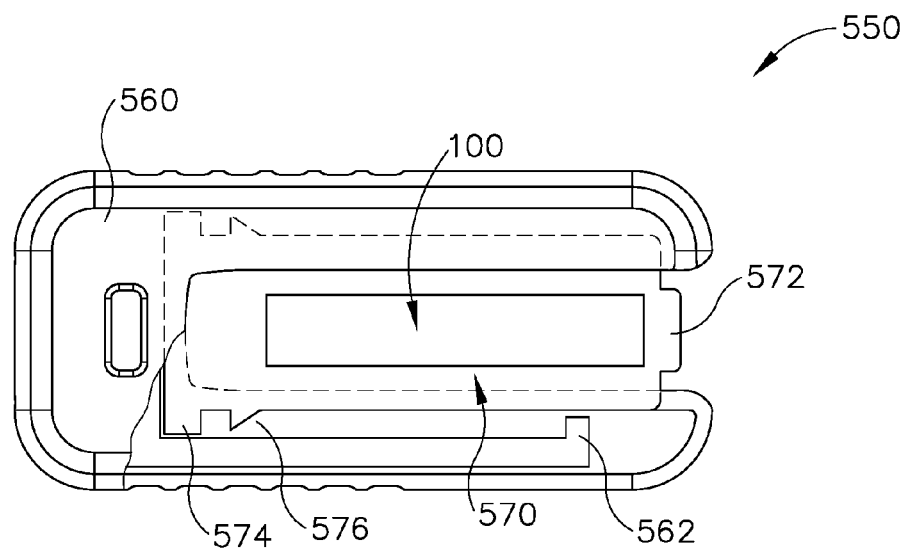
FIG. 25A depicts a top plan view of another exemplary buttress applier cartridge that may be used to carry and apply the buttress assembly of FIG. 5A, with a portion of the housing broken away to reveal internal features, and with a sliding platform in a retracted position.
Figure 25B:
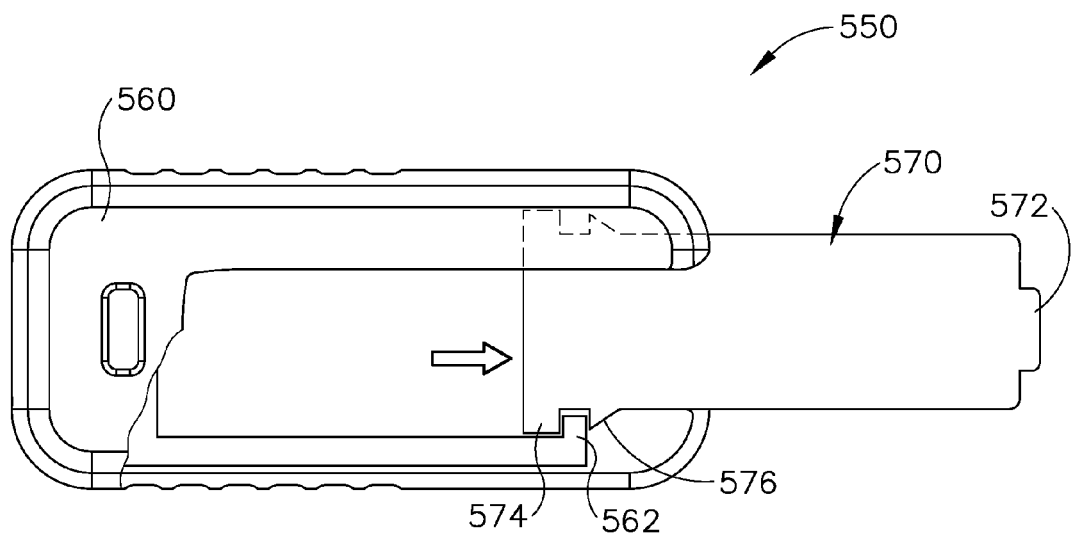
FIG. 25B depicts a top plan view of the buttress applier cartridge of FIG. 25A, with a portion of the housing broken away to reveal internal features, and with the sliding platform in an extended position.

It may be desirable to rely on more than just friction to hold a sliding platform in an advanced position. FIGS. 25A-25B show another exemplary alternative buttress applier cartridge (550) that may be used to support and protect buttress assemblies (100, 110) on a platform (570) that may be secured in an advanced position. Cartridge (550) may also be used to easily load buttress assemblies (100, 110) on end effector (40). Cartridge (550) of this example includes a housing (560) and platform (570). While not shown, cartridge (550) may include retention fins and/or any other suitable kinds of buttress assembly (100, 110) retention features, including but not limited to those described elsewhere herein.

Platform (570) of the present example includes a longitudinally projecting tongue (572), a pair of outwardly extending tabs (574), and a pair of outwardly extending locking pawls (576). Tongue (572) is located at one end of platform (570) while tabs (574) are located at the other end of platform (570). While buttress assemblies (100, 110) are not shown in FIGS. 25A-25B, it should be understood that platform (570) may receive and hold buttress assemblies (100, 110) just like platforms (220, 320, 420) described above.

In the present example, platform (570) is configured to slide longitudinally relative to housing (510). In particular, when an operator clamps down on buttress assemblies (100, 110) and platform (570) with end effector (40), the operator may pull platform (570) toward the operator, with end effector (40) still clamped down on buttress assemblies (100, 110) and platform (570) until platform (570) is translated from the position shown in FIG. 25A to the position shown in FIG. 25B. At this stage, tabs (574) engage inwardly extending bosses (562) of housing (560), which thereby prevent platform (570) from translating further. In addition, pawls (576) engage bosses (562) to prevent platform (570) from translating back to the retracted position. It should be understood that pawls (576) may deform inwardly as platform (570) translates from the position shown in FIG. 25A to the position shown in FIG. 25B. Once platform (570) has reached the position shown in FIG. 25B, the operator may then release platform (570) by transitioning end effector (40) back to the open position, carrying away buttress assemblies (100, 110) on end effector (40).

It should be understood that either of the slidable platforms (520, 570) described above may be readily incorporated into any of the cartridges (200, 300, 400) described above.

V. Exemplary Alternative Buttress Retention Features for Buttress Applier Cartridges As described above, a cartridge (200, 300, 400) may secure buttress assemblies (100, 110) to platform (220, 320, 420) using arms (252, 352) or fins (452). However, it will be understood that arms (252, 352) and fins (452) are merely illustrative examples of structures that may be used to secure buttress assemblies (100, 110) to platform (220, 320, 420). Several additional structures that may be used to secure buttress assemblies (100, 110) to platform (220, 320, 420) will be described in greater detail below, while still further examples will be apparent to those of ordinary skill in the art in view of the teachings herein. It should be understood that the following teachings may be readily incorporated into any of the various buttress applier cartridges described herein.

A. Exemplary Buttress Applier Cartridge with Ratcheting Retaining Arms

Figures 26A, 26B, 26C:
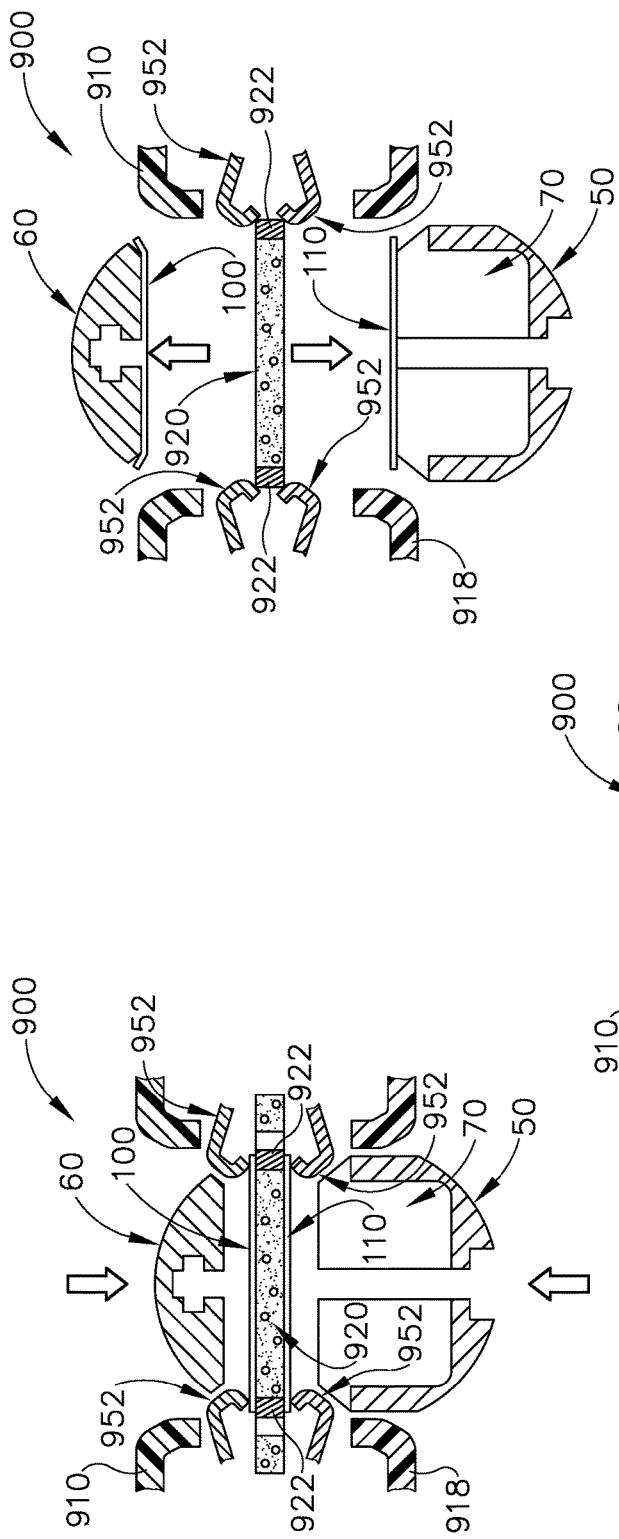
FIG. 26A depicts a partial, cross-sectional end view of another exemplary buttress applier cartridge positioned in the end effector of FIG. 2, with the end effector in a partially open configuration, and with ratcheting retention arms of the buttress applier cartridge in a buttress engaging configuration.
FIG. 26B depicts a partial, cross-sectional end view of the buttress applier cartridge of FIG. 26A positioned in the end effector of FIG. 2, with the end effector in a closed configuration, thereby driving the ratcheting retention arms to a buttress disengaging configuration.
FIG. 26C depicts a partial, cross-sectional end view of the buttress applier cartridge of FIG. 26A positioned in the end effector of FIG. 2, with the end effector in an open configuration, with the buttress assembly adhered to the end effector, and with the retention arms remaining in the buttress disengaging configuration.

FIGS. 26A-26C show another exemplary buttress applier cartridge (900) that may be used to support and protect buttress assemblies (100, 110). Cartridge (900) may also be used to easily load buttress assemblies (100, 110) on end effector (40). Cartridge (900) of this example includes housings (910, 918) and a platform (920). Platform (920) of this example is substantially identical to platforms (220, 320, 420) described above, except that platform (920) of this example includes rigid lateral edges (922) extending along the length of each longitudinally extending side of platform (920). Cartridge (900) of this example further includes ratcheting retainer arms (952). Arms (952) of this example are substantially similar to arms (352) of cartridge (300). However, unlike arms (352), arms (952) include ratcheting teeth (954) as best seen in FIGS. 27A-27B. Ratcheting teeth (954) are configured to engage rigid lateral edges (922) of platform (920) to hold arms (952) in a releasing position as described below.

FIGS. 26A and 27A show cartridge (900) in a state prior to engagement with end effector (40). At this stage, the free ends of arms (952) engage the lateral edges of buttress assemblies (100, 110) and thereby secure buttress assemblies (100, 110) to platform (920). In particular, the lateral edges of buttress assemblies (100, 110) are captured between the free ends of arms (952) and rigid lateral edges (922) of platform (920). In the present example, arms (952) are resiliently biased to bear against buttress assemblies (100, 110) to maintain this engagement and thereby secure buttress assemblies (100, 110) to platform (920).

FIGS. 26B and 27B show cartridge (900) as end effector (40) is clamping down on buttress assemblies (100, 110) and platform (920). As shown, the lateral edges of anvil (60) and staple cartridge (70) engage arms (952), thereby urging the upper set of arms (952) toward the lower set of arms (952). The resulting movement of arms (952) causes arms (952) to move outwardly away from buttress assemblies (100, 110), thereby disengaging buttress assemblies (100, 110). In addition, as best seen in FIG. 27B, this movement of arms (952) causes teeth (954) of arms (952) to ratchet along rigid lateral edges (922) of platform (920). As best seen in FIG. 26B, the intermediate region of platform (920) compresses while edges (922) of platform (920) do not compress during closure of end effector. This difference in compressibility across the width of platform (920) enables edges (922) to further urge the lateral edges of buttress assemblies (100, 110) into adhesive engagement with the chamfered lateral edges of anvil (60) and staple cartridge (70).

FIG. 26C shows cartridge (900) released from end effector (40). As shown, buttress assemblies (100, 110) are adhered to anvil (60) and staple cartridge (70), such that end effector (40) is ready for use in a surgical procedure as described above. In addition, arms (952) remain secured in a releasing position due to the engagement between teeth (954) of arms (952) with rigid lateral edges (922) of platform (920).

B. Exemplary Buttress Applier Cartridge with Multi-Buttress Layers

In some instances, it may be desirable to enable a single buttress applier cartridge to be used to apply several layers of buttress assemblies (100, 110) to an end effector (40) during a single surgical procedure. In other words, it may be desirable to enable an operator to use a cartridge to apply a first set of buttress assemblies (100, 110) to an end effector (40), use the end effector (40) to apply staples (90) and that first set of buttress assemblies (100, 110) to tissue, then use the same cartridge to apply a second set of buttress assemblies (100, 110) to the same end effector (40) (after staple cartridge (70) has been replaced), then use the same end effector (40) to apply staples (90) and that second set of buttress assemblies (100, 110) to tissue, and so on.

Figure 28:
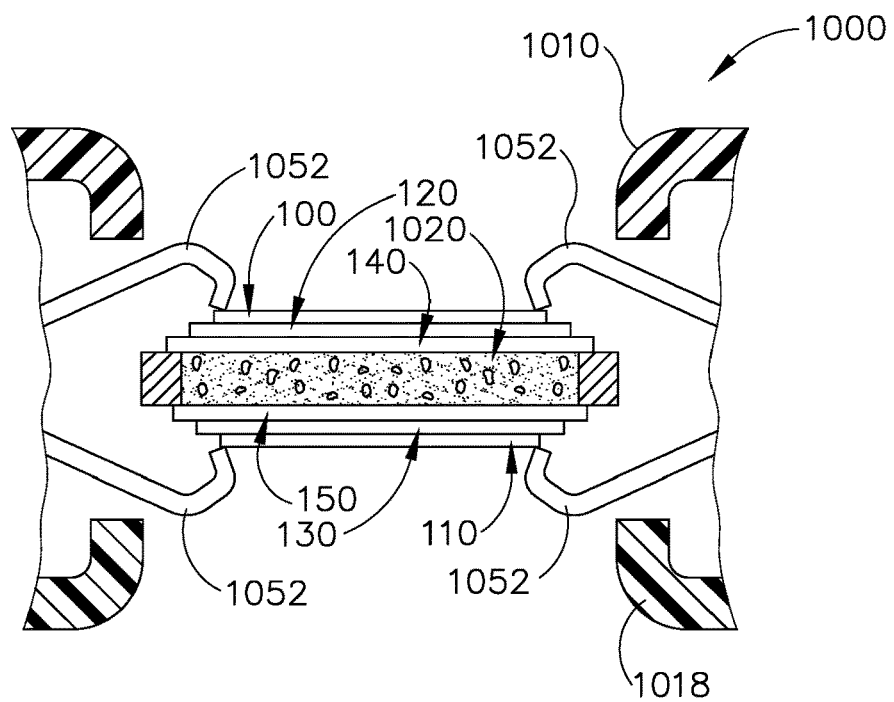
FIG. 28 depicts a partial, cross-sectional end view of another exemplary buttress applier cartridge, with a platform carrying a plurality of buttress assemblies, and with retainer arms in first positions.
Figure 29:
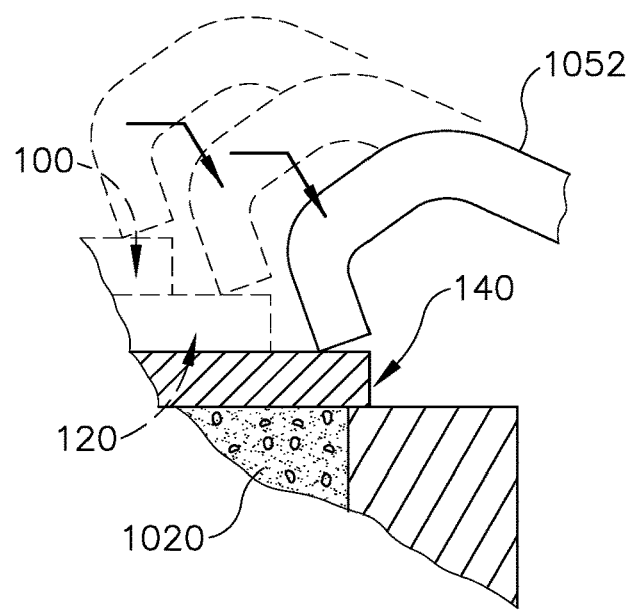
FIG. 29 depicts a partial, cross-sectional detail view of a retainer arm of the buttress applier cartridge transitioning from the first position to second and third positions.

FIGS. 28-29 show one merely illustrative way in which a single buttress applier cartridge to be used to apply several layers of buttress assemblies (100, 110) to an end effector (40) during a single surgical procedure. In particular, FIG. 28 shows an exemplary buttress applier cartridge (1000) that may be used to support and protect buttress assemblies (100, 110, 120, 130, 140, 150). Cartridge (1000) may also be used to easily load buttress assemblies (100, 110, 120, 130, 140, 150) on end effector (40). Cartridge (1000) of this example includes housings (1010, 1018), a platform (1020), and retainer arms (1052). Platform (1020) of this example is substantially identical to platforms (220, 320, 420) described above. Arms (1052) of this example are substantially similar to arms (352) of cartridge (300).

Cartridge (1000) of the present example differs from other buttress applier cartridges described herein in that cartridge (1000) includes several layers of buttress assemblies (100, 110, 120, 130, 140, 150) on each side of platform (1020). In particular, cartridge (1000) include three layers of buttress assemblies (100, 120, 140) on the upper surface of platform (1020); and three layers of buttress assemblies (110, 130, 150) on the lower surface of platform (1020). Buttress assemblies (100, 120, 140) are thus configured and positioned to engage underside (65) of anvil (50); while buttress assemblies (110, 130, 150) are configured and positioned to engage deck (73) of staple cartridge (70). In the present example, buttress assemblies (100, 120, 140) have a progressively increasing lateral width, such that the uppermost buttress assembly (100) has the narrowest width, the intermediate buttress assembly (120) has an intermediate width, and the lowermost buttress assembly (140) has the widest width. Similarly, buttress assemblies (110, 130, 150) have a progressively increasing lateral width, such that the lowermost buttress assembly (110) has the narrowest width, the intermediate buttress assembly (130) has an intermediate width, and the uppermost buttress assembly (150) has the widest width.

Arms (1052) are resiliently biased to bear against buttress assemblies (100, 110, 120, 130, 140, 150) to thereby secure buttress assemblies (100, 110, 120, 130, 140, 150) to platform (1020). When end effector (40) is clamped down on buttress assemblies (100, 110, 120, 130, 140, 150) and platform (1020) a first time, the lateral edges of anvil (60) and staple cartridge (70) engage arms (1052), thereby urging the upper set of arms (1052) toward the lower set of arms (1052). This causes arms (1052) to disengage buttress assemblies (100, 110) and directly engage buttress assemblies (120, 130); while buttress assemblies (100, 110) are adhered to anvil (60) and staple cartridge (70), respectively. When end effector (40) is subsequently opened, buttress assemblies (100, 110) remain adhered to anvil (60) and staple cartridge (70) and are thus pulled away from cartridge (1000), while buttress assemblies (120, 130, 140, 150) remain secured to platform (1020).

When end effector (40) is then clamped down on buttress assemblies (120, 130, 140, 150) and platform (1020) a second time (e.g., after end effector (40) has been actuated on tissue and reloaded with a new staple cartridge (70)), the lateral edges of anvil (60) and staple cartridge (70) engage arms (1052) again, thereby urging the upper set of arms (1052) toward the lower set of arms (1052) again. This causes arms (1052) to disengage buttress assemblies (120, 130) and directly engage buttress assemblies (140, 150); while buttress assemblies (120, 130) are adhered to anvil (60) and staple cartridge (70), respectively. When end effector (40) is subsequently opened, buttress assemblies (120, 130) remain adhered to anvil (60) and staple cartridge (70) and are thus pulled away from cartridge (1000), while buttress assemblies (140, 150) remain secured to platform (1020).

When end effector (40) is then clamped down on buttress assemblies (140, 150) and platform (1020) a third time (e.g., after end effector (40) has been actuated on tissue and reloaded with a new staple cartridge (70)), the lateral edges of anvil (60) and staple cartridge (70) engage arms (1052) again, thereby urging the upper set of arms (1052) toward the lower set of arms (1052) again. This causes arms (1052) to disengage buttress assemblies (140, 150) and directly engage platform (1020); while buttress assemblies (140, 150) are adhered to anvil (60) and staple cartridge (70), respectively. When end effector (40) is subsequently opened, buttress assemblies (140, 150) remain adhered to anvil (60) and staple cartridge (70) and are thus pulled away from cartridge (1000).

It should be understood from the foregoing that the varying widths of buttress assemblies (100, 110, 120, 130, 140, 150) enable arms (1052) to engage corresponding sets of buttress assemblies (100, 110, 120, 130, 140, 150) in a succession each time end effector (40) is closed upon buttress assemblies (100, 110, 120, 130, 140, 150) and platform (1020). This succession is best seen in FIG. 29. It should also be understood that any other suitable number of layers of buttress assemblies (100, 110, 120, 130, 140, 150) may be used.

VI. Exemplary Alternative Staple Cartridge with Integral Buttress

In the examples described above, a buttress assembly (110) is applied to a staple cartridge (70) by using a buttress applying cartridge right before end effector (40) will be actuated in a surgical procedure. In some instances, it may be desirable to provide a staple cartridge (70) that includes a buttress assembly (110) that is pre-loaded on deck (730). Such a pre-loaded buttress assembly (110) may be provided regardless of whether or not a buttress applying cartridge will be used to apply a buttress assembly (100) to underside (65) of anvil (60) right before end effector (40) will be actuated in a surgical procedure.

Figure 30:
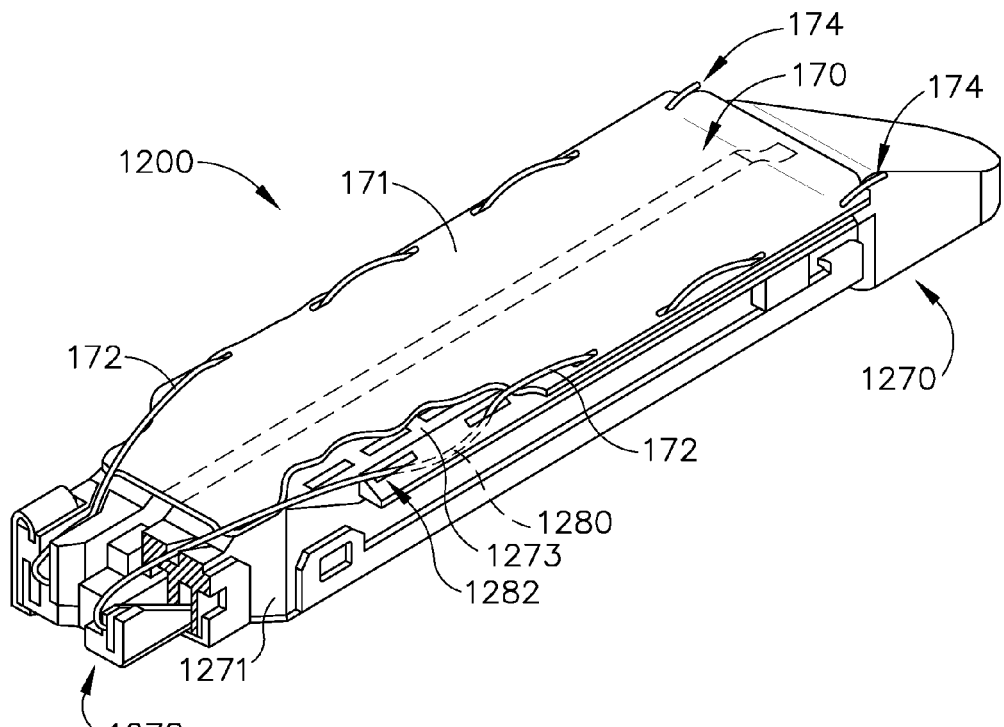
FIG. 30 depicts a perspective view of an exemplary alternative staple cartridge that may be loaded into the end effector of FIG. 2, with a buttress loaded thereon by a thread.

FIG. 30 shows an exemplary cartridge assembly (1200) that includes a modified staple cartridge (1270) pre-loaded with a buttress assembly (170). Staple cartridge (1270) of this example is substantially identical to staple cartridge (70) described above except that staple cartridge (1270) includes a pair of laterally extending engagement wings (1280) extending along the lateral sides of deck (1273). Wings (1280) define suture slots (1282) that are configured to receive corresponding strands of suture (172) as will be described below. Buttress assembly (170) includes a body (171) that is substantially identical to body (112) of buttress assembly (110) described above. In the present example, buttress assembly (170) lacks an adhesive layer like adhesive layer (114). In some other versions, buttress assembly (170) includes an adhesive layer to assist in securing buttress assembly (170) to deck (1273) of staple cartridge (1270).

In the present example, suture (172) is used to releasably secure buttress assembly (170) to staple cartridge (1270). Cartridge assembly (1200) includes two strands of suture (172), each strand being located at a respective lateral side of cartridge assembly (1200). As shown in FIG. 30 and FIG. 32A, each strand of suture (172) is woven through body (171) and suture slots (1282) of a corresponding wing (1280). The free end (174) of each suture (172) is positioned at the distal end of body (171) while the other end of each suture (172) is secured to wedge sled (1278) of staple cartridge (1270). Wedge sled (1278) of this example is configured and operable just like wedge sled (78) of staple cartridge (70).

Cartridge assembly (1200) may be loaded in lower jaw (50) just like staple cartridge (70), with buttress assembly (170) already secured to staple cartridge (1270). When staple cartridge (1270) is actuated to drive staples (90) through tissue as described above with respect to staple cartridge (70), wedge sled (1278) and suture (172) will cooperate to release buttress assembly (170) from staple cartridge (1270). In particular, as shown in FIG. 32B, wedge sled (1278) will pull suture (172) distally when wedge sled (1278) is driven distally as end effector (40) is actuated. Suture (172) will thus be pulled through body (171) and suture slots (1282) of wing (1280). In the present example, suture (172) has a length such that free end (174) of suture (172) will be pulled free of buttress assembly (170) when wedge sled (1278) reaches a distal-most position in response to full actuation of end effector (40). In some versions, suture (172) has a length such that free end (174) of suture (172) will be pulled into the interior of staple cartridge (1270) when wedge sled (1278) reaches a distal-most position in response to full actuation of end effector (40).

Figure 31:
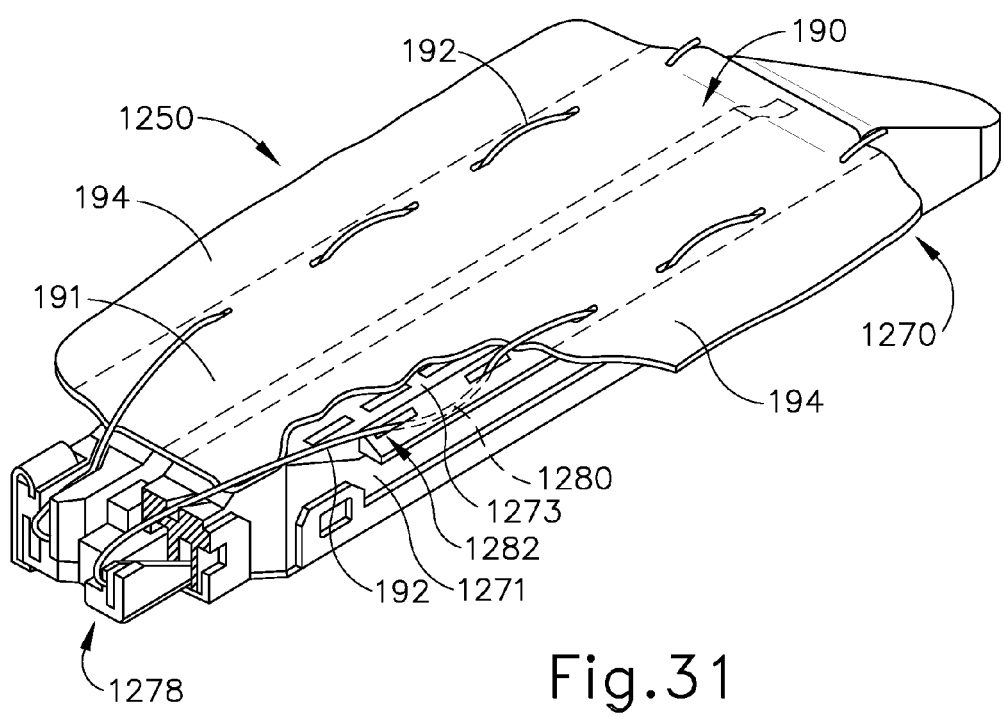
FIG. 31 depicts a perspective view of another exemplary alternative staple cartridge that may be loaded into the end effector of FIG. 2, with another buttress loaded thereon by a thread.

FIG. 31 shows another exemplary cartridge assembly (1250) that is a merely illustrative variation of cartridge assembly (1200) described above. Cartridge assembly (1200) of this example comprises the same staple cartridge (1270) pre-loaded with a different buttress assembly (190). Buttress assembly (190) includes a body (191) that is substantially identical to body (112) of buttress assembly (110) described above. Suture (192) is used to secure body (191) to staple cartridge (1270) in the same manner in which suture (172) is used to secure body (171) to staple cartridge (1270). In the present example, buttress assembly (190)

lacks an adhesive layer like adhesive layer (114). In some other versions, buttress assembly (190) includes an adhesive layer to assist in securing buttress assembly (190) to deck (1273) of staple cartridge (1270). The difference between buttress assembly (190) and buttress assembly (170) is that buttress assembly (190) includes outwardly extending wing portions (194). Otherwise, buttress assembly (190) is secured to and released from staple cartridge (1270) just like buttress assembly (170) as shown in FIGS. 32A-32B. It should be understood that wing portions (194) may assist with tissue ingrowth and/or other buttress anchoring properties. In addition or in the alternative, wing portions (194) may provide a smooth transition from the relatively thick, uncompressed region of tissue to the relatively thin, compressed tissue where formed staples (90) are in the tissue. In some versions, wing portions (194) are formed with a weave density that is different from (i.e., greater than or lesser than) the weave density of the remainder of buttress assembly (190).

Figure 33:
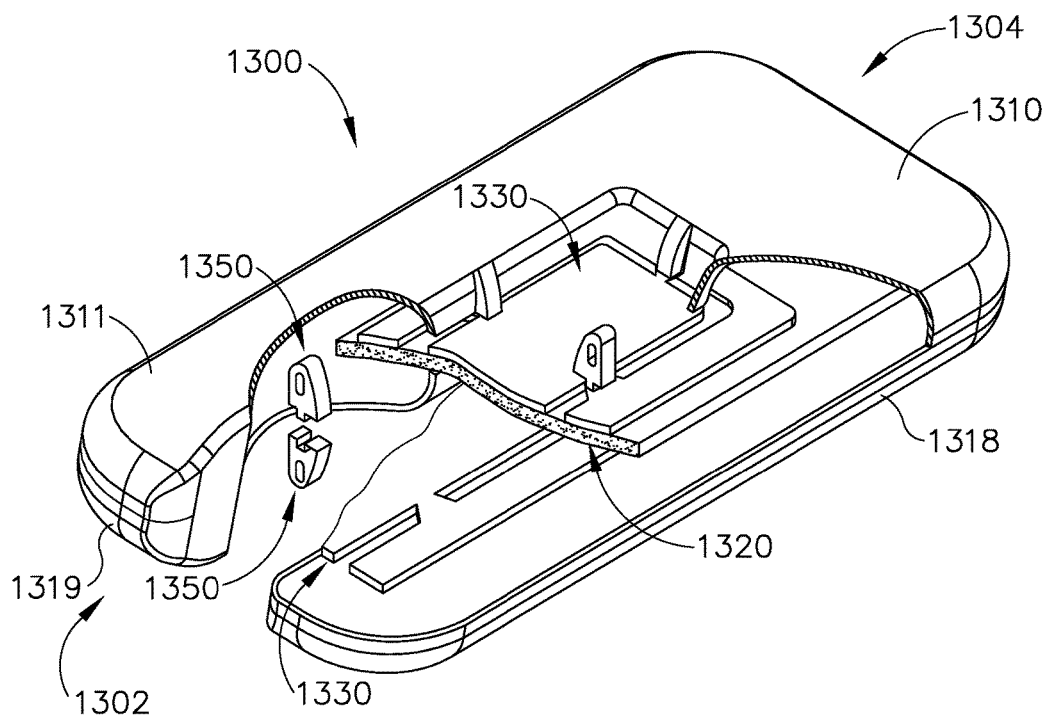
FIG. 33 depicts a perspective view of another exemplary alternative buttress applier cartridge, with a portion of the cartridge cut away to reveal internal components.

VII. Exemplary Cutting Buttress Releasing Features for Buttress Applier Cartridge In the foregoing examples that include buttress applier cartridges, the entire body (102, 112) of each buttress assembly (100, 110) is fully released from the buttress applier cartridge after an end effector (40) has been closed and opened to apply buttress assemblies (100, 110) to end effector (40). In some instances, it may be desirable to have the buttress applier cartridge retain a first portion of the body of the buttress assembly, even after a second portion of the buttress assembly has been applied to an end effector (40). To that end, FIG. 33 shows an exemplary alternative buttress applier cartridge (1300) that may be used to support and protect upper and lower buttress assemblies (1330). Cartridge (1300) may also be used to easily load upper and lower buttress assemblies (1330) on end effector (40). Cartridge (1300) of this example includes an open end (1302) and a closed end (1304) defined by upper and lower housings (1310, 1318). Cartridge (1300) further includes and a platform (1320) supporting a pair of buttress assemblies (1330). Buttress assemblies (1330) are releasably secured to cartridge (1300) by a set of retainers (1350).

Figure 34:
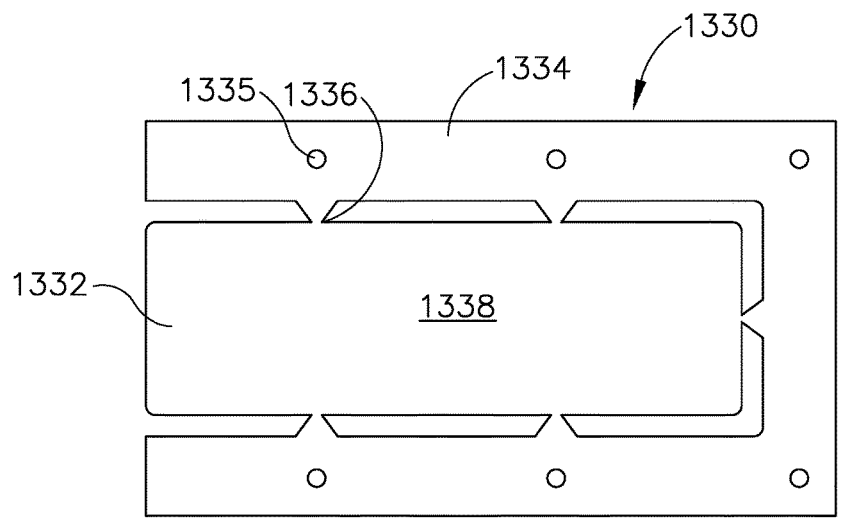
FIG. 34 depicts a top plan view of a buttress assembly of the buttress applier cartridge of FIG. 33.

FIG. 34 shows buttress assembly (1330) in greater detail. Buttress assembly (1130) includes an inner body portion (1332) and an outer body portion (1334) that are joined together by a set of bridge portions (1336) in the form of webs. An adhesive layer (1338) is positioned on inner body portion (1332) but not outer body portion (1334). The material composition of body portions (1332, 1334) and adhesive layer (1338) may be the same for that described above with respect to body portion (102, 112) and adhesive layer (104, 114), respectively. Inner body portion (1332) is rectangular and is sized and configured to correspond with the gap defined laterally between the prongs (1311) of housing (1310), which is the same as the gap defined laterally between the prongs (1319) of housing (1318). It should be understood that the size and configuration of this gap also corresponds to the clamping footprint of end effector (40). Outer body portion (1334) has a "U" shape and is sized and configured to fit within the hollow interior defined between housings (1310, 1318). Outer body portion (1334) includes a set of openings that are sized and positioned to receive corresponding posts of housings (1310, 1318), to thereby secure the positioning of outer body portion (1334) between housings (1310, 1318).

Bridge portions (1336) of buttress assembly (1330) are sized and positioned to correspond with retainers (1350). As best seen in FIGS. 50A-50B, each retainer (1350) comprises a buttress engagement foot (1352), an integral blade (1354), a cam surface (1356), and ratchet teeth (1358). Foot (1352) is rounded in this example and is configured to press bridge portion (1336) against platform (1320), thereby assisting in holding the position of buttress assembly (1330) on platform (1320). Blade (1354) projects downwardly and is configured to sever bridge portion (1336) as will be described in greater detail below. Cam surface (1356) is configured to engage anvil (60) during closure of end effector (40) as will also be described in greater detail below. While the present example is provided in the context of engagement with anvil (60), it should be understood that cam surfaces (1356) of retainers (1350) on the underside of platform (1320) would similarly engage staple cartridge (70) during closure of end effector (40). Ratchet teeth (1358) are positioned and configured to engage a fixed pawl (1312). Fixed pawl (1312) is unitary with (or is otherwise fixedly secured to) housing (1310, 1318).

Figure 35A:
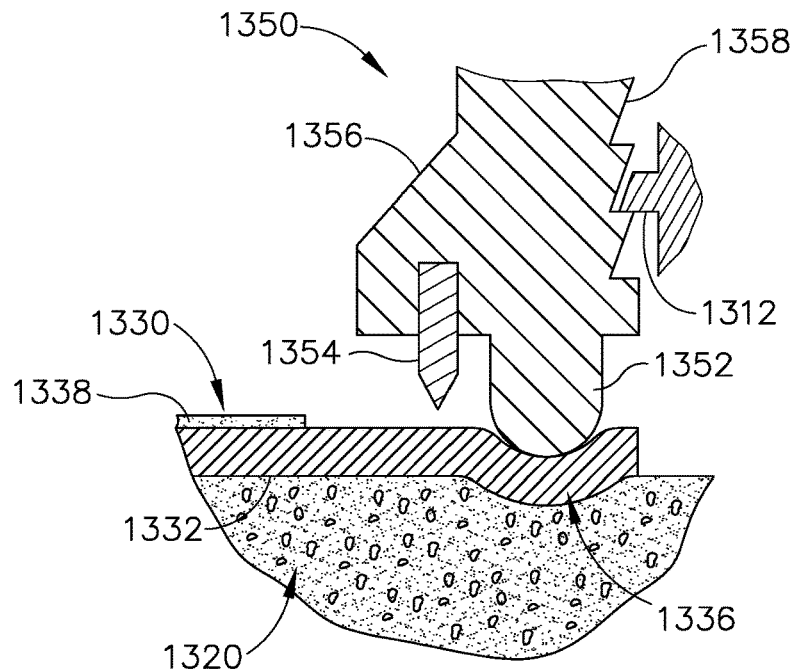
FIG. 35A depicts a cross-sectional detail view of a buttress retention member of the buttress applier cartridge of FIG. 33, with the buttress retention member in a first position.
Figure 35B:
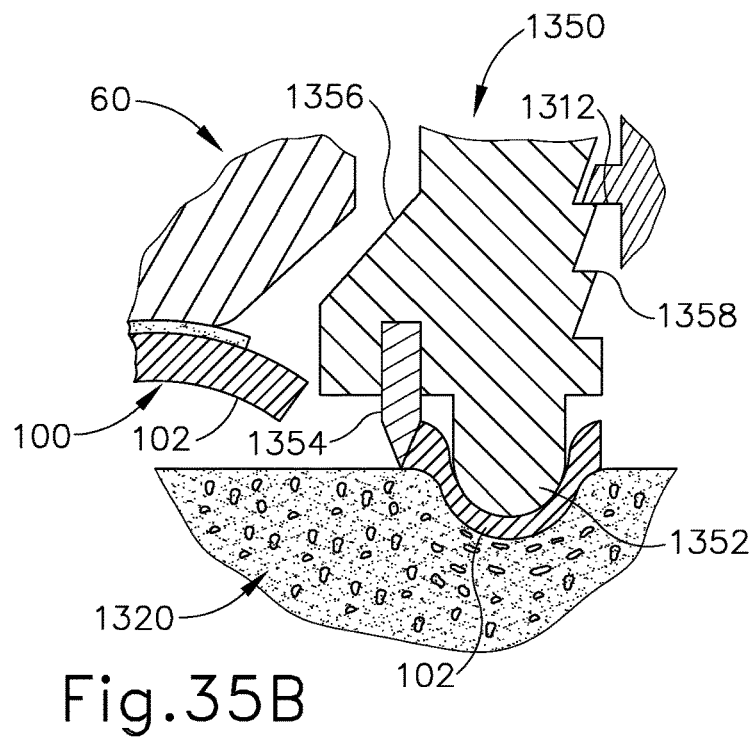
FIG. 35B depicts a cross-sectional detail view of a buttress retention member of the buttress applier cartridge of FIG. 33, with the buttress retention member driven to a second position by the anvil of the end effector of FIG. 2.
Figure 36A:
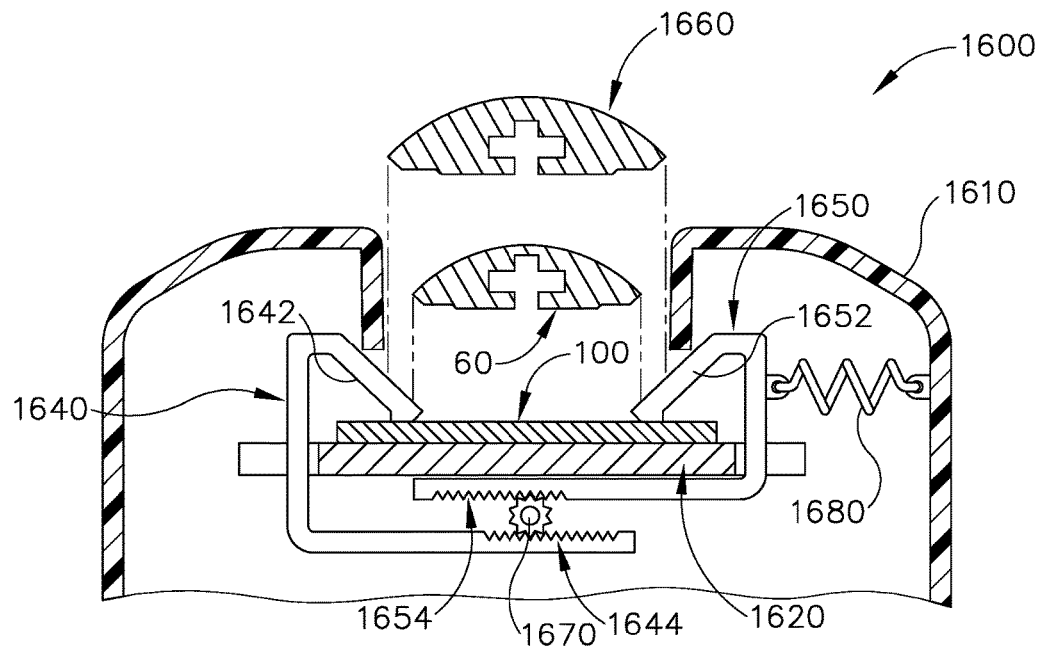
FIG. 36A depicts a partial cross-sectional end view of another exemplary alternative buttress applier cartridge, with the anvil of the end effector of FIG. 2 positioned over a platform of the buttress applier cartridge.
Figure 36B:
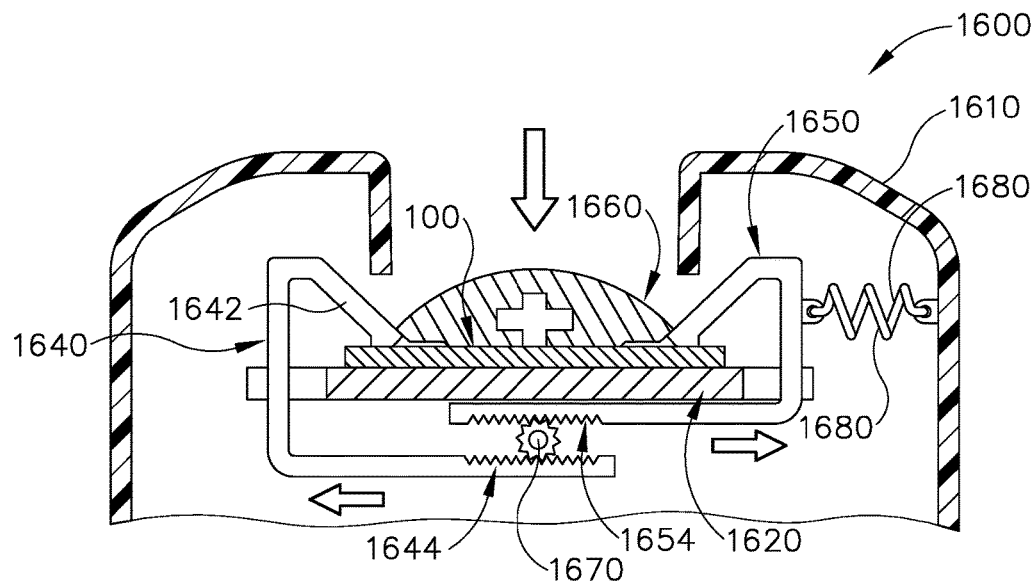
FIG. 36B depicts a partial cross-sectional end view of the buttress applier cartridge of FIG. 36A, with the anvil engaging guide features and a buttress on the platform.

In the state shown in FIG. 35A, teeth (1358) cooperate with pawl (1312) to maintain a vertical position of retainer (1350) where foot (1352) is pressing bridge portion (1336) against platform (1320). Blade (1354) is spaced away from bridge portion (1336). As end effector (40) is closed about buttress assemblies (1330) and platform (1320), the lateral edge of anvil (60) engages cam surface (1356) and thereby drives retainer (1350) downwardly to the position shown in FIG. 35B. Platform (1320) is formed of a compliant material in this example, such that platform (1320) accommodates the additional pressing of foot (1352) into platform (1320). As retainer (1350) is driven downwardly, blade (1354) severs bridge portion (1336), thereby decoupling inner body portion (1332) from outer body portion (1334). Inner body portion (1332) is thus free to be pulled away from platform (1320). Adhesive layer (1338) adheres inner body portion (1332) to underside (65) of anvil (60), such that anvil (60) will freely pull inner body portion (1332) away from cartridge (1300) as end effector (40) is subsequently opened. Teeth (1358) again cooperate with pawl (1312) to maintain the lowered vertical position of retainer (1350). It should be understood that teeth (1358) will ratchet along pawl (1312) during the transition from the state shown in FIG. 35A to the state shown in FIG. 35B.

VIII. Exemplary End Effector Alignment Features for Buttress Applier Cartridge

In some instances, it may be desirable to configure buttress assembly (100) such that the lateral width of buttress assembly (100) closely matches the lateral width of underside (65) of anvil (60). Likewise, it may be desirable to configure buttress assembly (110) such that the lateral width of buttress assembly (110) closely matches the lateral width of deck (73) of anvil (70). Matching these widths may present little to no margin of error with respect to alignment of end effector (40) with buttress assemblies (100, 110). It may therefore be desirable to provide features that ensure or otherwise promote proper alignment of end effector (40) with buttress assemblies (100, 110). Such alignment may include proper lateral positioning of end effector along a lateral plane (i.e., a plane that is parallel to the planes defined by buttress assemblies (100, 110)). Such alignment may also include proper "yaw" positioning about an axis that is perpendicular to the same lateral plane (i.e., a plane that is parallel to the planes defined by buttress assemblies (100, 110)). Several examples of features that may be used to ensure or otherwise promote proper alignment of end effector (40) with buttress assemblies (100, 110) are described in greater detail below, while other examples will be apparent to those of ordinary skill in the art in view of the teachings herein.

In addition to or as an alternative to providing visual cues to promote proper alignment between end effector (40) and a buttress applier cartridge, it may be desirable to incorporate structural features in a buttress applier cartridge to ensure proper alignment. A few merely illustrative examples of structural guide features are described in greater detail below, while other examples will be apparent to those of ordinary skill in the art in view of the teachings herein.

Those of ordinary skill in the art will further recognize that surgical stapling and severing instruments (10) may come in a variety of sizes, including different sizes with end effectors (40) having different lateral widths. It may therefore be desirable to enable a buttress applier cartridge to be used with end effectors (40) having different lateral widths. Moreover, it may be desirable for such a buttress applier cartridge to also provide proper lateral alignment between buttress assemblies (100, 110) and end effectors (40) having different lateral widths. To that end, FIGS. 54A-54B show an exemplary buttress applier cartridge (1600) that is configured to accommodate a relatively narrow anvil (60) and a relatively wide anvil (1660). While FIGS. 54A-54B only show an upper portion of cartridge (1600) associated with anvils (60, 1660), it should be understood that cartridge (1600) may have a similarly configured lower portion that is associated with staple cartridges (70) and lower jaws (50) of different widths.

Cartridge (1600) of the present example comprises a housing (1610), a platform (1620), a first retention feature (1640), a second retention feature (1650), a pinion (1670), and a resilient member (1680). Platform (1620) supports buttress assembly (100) just like various other platforms described herein. Retention feature (1640) comprises a retention arm (1642) and an integral rack (1644). Retention feature (1650) also comprises a retention arm (1652) and an integral rack (1654). While just two retention features (1640, 1650) are shown in FIGS. 54A-54B, it should be understood that several additional retention features (1640, 1650) may be positioned along the length of cartridge (1600). Racks (1644, 1654) are engaged with pinion (1670), which is rotatably supported in housing (1610). Racks (1644, 1654) are engaged with pinion (1670) at regions of pinion (1670) that are angularly offset by 180 degrees. Thus, racks (1644, 1654) will translate simultaneously in opposing directions as pinion (1670) rotates. Resilient member (1680) is positioned between retention feature (1650) and housing (1610). In the present example, resilient member (1680) is in the form of a coil spring that urges retention features (1640, 1650) toward each other.

Arms (1642, 1652) are configured to bear against buttress assembly (100) to thereby secure buttress assembly (100) against platform (1620). Arms (1642, 1652) are also angled to cooperate with outer lateral edges of anvil (60, 1660) as anvil (60, 1660) is clamped down toward buttress assembly (100) and platform (1620). In particular, as anvil (60, 1660) is clamped down toward buttress assembly (100) and platform (1620), the outer edges outer lateral edges of anvil (60, 1660) will engage angled surfaces of arms (1642, 1652), which will drive arms (1642, 1652) outwardly. Because arms (1642, 1652) are coupled together via racks (1644, 1654) and pinion (1670), arms (1642, 1652) will translate outwardly simultaneously, at the same rate, for the same distance. While this occurs, the angled surfaces of arms (1642, 1652) will guide anvil (60, 1660) downwardly along a path that is centered along a vertical plane passing longitudinally through the central longitudinal axis of buttress assembly (100) and platform (1620). In other words, retention features (1640, 1650) and pinion (1670) will cooperate to not only accommodate anvils (60, 1660) having different widths; but also to ensure that anvil (60, 1660) remains properly centered along the vertical plane passing through the lateral center of buttress assembly (100) and platform (1620). Retention features (1640, 1650) and pinion (1670) thus ensure that buttress assembly (100) has proper lateral alignment on anvil (60, 1660) regardless of whether a narrow anvil (60) or wide anvil (1660) is used.

IX. Exemplary Multi-Stage Buttress Applier Cartridge

Figure 37:
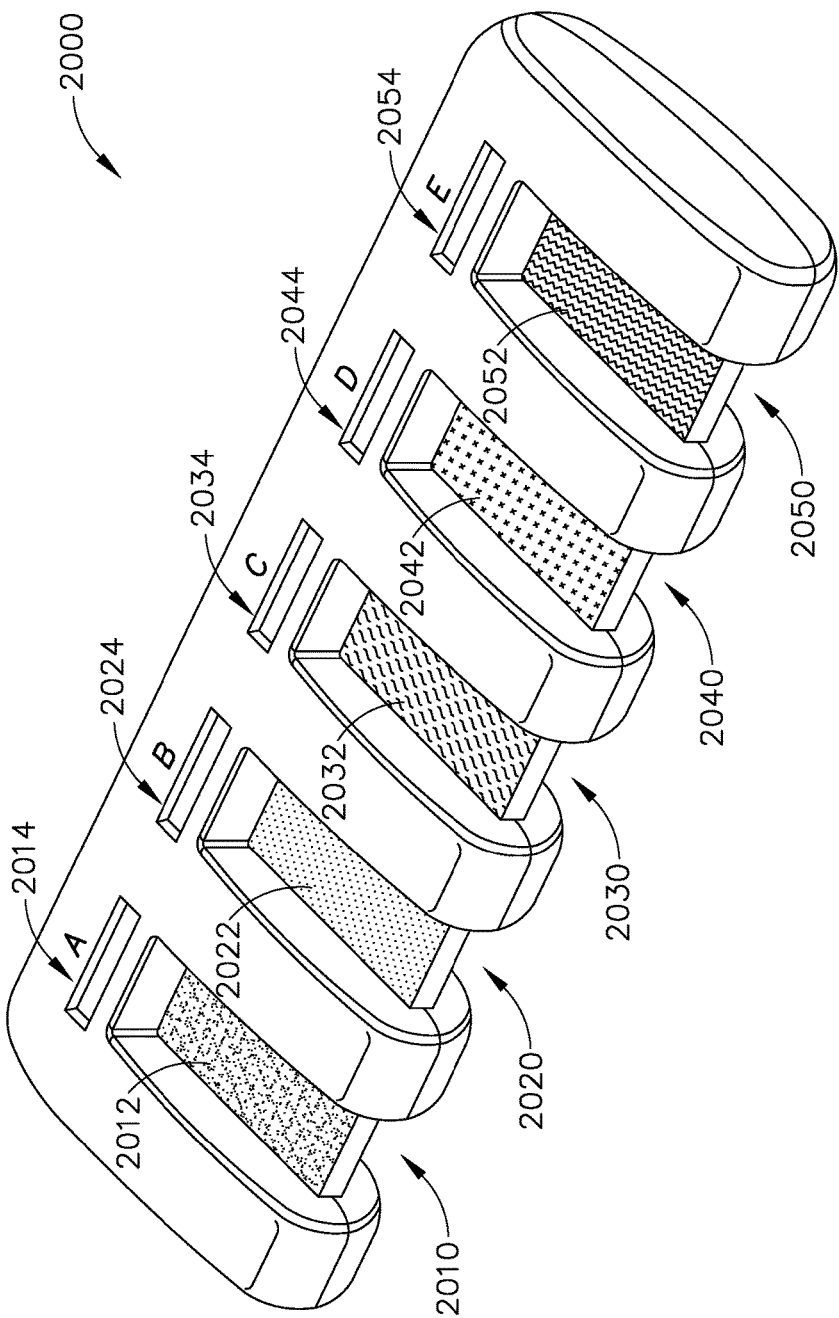
FIG. 37 depicts a perspective view of another exemplary alternative buttress applier cartridge.

In some instances, it may be desirable to provide an operator with a buttress applier cartridge that provides the operator with more options than just simply applying buttress assemblies (100, 110) in a single stroke of end effector (40). For instance, FIG. 37 shows a buttress applier cartridge (2000) that provides a plurality of stations (2010, 2020, 2030, 2040, 2050) for an operator to choose from. Each station (2010, 2020, 2030, 2040, 2050) is sized and configured to receive end effector (40). Each station (2010, 2020, 2030, 2040, 2050) includes a respective panel (2012, 2022, 2032, 2042, 2052) that the operator may clamp on with end effector (40). In the present example, panel (2012) includes a low strength adhesive disposed thereon. Panel (2022) includes a high strength adhesive disposed thereon. Panel (2032) includes a buttress body (e.g., like buttress body (102) disposed thereon. In some versions, panel (2032) includes a plurality of buttress bodies (e.g., similar to the arrangement described above with reference to FIGS. 28-29). It should therefore be understood that cartridge (2000) may be used repeatedly to apply a series of buttress assemblies (100, 110) to a single end effector (40) during a single surgical procedure. Panel (2042) includes a hydrophilic drying material disposed thereon. Panel (2052) includes an abrasive material disposed thereon. Of course, these are just merely illustrative examples, and it should be understood that panels (2012, 2022, 2032, 2042, 2052) may have any other suitable features and/or materials disposed thereon. In the present example, each station (2010, 2020, 2030, 2040, 2050) includes an identifier (2014, 2024, 2034, 2044, 2054) associated with each panel (2012, 2022, 2032, 2042, 2052). Each identifier (2014, 2024, 2034, 2044, 2054) indicates the features or materials that re disposed on the corresponding panel (2012, 2022, 2032, 2042, 2052).

In an exemplary use of cartridge (2000), an operator may first clamp end effector (40) on panel (2012) to pick up adhesive; then clamp on panel (2032) to pick up bodies (102, 112), thereby forming buttress assemblies (100, 110) on end effector (40). The operator may then insert end effector (40) into a patient and then actuate end effector (40) to apply staples (90) and buttress bodies (102, 112) to tissue. The operator may then remove end effector (40) from the patient, remove the spent cartridge (70) from lower jaw (50), and swish end effector (40) in saline to at least partially clean end effector (40). The operator may then use panel (2052) to scrub end effector (2052) to remove any excess adhesive material from underside (65) of anvil (60), swish end effector (40) again in saline, then dry end effector (40) on panel (2042). The operator may then load a new staple cartridge (70) in lower jaw (50) and repeat the above process by clamping again on panel (2012) to pick up adhesive, etc. Of course, cartridge (2000) may be used in any other suitable fashion. It should be understood that an operator may clamp end effector (40) on any number of panels (2012, 2022, 2032, 2042, 2052) and in any suitable sequence.

It should also be understood that some variations of cartridge (2000) may include a panel having a lubricant. The lubricant may be applied to end effector (40) after buttress assemblies (100, 110) are applied do end effector (40). The lubricant may facilitate placement of buttress assemblies (100, 110) on tissue without buttress assemblies (100, 110) becoming misaligned on end effector (40) due to sliding contact with tissue. Other suitable variations will be apparent to those of ordinary skill in the art in view of the teachings herein.

X. Exemplary Alternative Buttress Assembly Configurations

As noted above, the configurations of buttress assemblies (100, 110) shown in FIG. 4 are merely illustrative examples. Moreover, as shown in FIG. 19 and other drawings of the present application, each buttress assembly (100, 110) may be provided in two laterally spaced apart portions, with the two portions of each buttress assembly (100, 110) being separated by a gap that complements the width of channels (62, 72) in anvil (60) and staple cartridge (70). In versions where a buttress assembly (100, 110) is provided in two portions that are laterally separated by a gap, it may be desirable to provide one or more features that generally maintain the lateral spacing of those portions. Such features may also ensure (or at least promote) that the portions remain generally parallel with each other in addition to ensuring (or at least promoting) that the portions are separated by a consistent gap. FIGS. 38-41 show merely illustrative examples of structures that may be used to provide such functionality in buttress assemblies (100, 110). It should be understood that the modifications described below may be readily incorporated into any of the versions of buttress assemblies (100, 110) described above; and that the modified buttress assemblies described below may be readily used with any of the various buttress applier cartridges described above.

Figure 38:
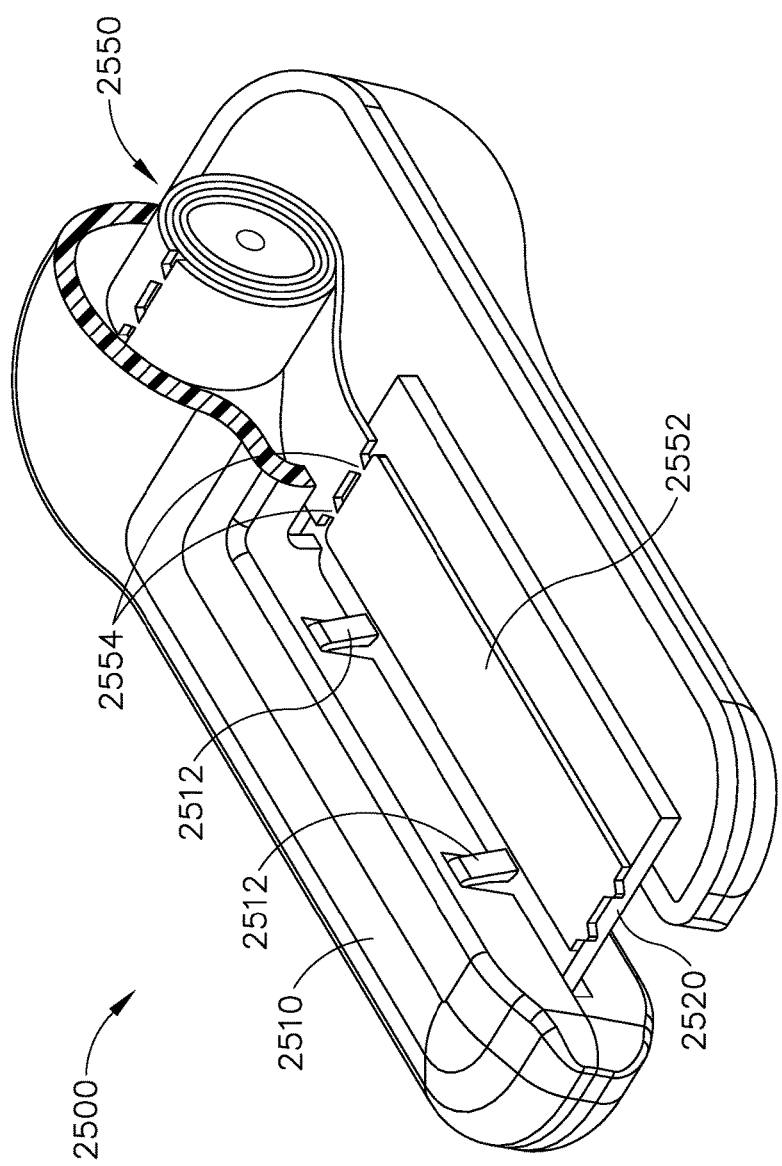
FIG. 38 depicts a perspective view of another exemplary alternative buttress applier cartridge and package with another exemplary alternative buttress assembly.
Figure 39:
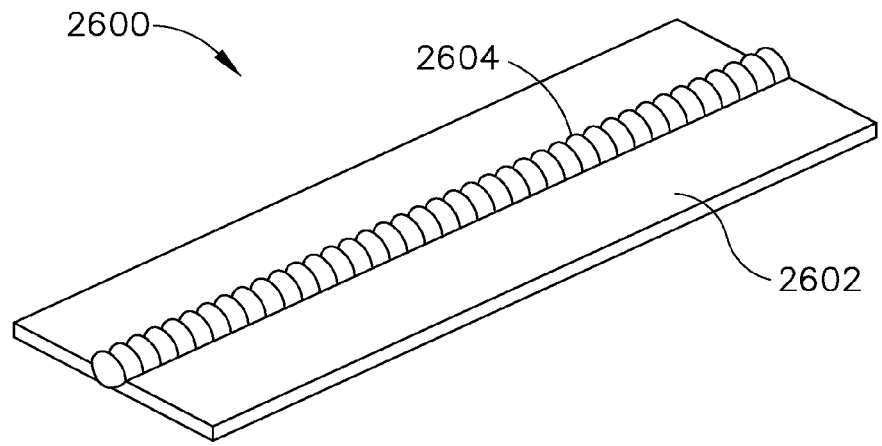
FIG. 39 depicts a perspective view of an exemplary alternative buttress assembly.

FIG. 38 shows a buttress applier cartridge (2500) containing yet another exemplary alternative buttress assembly (2550). Cartridge (2500) of this example comprises a housing (2510), retention features (2512), and a platform (2520) similar to other housings, retention features, and platforms described herein. Buttress assembly (2500) of this example is substantially identical to buttress assembly (100, 110) except that buttress assembly (2500) is in the form of a roll that is contained within housing (2510). The roll comprises a plurality of segments (2552) that are separated by weak portions (2554). Each segment (2552) has a length complementing the length of underside (65) and/or the length of deck (73). Weak portions (2554) are configured to enable an operator to easily tear one segment (2552) from the next segment (2552). Thus, the operator may use the same cartridge (2500) to apply several different segments (2552) to an end effector (40) during a single surgical procedure. It should be understood that buttress assembly (2550) may also be incorporated into cartridge (2000) described above with reference to FIG. 37 (e.g., with buttress assembly (2550) being applied via panel (2032)). Other suitable variations will be apparent to those of ordinary skill in the art in view of the teachings herein.

FIGS. 38-41 show an exemplary alternative buttress assembly (2600) that comprises a buttress body (2602) and an attachment feature (2604). Buttress body (2602) may be constructed and operable just like any other buttress body described herein and/or like any buttress body described in any references cited herein. Attachment feature (2604) comprises a hollow tubular structure that is secured to one side of buttress body (2602). In particular, attachment feature (2604) extends along the full length of buttress body (2602) and is laterally centered on buttress body (2602). While attachment feature (2604) extends continuously along the full length of buttress body (2602) in this example, it should be understood that attachment feature (2604) may instead be broken into segments that are longitudinally spaced apart from each other. In the present example, attachment feature (2604) comprises an extruded absorbable polymer (e.g., PGA, etc.) that is thermally bonded to buttress body (2602). Alternatively, any other suitable material(s) may be used to form attachment feature (2604); and any other suitable techniques may be used to secure attachment feature (2604) to buttress body (2602).

Figures 40A, 40B:
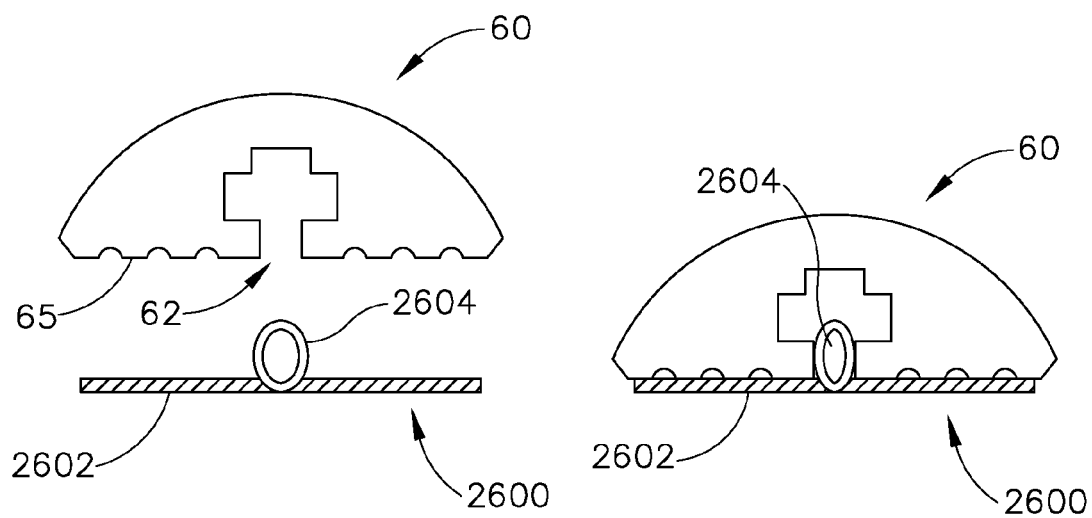
FIG. 40A depicts an end view of the anvil of the end effector of FIG. 2 positioned positioned over the buttress assembly of FIG. 39.
FIG. 40B depicts an end view of the buttress assembly of FIG. 39 secured to the anvil of the end effector of FIG. 2.

Attachment feature (2604) is resiliently biased to have a circular cross-sectional configuration as best seen in FIG. 40A. However, attachment feature (2604) is configured and dimension such that attachment feature (2604) may be compressed inwardly to deformably fit within channel (62) of anvil (60) as shown in FIG. 40B. When attachment feature (2604) is located within channel (62), the hoop stresses imposed by the resilient bias of attachment feature (2604) will provide friction against the inner sidewalls of anvil (60) that define channel (62), thereby securing attachment feature (2604) within channel (62). The secure positioning of attachment feature (2604) within channel (62) will further secure buttress body (2602) against underside (65) of anvil (60). It should therefore be understood that attachment feature (2604) may be used in lieu of providing an adhesive layer on buttress body (2602) to secure buttress body (2602) against underside (65) of anvil (60). Alternatively, attachment feature (2604) may be used to supplement an adhesive layer on buttress body (2602) to secure buttress body (2602) against underside (65) of anvil (60). It should also be understood that attachment feature (2604) may be fitted within channel (62) by anvil (60) closing down on buttress assembly (2600), such that buttress assembly (2600) may be readily used with the various buttress applier cartridges described herein.

Figure 41:
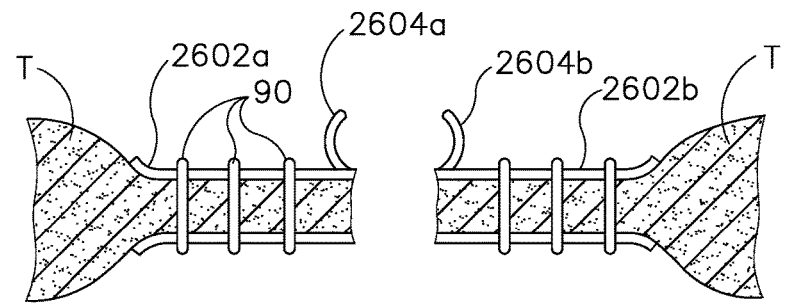
FIG. 41 depicts a cross-sectional view of the buttress assembly of FIG. 39 secured to tissue and severed.

When an end effector (40) that is loaded with buttress assembly (2600) is actuated, knife member (80) may bisect attachment feature (2604) along a longitudinal cut path while knife member (80) simultaneously bisects buttress body (2602) along the same path. This may result in a configuration as shown in FIG. 41. In particular, FIG. 41 shows buttress body (2602) bisected into two pieces (2602a, 2602b) that are secured to corresponding regions of tissue (T) via staples (90); with attachment feature (2604) also having been bisected into two corresponding pieces (2604a, 2604b). While buttress assembly (2600) is shown and described in the foregoing example as being used with anvil (60), it should be understood that buttress assembly (2600) may also be readily used with staple cartridge (70). In particular, attachment feature (2604) may be positioned on the underside of a buttress body (2602); and may fit within channel (72) of staple cartridge (70).

XI. Exemplary Alternative Features for Securing Buttress Assembly to Anvil

Figure 42:
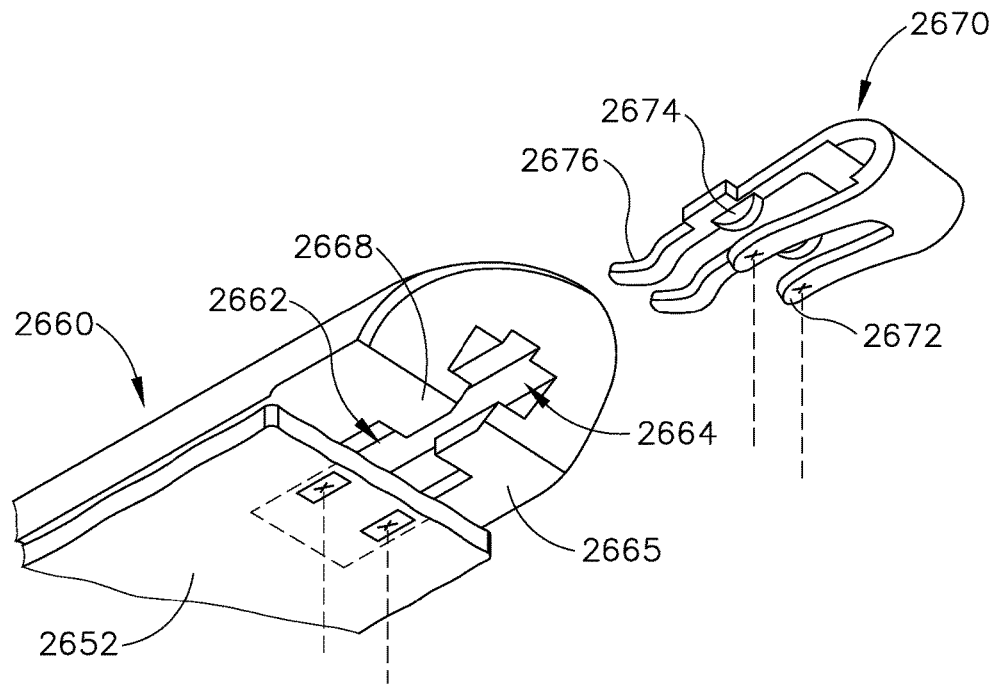
FIG. 42 depicts a perspective view of a distal end of an exemplary alternative anvil with a buttress retention clip separated from the anvil.
Figure 43A:
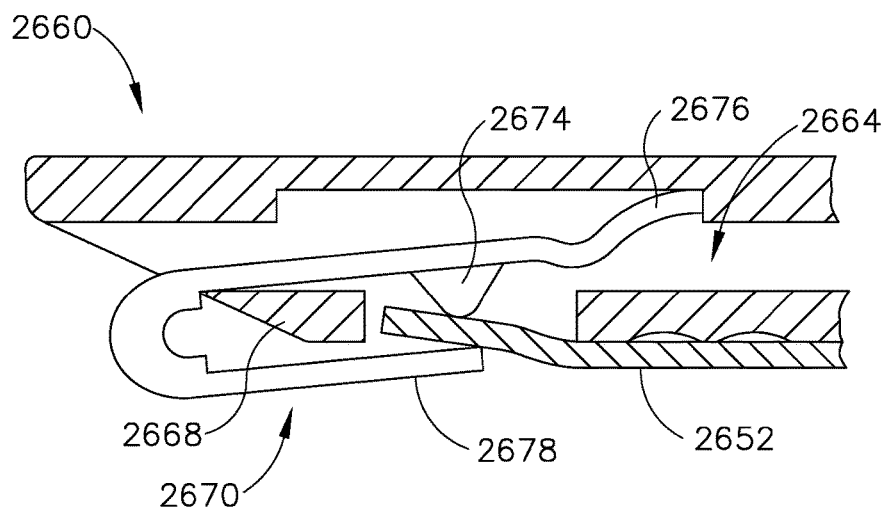
FIG. 43A depicts a cross-sectional side view of the distal end of the anvil and buttress retention clip of FIG. 42, with the clip retaining a buttress against the anvil.
Figure 43B:
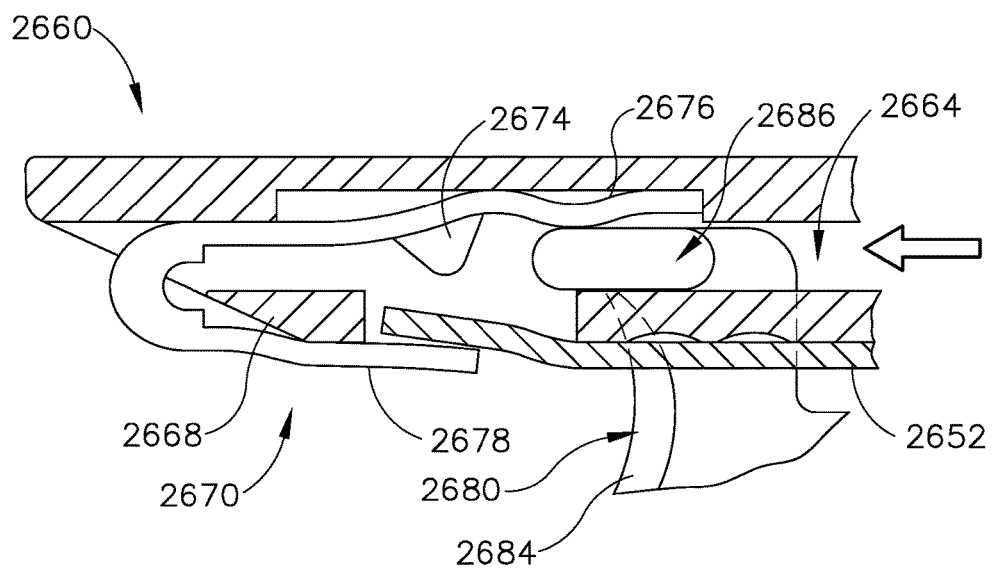
FIG. 43B depicts a cross-sectional side view of the distal end of the anvil and buttress retention clip of FIG. 42, with the clip releasing the buttress from the anvil.

As indicated above with respect to attachment feature (2604), it may be desirable to use something other than an adhesive (or in addition to an adhesive) in order to removably secure a buttress body to an end effector (40). To that end, FIGS. 42-43B show an exemplary alternative combination of a buttress body (2652), anvil (2660), and retention clip (2670). Buttress body (2652) may be constructed and operable just like any other buttress body described herein and/or like any buttress body described in any references cited herein. Anvil (2660) of this example is substantially identical to anvil (2660) described above; except that anvil (2660) of this example includes a transverse slot (2664) that is in communication with longitudinally extending channel (2662). Moreover, the distal end of anvil (2660) includes inwardly directed projections (2688) adjacent to channel (2662) and slot (2664).

Clip (2670) of the present example generally defines a "U" shape and includes a set of buttress engagement prongs (2672), a set of humps (2674), and a set of flange prongs (2676). As best seen in FIGS. 43A-43B, clip (2670) is configured to wrap around projections (2688), with flange prongs (2676) being positioned in slot (2664) and with buttress engagement prongs (2678) extending underneath projections (2688). Clip (2670) is resiliently biased to assume the configuration shown in FIG. 43A. In this configuration, prongs (2678) pinch the distal end of buttress body (2652) against underside (2665) of anvil (2660). Since clip (2670) is secured to anvil (2660), the pinching of buttress body (2652) between prongs (2678) and humps (2674) will assist in securing buttress body (2652) against underside (2665) of anvil (2660). In some versions, clip (2670) serves as a substitute for an adhesive to secure buttress body (2652) against underside (2665) of anvil (2660). In some other versions, clip (2670) serves as a supplement for an adhesive to secure buttress body (2652) against underside (2665) of anvil (2660).

Clip (2670) of the present example is configured to interact with a modified version of knife member (80) to selectively release buttress body (2652) from underside (2665) of anvil (2660) when end effector (40) is actuated. In particular, FIG. 43B shows a modified knife member (2680) interacting with clip member (2670). Knife member (2680) is substantially identical to knife member (80) and includes a cutting edge (2684); but knife member (2680) further includes a pair of upper flanges (2686) in this example. Flanges (2686) extend transversely outwardly from the upper region of knife member (2680) and are slidably disposed in slot (2664) of anvil (2660). As knife member (2680) is translated to the distal position shown in FIG. 43B, flanges (2686) engage prongs (2676) and thereby drive a first portion of clip (2670) upwardly. Projections (2668) bear downwardly on a second portion of clip (2670) as flanges (2686) drive the first portion of clip (2670) upwardly. This provides separation between prongs (2678) and humps (2674), such that clip (2670) releases buttress body (2652) as shown in FIG. 43B. It should therefore be understood that knife member (2680) will deform clip (2670) and thereby cause clip (2670) to release buttress body (2652) when knife member (2680) reaches a distal position during actuation of end effector (40).

While retention clip (2670) is shown and described in the foregoing example as being used with a modified anvil (2660), it should be understood that retention clip (2670) (or a modification thereof) may also be readily used with a modification of staple cartridge (70). In particular, retention clip (2670) may be located at the distal end of staple cartridge (70) and may deform in response to engagement by a lower flange of knife member (2680), thereby releasing a lower buttress body from the deck (73) of the modified staple cartridge (70).

XII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a housing defining a gap configured to receive a portion of an end effector of a surgical stapler; (b) a platform, wherein a portion of the platform is exposed in the gap defined by the housing; (c) a first buttress assembly positioned on the platform, wherein the buttress assembly is exposed in the gap defined by the housing; and (d) at least one retainer member configured to selectively retain the first buttress assembly against the platform, wherein the at least one retainer member is further configured to release the first buttress assembly from the platform in response to a clamping action of an end effector positioned in the gap defined by the housing.

EXAMPLE 2

The apparatus of Example 1, wherein the housing defines a U shape.

EXAMPLE 3

The apparatus of any one or more of Examples 1 through 2, wherein the platform is formed of a compressible material.

EXAMPLE 4

The apparatus of any one or more of Examples 1 through 3, wherein the first buttress assembly comprises: (i) a body, and (ii) an adhesive layer.

EXAMPLE 5

The apparatus of Example 4, wherein the adhesive layer is exposed in the gap defined by the housing.

EXAMPLE 6

The apparatus of any one or more of Examples 1 through 5, further comprising a second buttress assembly, wherein the first buttress assembly is positioned on a first side of the platform, wherein the second buttress assembly is positioned on a second side of the platform.

EXAMPLE 7

The apparatus of any one or more of Examples 1 through 6, wherein the housing further comprises a set of end effector alignment features, wherein the end effector alignment features are configured to engage an end effector positioned in the gap defined by the housing to thereby provide lateral alignment and yaw alignment of the end effector relative to the first buttress assembly

EXAMPLE 8

The apparatus of any one or more of Examples 1 through 7, wherein the at least one retainer member comprises a plurality of fingers, wherein the first buttress assembly comprises an outer region interposed between the plurality of fingers and the platform.

EXAMPLE 9

The apparatus of Example 8, wherein the fingers are configured to resiliently bear against the first buttress assembly and the platform.

EXAMPLE 10

The apparatus of any one or more of Examples 1 through 9, wherein the at least one retainer member is configured to move between a first position and a second position, wherein the at least one retainer member configured to selectively retain the first buttress assembly against the platform when the at least one retainer member is in the first position, wherein the at least one retainer is further configured to release the first buttress assembly from the platform when the at least one retainer member is in the second position.

EXAMPLE 11

The apparatus of Example 10, wherein the first buttress assembly defines a longitudinal axis, wherein the at least one retainer member is configured to move along a path that is transverse to the longitudinal axis to thereby move from the first position to the second position.

EXAMPLE 12

The apparatus of any one or more of Examples 9 through 10, further comprising a sled member, wherein the sled member is configured to drive the at least one retainer member from the first position to the second position in response to a clamping action of an end effector positioned in the gap defined by the housing.

EXAMPLE 13

The apparatus of Example 12, wherein the sled member is resiliently biased to drive the at least one retainer member from the first position to the second position.

EXAMPLE 14

The apparatus of Example 13, further comprising a latch, wherein the latch is configured to engage the housing and the sled member to thereby hold the sled member in a position where the sled member holds the at least one retainer member in the first position, wherein the latch is further configured to disengage the sled member in response to a clamping action of an end effector positioned in the gap defined by the housing to thereby permit the sled member to drive the at least one retainer member from the first position to the second position.

EXAMPLE 15

The apparatus of Example 14, wherein the latch has a first cam feature and a second cam feature, wherein the first cam feature is positioned and configured to engage an anvil of an end effector positioned in the gap defined by the housing, wherein the second cam feature is positioned and configured to engage a staple cartridge of an end effector positioned in the gap defined by the housing.

EXAMPLE 16

The apparatus of Example 15, wherein the latch is configured to require clamping engagement of both an anvil against the first cam feature and a staple cartridge against the second cam feature, respectively, in order to disengage the sled member.

EXAMPLE 17

The apparatus of any one or more of Examples 12 through 16, further comprising a set of pins secured to the at least one retainer member, wherein the sled member defines a set of slots, wherein the pins are disposed in the slots of the sled member, wherein the slots are configured to cooperate with the pins to drive the at least one retainer member to disengage the first buttress assembly in response to movement of the sled member.

EXAMPLE 18

The apparatus of Example 17, wherein each slot of the set of slots comprises a longitudinally extending portion and an obliquely extending portion.

EXAMPLE 19

The apparatus of any one or more of Examples 12 through 18, further comprising an indicator member coupled with the sled member, wherein the housing further defines a window, wherein the indicator member and the window are configured such that a first portion of the indicator member is visible through the window when the sled member is positioned to hold the at least one retainer member in the first position, wherein the indicator member and the window are configured such that a second portion of the indicator member is visible through the window when the sled member is actuated to move the at least one retainer member to the second position.

EXAMPLE 20

The apparatus of any one or more of Examples 12 through 19, wherein the at least one retainer member is configured to move relative to the housing in order to transition from the first position to the second position.

EXAMPLE 21

The apparatus of Example 20, wherein the at least one retainer member is configured to deform in order to move relative to the housing to thereby transition from the first position to the second position.

EXAMPLE 22

The apparatus of Example 21, wherein the at least one retainer member comprises an angled cam surface, wherein the cam surface is configured to engage a clamping end effector positioned in the gap defined by the housing and thereby drive the at least one retainer member to deformably move from the first position to the second position in response to clamping forces exerted by the end effector.

EXAMPLE 23

The apparatus of any one or more of Examples 1 through 22, wherein the at least one retainer member comprises a set of fins, wherein the fins are formed by the housing, wherein the fins are configured to bear against the first buttress assembly and thereby hold the first buttress assembly against the platform.

EXAMPLE 24

The apparatus of any one or more of Examples 1 through 23, wherein the platform extends along a longitudinal axis, wherein the platform is configured to slide relative to the housing from a first longitudinal position to a second longitudinal position, wherein the platform is retracted relative to the cartridge when the platform is in the first longitudinal position, wherein the platform is extended relative to the cartridge when the platform is in the second longitudinal position.

EXAMPLE 25

The apparatus of Example 24, wherein the platform and the housing comprise complementary latching features, wherein the complementary latching features are configured to cooperate to retain the platform in the second longitudinal position in response to translation of the platform from the first longitudinal position to the second longitudinal position.

EXAMPLE 26

The apparatus of any one or more of Examples 1 through 25, wherein the at least one retainer member comprises an arm having a ratcheting feature, wherein the platform comprises a rigid lateral edge, wherein the at least one retainer member is configured to ratchet along the rigid lateral edge of the platform in response to a clamping action of an end effector positioned in the gap defined by the housing, wherein the ratcheting feature and the lateral edge are configured to cooperate to maintain the at least one retainer member in a deflected state in response to the ratcheting of the at least one retainer member along the rigid lateral edge.

EXAMPLE 27

The apparatus of any one or more of Examples 1 through 26, further comprising a second buttress assembly laid over the first buttress assembly, wherein the at least one retainer member is configured to retain the first and second buttress assemblies on the platform and release the first and second buttress assemblies from the platform in a succession in response to a corresponding successive clamping action of an end effector positioned in the gap defined by the housing.

EXAMPLE 28

The apparatus of any one or more of Examples 1 through 27, wherein the first buttress assembly includes an outer region extending into the housing and an inner region positioned in the gap defined by the housing, wherein the at least one retainer is operable to sever the inner region from the outer region in response to a clamping action of an end effector positioned in the gap defined by the housing.

EXAMPLE 29

The apparatus of Example 28, wherein the at least one retainer comprises an integral blade, wherein the at least one retainer is configured to move from a first position to a second position, wherein the at least one retainer is configured to provide a gap between the integral blade and the first buttress assembly is in the first position, wherein the at least one retainer is configured to drive the integral blade through the first buttress assembly during movement of the at least one retainer from the first position to the second position.

EXAMPLE 30

The apparatus of Example 29, wherein the at least on retainer and the housing comprise complementary locking features, wherein the locking features are configured to lock the at least one retainer in the second position in response to the at least one retainer moving from the first position to the second position.

EXAMPLE 31

The apparatus of any one or more of Examples 1 through 30, wherein the gap comprises an upper portion and a lower portion, wherein the upper portion has a first width configured to complement a width of an anvil of an end effector of a surgical stapler, wherein the lower portion has a second width configured to complement a width of a lower jaw of an end effector of a surgical stapler.

EXAMPLE 32

The apparatus of Example 31, wherein the second width is greater than the first width.

EXAMPLE 33

The apparatus of any one or more of Examples 1 through 32, wherein the at least one retainer member comprises: (i) a first retainer arm having an angled surface, (ii) a second retainer arm having an angled surface, and (iii) a resilient member, wherein the first and second retainer arms are configured to translate away from each other in response to a clamping action of an end effector positioned in the gap defined by the housing, wherein the resilient member is configured bias the first and second retainer arms away from each other.

EXAMPLE 34

The apparatus of Example 33, wherein the first retainer arm further comprises a first integral rack, wherein the second retainer arm further comprises a second integral rack, wherein the at least one retainer member further comprises a pinion engaged with the first and second integral racks, wherein the pinion and the first and second integral racks are configured to cooperate to provide coordinated movement of the first and second retainer arms away from each other.

EXAMPLE 35

The apparatus of any one or more of Examples 1 through 34, wherein the housing further comprises a plurality of stations, wherein each station includes a corresponding gap and a corresponding panel, wherein each gap is configured to receive a portion of an end effector of a surgical stapler, wherein a first station of the plurality of stations comprises a buttress assembly station, wherein a first panel of the first station comprises the platform.

EXAMPLE 36

The apparatus of Example 35, wherein a second station of the plurality of stations comprises an adhesive applying station, wherein a second panel of the second station includes an adhesive material.

EXAMPLE 37

The apparatus of Example 36, wherein a third station of the plurality of stations comprises an adhesive applying station, wherein a third panel of the second station includes an adhesive material, wherein the adhesive material on the third panel is configured to provide stronger adhesion than the adhesive material on the second panel.

EXAMPLE 38

The apparatus of any one or more of Examples 35 through 37, wherein a fourth station of the plurality of stations comprises a drying station, wherein a fourth panel of the third station includes a hydrophilic material.

EXAMPLE 39

The apparatus of any one or more of Examples 35 through 38, wherein a fifth station of the plurality of stations comprises a cleaning station, wherein a fifth panel of the fourth station includes an abrasive material.

EXAMPLE 40

The apparatus of any one or more of Examples 1 through 39, wherein the first buttress assembly comprises a roll of material, wherein a free portion of the roll of material is on the platform, wherein the at least one retainer member configured to selectively retain the free portion against the platform.

EXAMPLE 41

The apparatus of Example 40, wherein the roll is contained in the housing.

EXAMPLE 42

The apparatus of any one or more of Examples 40 through 41, wherein the roll of material further includes a plurality of weak portions, wherein the weak portions are arranged to separate the roll of material into discrete lengths of buttress material, wherein the discrete lengths each correspond to a length of the platform.

EXAMPLE 43

A staple cartridge, comprising: (a) a body wherein the body includes a deck; (b) a plurality of staples contained in the body; (c) a wedge sled, wherein the wedge sled is configured to translate longitudinally through the body and thereby drive the staples through the deck; (d) a buttress laid over the deck; and (e) a thread, wherein the thread is configured to releasably secure the buttress to the deck.

EXAMPLE 44

The staple cartridge of Example 43, wherein the body defines a plurality of thread channels, wherein the thread channels are configured to receive the thread to thereby secure the thread to the body, thereby securing the buttress to the deck.

EXAMPLE 45

The staple cartridge of Example 44, wherein the body further defines a set of wings extending laterally outwardly relative to the deck, wherein the thread channels are formed through the wings.

EXAMPLE 46

The staple cartridge of any one or more of Examples 43 through 45, wherein the thread is secured to the wedge sled, wherein the thread is configured to release the buttress from the deck in response to the wedge sled translating within the body from a proximal position to a distal position.

EXAMPLE 47

The staple cartridge of any one or more of Examples 43 through 46, wherein the buttress comprises a central region extending over the deck and a pair of wings extending laterally outwardly from the central region, wherein the wings are further positioned outwardly from the deck.

EXAMPLE 48

An apparatus comprising: (a) a housing defining a gap configured to receive a portion of an end effector of a surgical stapler; (b) a platform, wherein a portion of the platform is exposed in the gap defined by the housing; (c) a first buttress assembly positioned on the platform, wherein the buttress assembly is exposed in the gap defined by the housing; (d) at least one retainer member configured to selectively retain the first buttress assembly against the platform; and (e) a release assembly in communication with the at least one retainer member, wherein the release assembly is configured to store energy, wherein the release assembly is further configured to release the stored energy to thereby cause the at least one retainer to release the first buttress assembly from the platform in response to a clamping action of an end effector positioned in the gap defined by the housing.

EXAMPLE 49

An apparatus comprising: (a) a housing defining a gap configured to receive a portion of an end effector of a surgical stapler; (b) a platform, wherein a portion of the platform is exposed in the gap defined by the housing; (c) a first buttress assembly positioned on the platform, wherein the buttress assembly is exposed in the gap defined by the housing; and (d) at least one retainer member configured to selectively retain the first buttress assembly against the platform, wherein the at least one retainer member is further configured to release the first buttress assembly from the platform in response to a clamping action of an end effector positioned in the gap defined by the housing.

EXAMPLE 50

The apparatus of Example 49, wherein the at least one retainer member is configured to move from a first position to a second position, wherein the least one retainer member configured to selectively retain the first buttress assembly against the platform when the at least one retainer member is in the first position, wherein the at least one retainer is further configured to release the first buttress assembly from the platform when the at least one retainer member is in the second position, wherein the at least one retainer member is configured to remain in the second position after reaching the second position.

EXAMPLE 51

A method of securing a buttress to an end effector, wherein the end effector comprises an upper jaw member and a lower jaw member, the method comprising: (a) positioning a platform of a buttress applier cartridge between the upper and lower jaw members while the upper and lower jaw members are in an open configuration, wherein the platform has a buttress disposed thereon during the act of positioning the platform between the upper and lower jaw members, wherein the buttress applier cartridge has at least one retainer member retaining the buttress on the platform during the act of positioning the platform between the upper and lower jaw members; (b) driving one or both of the upper or lower jaw members toward the platform to thereby engage the buttress with the end effector, wherein the buttress applier cartridge further comprises a resilient member that drives the at least one retainer away from the buttress to thereby release the buttress in response to the act of driving one or both of the upper or lower jaw members toward the platform; and (c) driving one or both of the upper or lower jaw members way from the platform to thereby pull the buttress off of the platform.

XIII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein; U.S. patent application Ser. No. 14/827,856, entitled "Implantable Layers for a Surgical Instrument," filed Aug. 17, 2015, the disclosure of which is incorporated by reference herein; U.S. patent application Ser. No. 14/871,071, entitled "Compressible Adjunct with Crossing Spacer Fibers," filed Sep. 30, 2015, published as U.S. Pub. No. 2017/0086837 on Mar. 30, 2017, the disclosure of which is incorporated by reference herein; and U.S. patent application Ser. No. 14/871,131, entitled "Method for Applying an Implantable Layer to a Fastener Cartridge," field Sep. 30, 2015, published as U.S. Pub. No. 2017/0086842 on Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," field Sep. 30, 2015, published as U.S. Pub. No. 2017/0086842 on Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a housing defining a gap that extends longitudinally between an open proximal end and a closed distal end, wherein the gap is configured to receive a portion of an end effector of a surgical stapler such that the end effector extends longitudinally within the gap and a distal end of the end effector is positioned at the closed distal end of the gap;
   (b) a platform, wherein a portion of the platform is exposed in the gap defined by the housing;
   (c) a first buttress assembly positioned on the platform, wherein the first buttress assembly is exposed in the gap defined by the housing;
   (d) at least one retainer member configured to selectively retain the first buttress assembly against the platform; and
   (e) a release assembly in communication with the at least one retainer member, wherein the release assembly is configured to store energy, wherein the release assembly is further configured to release the stored energy to thereby cause the at least one retainer member to release the first buttress assembly from the platform in response to a clamping action of the end effector positioned in the gap defined by the housing.

2. The apparatus of claim 1, wherein the housing defines a U shape.

3. The apparatus of claim 1, wherein the platform is formed of a compressible material.

4. The apparatus of claim 1, wherein the first buttress assembly comprises:
   (i) a body, and
   (ii) an adhesive layer.

5. The apparatus of claim 4, wherein the adhesive layer is exposed in the gap defined by the housing.

6. The apparatus of claim 1, wherein the release assembly is configured to move the at least one retainer member from a first position to a second position, wherein the at least one retainer member configured to selectively retain the first buttress assembly against the platform when the at least one retainer member is in the first position, wherein the at least one retainer is further configured to release the first buttress assembly from the platform when the at least one retainer member is in the second position.

7. The apparatus of claim 6, wherein the first buttress assembly defines a longitudinal axis, wherein the at least one retainer member is configured to move along a path that is transverse to the longitudinal axis to thereby move from the first position to the second position.

8. The apparatus of claim 1, further comprising a second buttress assembly, wherein the first buttress assembly is positioned on a first side of the platform, wherein the second buttress assembly is positioned on a second side of the platform.

9. The apparatus of claim 1, wherein the at least one retainer member comprises a plurality of fingers, wherein the first buttress assembly comprises an outer region interposed between the plurality of fingers and the platform.

10. The apparatus of claim 9, wherein the fingers are configured to resiliently bear against the first buttress assembly and the platform.

11. The apparatus of claim 10, wherein the release assembly comprises a sled member, wherein the sled member is configured to drive the at least one retainer member from the first position to the second position in response to a clamping action of an end effector positioned in the gap defined by the housing.

12. The apparatus of claim 11, wherein the sled member is resiliently biased to drive the at least one retainer member from the first position to the second position.

13. The apparatus of claim 12, wherein the release assembly further comprises a latch, wherein the latch is configured to engage the housing and the sled member to thereby hold the sled member in a position where the sled member holds the at least one retainer member in the first position, wherein the latch is further configured to disengage the sled member in response to a clamping action of an end effector positioned in the gap defined by the housing to thereby permit the sled member to drive the at least one retainer member from the first position to the second position.

14. The apparatus of claim 13, wherein the latch has a first cam feature and a second cam feature, wherein the first cam feature is positioned and configured to engage an anvil of an end effector positioned in the gap defined by the housing, wherein the second cam feature is positioned and configured to engage a staple cartridge of an end effector positioned in the gap defined by the housing.

15. The apparatus of claim 14, wherein the latch is configured to require clamping engagement of both an anvil against the first cam feature and a staple cartridge against the second cam feature, respectively, in order to disengage the sled member.

16. The apparatus of claim 11, wherein the release assembly further comprises a set of pins secured to the at least one retainer member, wherein the sled member defines a set of slots, wherein the pins are disposed in the slots of the sled member, wherein the slots are configured to cooperate with the pins to drive the at least one retainer member to disengage the first buttress assembly in response to movement of the sled member.

17. The apparatus of claim 16, wherein each slot of the set of slots comprises a longitudinally extending portion and an obliquely extending portion.

18. An apparatus comprising:
(a) a housing having a gap that extends along a longitudinal axis between an open proximal end and a closed distal end, wherein the gap is configured to receive a portion of an end effector of a surgical stapler such that the end effector extends along the longitudinal axis and a distal end of the end effector is positioned at the closed distal end of the gap;
(b) a platform, wherein a portion of the platform is exposed in the gap defined by the housing, wherein the platform is configured to support a buttress assembly in the gap;
(c) a retainer member configured to selectively retain the buttress assembly against the platform, wherein the retainer member is translatable laterally relative to the longitudinal axis; and
(d) a release assembly in communication with the retainer member, wherein the release assembly is configured to store energy, wherein the release assembly is further configured to release the stored energy to cause the retainer to translate laterally away from the longitudinal axis and thereby release the buttress assembly from the platform in response to a clamping action of the end effector positioned in the gap defined by the housing.

19. The apparatus of claim 18, wherein the release assembly further comprises:
a support member having a plurality of slots, and
(ii) a plurality of pins that movably couple the retainer member with the support member, wherein the pins are slidable within the slots to provide lateral translation of the retainer member relative to the support member in response to clamping of the end effector within the gap.

20. An apparatus comprising:
(a) a housing defining a gap that extends along a longitudinal axis between an open proximal end and a closed distal end, wherein the gap is configured to receive a portion of an end effector of a surgical stapler such that the end effector extends along the longitudinal axis and a distal end of the end effector is positioned at the closed distal end of the gap;
(b) a platform, wherein a portion of the platform is exposed in the gap defined by the housing, wherein the platform is configured to support a buttress assembly in the gap;
(c) a retainer member configured to selectively retain the buttress assembly against the platform; and
(d) a release assembly in communication with the retainer member, wherein the release assembly comprises:
(i) a locking member disposed at the closed distal end of the gap, wherein the locking member is movable from a locked state to an unlocked state when clamped by the end effector in the gap, and
(ii) a resilient member, wherein the resilient member is configured to release stored energy when the locking member transitions from the locked state to the unlocked state and thereby actuate the retainer to release the buttress assembly from the platform.

* * * * *